US012620069B2

(12) United States Patent
Bangerth et al.

(10) Patent No.: US 12,620,069 B2
(45) Date of Patent: May 5, 2026

(54) PROCESSING MULTIPLEX IMAGES AND ANALYSIS OF IMMUNE ENRICHED SPATIAL PROTEOMIC DATA

(71) Applicant: University of Southern California, Los Angeles, CA (US)

(72) Inventors: Sarah Bangerth, Los Angeles, CA (US); Arianna Barbetta, Los Angeles, CA (US); Juliet Ann Emamaullee, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 0 days.

(21) Appl. No.: 19/073,992

(22) Filed: Mar. 7, 2025

(65) Prior Publication Data
US 2025/0285237 A1    Sep. 11, 2025

Related U.S. Application Data

(60) Provisional application No. 63/562,886, filed on Mar. 8, 2024.

(51) Int. Cl.
    G06T 5/70        (2024.01)
    A61B 5/00        (2006.01)
        (Continued)
(52) U.S. Cl.
    CPC .............. G06T 5/70 (2024.01); A61B 5/7203 (2013.01); G06T 5/20 (2013.01); G06V 10/25 (2022.01);
        (Continued)
(58) Field of Classification Search
    CPC ........... A61B 5/7203; G06T 5/20; G06T 5/60; G06T 5/70; G06T 2207/10024;
        (Continued)

(56) References Cited

U.S. PATENT DOCUMENTS 7,129,973 B2 * 10/2006 Raynor .............. H04N 1/32128
                                                    348/231.3
8,996,810 B2 *  3/2015 Liang .................. G06F 16/2365
                                                    711/119
(Continued)

OTHER PUBLICATIONS

Abdelaal et al., Predicting Cell Populations in Single Cell Mass Cytometry Data, Cytometry Part A, vol. 95, No. 7, Jul. 2019, pp. 769-781.

(Continued)

*Primary Examiner* — Michael B. Pierorazio
(74) *Attorney, Agent, or Firm* — Kilpatrick Townsend & Stockton LLP

(57)            ABSTRACT

Techniques are disclosed herein that encompass image pre-processing and a semi-supervised clustering for optimization and analysis of immune-enriched single-cell proteomics data generated via multiplexed imaging technologies. This is achieved through an image pre-processing pipeline, which converts image data contained in one type of file (e.g., .mcd) into another type of file (e.g., .tiff) and removes artifact signals from the image data using various algorithms to generate improved image data. Thereafter, a semi-supervised clustering pipeline analyzes the improved image data using various techniques, including implementing a supervised algorithm to identify metaclusters such as general immune phenotypes (e.g., CD4-T-cells, Macrophages, Neutrophils, etc.) as well as non-immune phenotypes while implementing an unsupervised algorithm that enables the identification of specific subclusters and a more in-depth cellular status characterization.

20 Claims, 36 Drawing Sheets
(13 of 36 Drawing Sheet(s) Filed in Color)

(51) Int. Cl.

| | |
|---|---|
| *G06T 5/20* | (2006.01) |
| *G06V 10/25* | (2022.01) |
| *G06V 20/69* | (2022.01) |
| *G16H 30/40* | (2018.01) |

(52) U.S. Cl.
CPC ........... *G06V 20/695* (2022.01); *G16H 30/40* (2018.01); *G06T 2207/20182* (2013.01)

(58) Field of Classification Search
CPC . G06T 2207/20081; G06T 2207/20084; G06T 2207/20182; G06T 2207/30024; G06V 10/25; G06V 20/695; G16H 30/40
See application file for complete search history.

(56) References Cited

U.S. PATENT DOCUMENTS

| | | | | |
|---|---|---|---|---|
| 11,215,700 | B2 * | 1/2022 | Schockaert | G01S 7/4866 |
| 11,706,544 | B2 * | 7/2023 | Sawada | G06F 21/73 |
| | | | | 348/308 |
| 2014/0313390 | A1 * | 10/2014 | Uemura | G03B 13/00 |
| | | | | 348/335 |
| 2015/0116822 | A1 * | 4/2015 | Mori | G02B 21/06 |
| | | | | 359/385 |
| 2016/0327782 | A1 * | 11/2016 | Mori | A61B 1/07 |
| 2016/0377856 | A1 * | 12/2016 | Mori | H04N 9/77 |
| | | | | 348/70 |
| 2017/0094349 | A1 * | 3/2017 | Maughan | H04N 21/44226 |
| 2017/0168286 | A1 * | 6/2017 | Mori | G02B 23/2469 |
| 2017/0261135 | A1 * | 9/2017 | Mori | G02B 23/243 |
| 2017/0276925 | A1 * | 9/2017 | Mori | G02B 21/367 |
| 2018/0197306 | A1 * | 7/2018 | Fukunishi | H04N 13/211 |
| 2019/0034753 | A1 * | 1/2019 | Mori | G16B 45/00 |
| 2019/0080466 | A1 * | 3/2019 | Mori | G06T 7/593 |
| 2019/0239738 | A1 * | 8/2019 | Mori | A61B 1/00 |
| 2019/0373195 | A1 * | 12/2019 | Minagawa | G06V 40/1306 |
| 2019/0383946 | A1 * | 12/2019 | Namba | G06V 20/58 |
| 2020/0242806 | A1 * | 7/2020 | Mori | H04N 13/246 |
| 2020/0268234 | A1 * | 8/2020 | Nakagawa | G02B 23/26 |
| 2021/0056695 | A1 * | 2/2021 | Mori | G06T 7/90 |
| 2021/0097656 | A1 * | 4/2021 | Kondo | G06N 3/084 |
| 2021/0166369 | A1 * | 6/2021 | Baek | G06N 3/08 |
| 2021/0166446 | A1 * | 6/2021 | Chen | G01R 33/5608 |
| 2021/0192684 | A1 * | 6/2021 | Pardeshi | G06T 17/10 |
| 2021/0211312 | A1 * | 7/2021 | Lu | G11C 7/24 |
| 2022/0187914 | A1 * | 6/2022 | Zhao | A61B 5/372 |
| 2022/0252857 | A1 * | 8/2022 | Mori | G02B 21/367 |
| 2022/0351806 | A1 * | 11/2022 | Rey | C12Q 1/6883 |

OTHER PUBLICATIONS

Alexander et al., Exploring the Single-cell Immune Landscape of Kidney Allograft Inflammation Using Imaging Mass Cytometry, American Journal of Transplantation, vol. 24, No. 4, Apr. 2024, pp. 549-563.

Amitay et al., CellSighter: A Neural Network to Classify Cells in Highly Multiplexed Images, Nature Communication, vol. 14, No. 1, Jul. 2023, pp. 1-13.

Baba et al., CD4+/CD8+ Macrophages Infiltrating at Inflammatory Sites: A Population of Monocytes/macrophages with a Cytotoxic Phenotype, Blood, vol. 107, No. 5, Mar. 1, 2006, pp. 2004-2012.

Bai et al., Adjacent Cell Marker Lateral Spillover Compensation and Reinforcement for Multiplexed Images, Frontiers in Immunology, vol. 12, Jul. 5, 2021, pp. 1-11.

Baranski et al., Maui (Mbi Analysis User Interface)—An Image Processing Pipeline for Multiplexed Mass Based Imaging, The Public Library of Science Computational Biology, vol. 17, No. 4, Apr. 19, 2021, pp. 1-16.

Barbetta et al., Spatially Resolved Immune Exhaustion Within the Alloreactive Microenvironment Predicts Liver Transplant Rejection, Science Advances, vol. 10, No. 15, Apr. 12, 2024, pp. 1-18.

Berg et al., Ilastik: Interactive Machine Learning for (Bio)Image Analysis, Nature Methods, vol. 16, No. 12, Apr. 8, 2020, pp. 1-9.

Bortolomeazzi et al., A Simpli (Single-cell Identification from MultiPLexed Images) Approach for Spatially- resolved Tissue Phenotyping at Single-cell Resolution, Nature Communications, vol. 13, No. 1, Feb. 9, 2022, pp. 1-14.

Chevrier et al., Compensation of Signal Spillover in Suspension and Imaging Mass Cytometry, Cell Systems, vol. 6, May 23, 2018, pp. 612-620.

Geuenich et al., Automated Assignment of Cell Identity from Single-cell Multiplexed Imaging and Proteomic Data, Cell Systems, vol. 12, No. 12, Dec. 15, 2021, pp. 1173-1186.

Giesen et al., Highly Multiplexed Imaging of Tumor Tissues with Subcellular Resolution by Mass Cytometry, Nature Methods, vol. 11, No. 4, Apr. 2014, pp. 417-422.

Greenwald et al., Whole-cell Segmentation of Tissue Images with Human-level Performance Using Large-scale Data Annotation and Deep Learning, Nature Biotechnology, vol. 40, No. 4, Apr. 2022, pp. 555-565.

Ijsselsteijn et al., Semi-automated Background Removal Limits Data Loss and Normalizes Imaging Mass Cytometry Data, Cytometry Part A, vol. 99, No. 12, Dec. 2021, pp. 1187-1197.

Keren et al., MIBI-TOF: A Multiplexed Imaging Platform Relates Cellular Phenotypes and Tissue Structure, Science Advances, vol. 5, No. 10, Oct. 9, 2019, pp. 1-16.

Kim et al., Immunohistochemistry for Pathologists: Protocols, Pitfalls, and Tips, Journal of Pathology and Translational Medicine, vol. 50, No. 6, Nov. 2016, pp. 411-418.

Krop et al., Imaging Mass Cytometry Reveals the Prominent Role of Myeloid Cells at the Maternal-fetal Interface, Iscience, vol. 25, No. 7, Jul. 15, 2022, 21 pages.

Levine et al., Data-Driven Phenotypic Dissection of AML Reveals Progenitor-like Cells that Correlate with Prognosis, Cell, vol. 162, No. 1, Jul. 2, 2015, pp. 184-197.

Lu et al., IMC-Denoise: A Content Aware Denoising Pipeline to Enhance Imaging Mass Cytometry, Nature Communications, vol. 14, Article No. 1601, Mar. 23, 2023, pp. 1-16.

Milosevic, Different Approaches to Imaging Mass Cytometry Data Analysis, Bioinformatics Advances, vol. 3, No. 1, Apr. 2023, pp. 1-16.

Nicholas et al., Multiparameter Analysis of Stimulated Human Peripheral Blood Mononuclear Cells: A Comparison of Mass and Fluorescence Cytometry, Cytometry Part A, vol. 89, No. 3, Mar. 2016, pp. 271-280.

Pechuan-Jorge et al., SPEX: A Modular End-to-end Analytics Tool for Spatially Resolved Omics of Tissues, Available Online at: https://www.biorxiv.org/content/10.1101/2022.08.22.504841v1.full. pdf, Aug. 2022, pp. 1-39.

Scoazec et al., Both Macrophages and Endothelial Cells of the Human Hepatic Sinusoid Express the CD4 Molecule, a Receptor for the Human Immunodeficiency Virus, Hepatology, vol. 12, Sep. 1990, pp. 505-510.

Sorin et al., Single-cell Spatial Landscapes of the Lung Tumour Immune Microenvironment, Nature, vol. 614, Feb. 16, 2023, 24 pages.

Stirling et al., CellProfiler 4: Improvements in Speed, Utility and Usability, vol. 22, No. 433, Sep. 2021, pp. 1-11.

Takahashi et al., Mass Cytometry Panel Optimization Through the Designed Distribution of Signal Interference, Cytometry Part A, vol. 91, No. 1, Jan. 2017, pp. 39-47.

Windhager et al., An End-to-end Workflow for Multiplexed Image Processing and Analysis, Nature Protocols, vol. 18, No. 11, Nov. 2023, pp. 1-21.

Wu et al., Single-cell Analysis of the Human Pancreas in Type 2 Diabetes Using Multi-Spectral Imaging Mass Cytometry, Cell Reports, vol. 37, No. 5, Nov. 2, 2021, 24 pages.

Xiao et al., Multiplexed Imaging Mass Cytometry Reveals Distinct Tumor-immune Microenvironments Linked to Immunotherapy Responses in Melanoma, Communications Medicine, vol. 2, Article No. 131, Oct. 21, 2022, pp. 1-14.

Zanotelli et al., A Flexible Image Segmentation Pipeline for Heterogeneous Multiplexed Tissue Images Based on Pixel Classification, Available online at: https://www.imc.unibe.ch/unibe/portal/fak_

(56)          References Cited

OTHER PUBLICATIONS medizin/micro_imc/content/e987276/e1000503/e1000512/
imcsegmentationpipeline_documentation.pdf, Jan. 14, 2019, pp.
1-9.
Zhang et al., Identification of Cell Types in Multiplexed in Situ
Images by Combining Protein Expression and Spatial Information
Using CELESTA, Nature Methods, vol. 19 No. 6, Jun. 2022, pp.
759-769.

* cited by examiner

FIG. 4B

Unsupervised - FlowSOM

| Cell type | Value |
|---|---|
| Resident memory CD4+ T-cells | 18,515 |
| CD3+ CD4+ T-cells | 17,359 |
| PD1+ CD4+ T-cells | 1,300 |
| PD1+ CD28+ CD4+ T-cells | 2,700 |
| CD16+ CD4+ T-cells | 1,707 |
| CD138+ CD4+ T-cells | 5,952 |
| HLADR- CD4+ Tregs | 534 |
| CD3+ CD8+ T-cells | 12,923 |
| PD1+ Proliferating CD8+ T-cells | 1,105 |
| PD1+ CD8+ T-cells | 4,910 |
| B cells | 2,312 |
| M1 Macrophages | 16,805 |
| HLADR+ M1 Macrophages | 6,292 |
| M2 Macrophages | 13,306 |
| CD16+ M2 Macrophages | 8,566 |
| CD16+ HLADR+ M2 Macrophages | 2,775 |
| HLADR+ M2 Macrophages | 4,676 |
| CD16+ Proliferating M2 Macrophages | 641 |
| Monocytes | 4,305 |
| Granzyme B+ Monocytes | 995 |
| Neutrophils | 19,179 |
| PD1+ Neutrophils | 3,521 |
| PD1+ CD28+ Neutrophils | 1,161 |
| Cholangiocytes | 4,681 |
| Endothelial cells | 10,298 |
| Hepatocytes | 251,625 |
| Proliferating Hepatocytes | 5,121 |
| HLADR+ Hepatocytes | 19,626 |
| CD66b+ CD68+ | 837 |
| CD66b+ CD163+ CD16+ | 2,766 |
| CD16+ | 6,350 |
| CD138+ CD163+ CD16+ | 3,995 |
| Granzyme B+ | 2,916 |
| Mixed | 34 |

Column markers: CD66b, CD20, CD28, CD16, CD163, CD11b, CD45, CD4, CD31, CD279, CD68, Foxp3, CK7, Ki67, CD8, CD3, CD138, HLADR, GranzymeB 2
1
0
-1
Scaled expression

FIG. 5A Optimized

CD68 | FoxP3 | Overlay

FIG. 5B Original

CD68 | FoxP3 | Overlay

FIG. 5C Artifacts still present

CD68 | FoxP3 | Overlay

953 — M2: CD16 CD11b High
1,344 — M1: Foxp3 CD11b High
1,041 — M2: Foxp3 CD11b High
770 — M2: HLADR High
1,005 — M1: HLADR High
173 — M2: Ki67 High
130 — M1: Ki67 High
703 — M1: CD45 High
12,716 — M2: CD163/CD68 Alone
21,235 — M1: CD68 Alone CD16  CD11b  CD45  Foxp3  CD163  CD68  Ki67  HLADR Expression
0   1   2

FIG. 5E Removal of true signal

CD68 | FoxP3 | Overlay

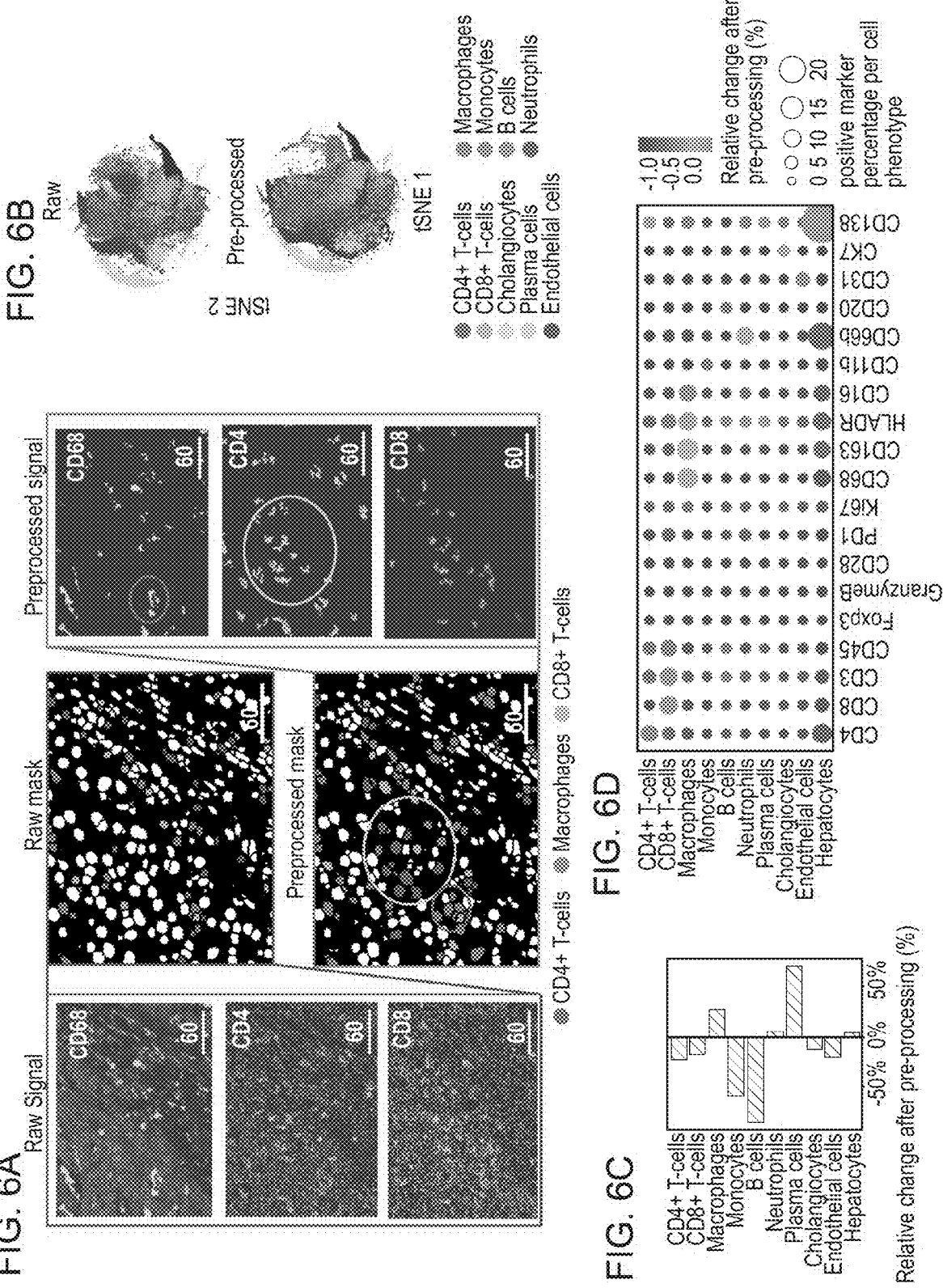

FIG. 7B

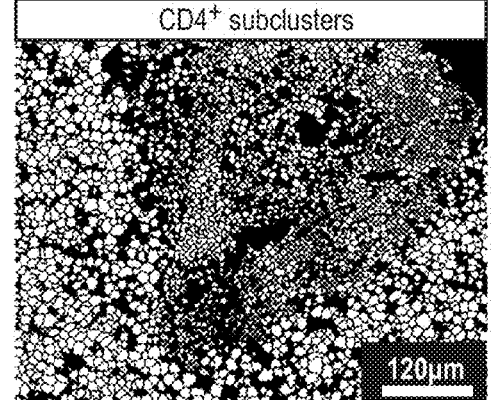

FIG. 7C

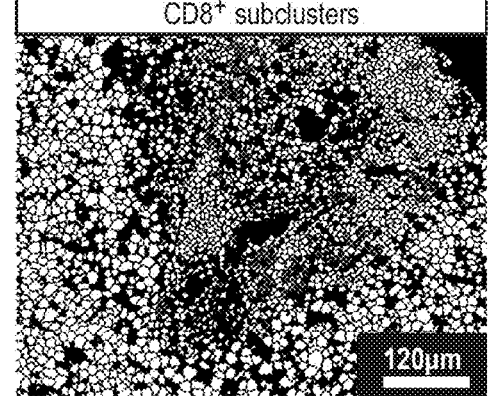

Legend
 1. CD3+ CD4+ T-cells
 2. Resident memory CD4+ T-cells
 3. HLADR+ CD4+ Tregs        9. CD3+ CD8+ T-cells
 4. HLADR- CD4+ Tregs        10. Proliferating CD8+ T-cells
 5. Naive CD4+ T-cells        11. PD1+ CD28+ CD8+ T-cells
 6. PD1+ CD4+ T-cells        12-35. Non T-cells
 7. Activated CD4+ T-cells
 8. CD16+ CD4+ T-cells

FIG. 7D

CD3+ CD4+ T-cells
Resident memory CD4+ T-cells
HLADR+ CD4+ Tregs
HLADR- CD4+ Tregs
Naive CD4+ T-cells
PD1+ CD4+ T-cells
Activated CD4+ T-cells
CD16+ CD4+ T-cells
CD3+ CD8+ T-cells
PD1+ CD28+ CD8+ T-cells
Proliferating CD8+ T-cells CD11b CD16 HLADR Ki67 PD1 CD28 Foxp3 CD45 CD3 CD8 CD4

○ ○ ○ ○  Positive marker percentage
in a cell phenotype in
0.0 2.5 5.0 7.5  pre-processed data (%)

Relative change after
pre-processing (%)

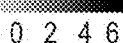

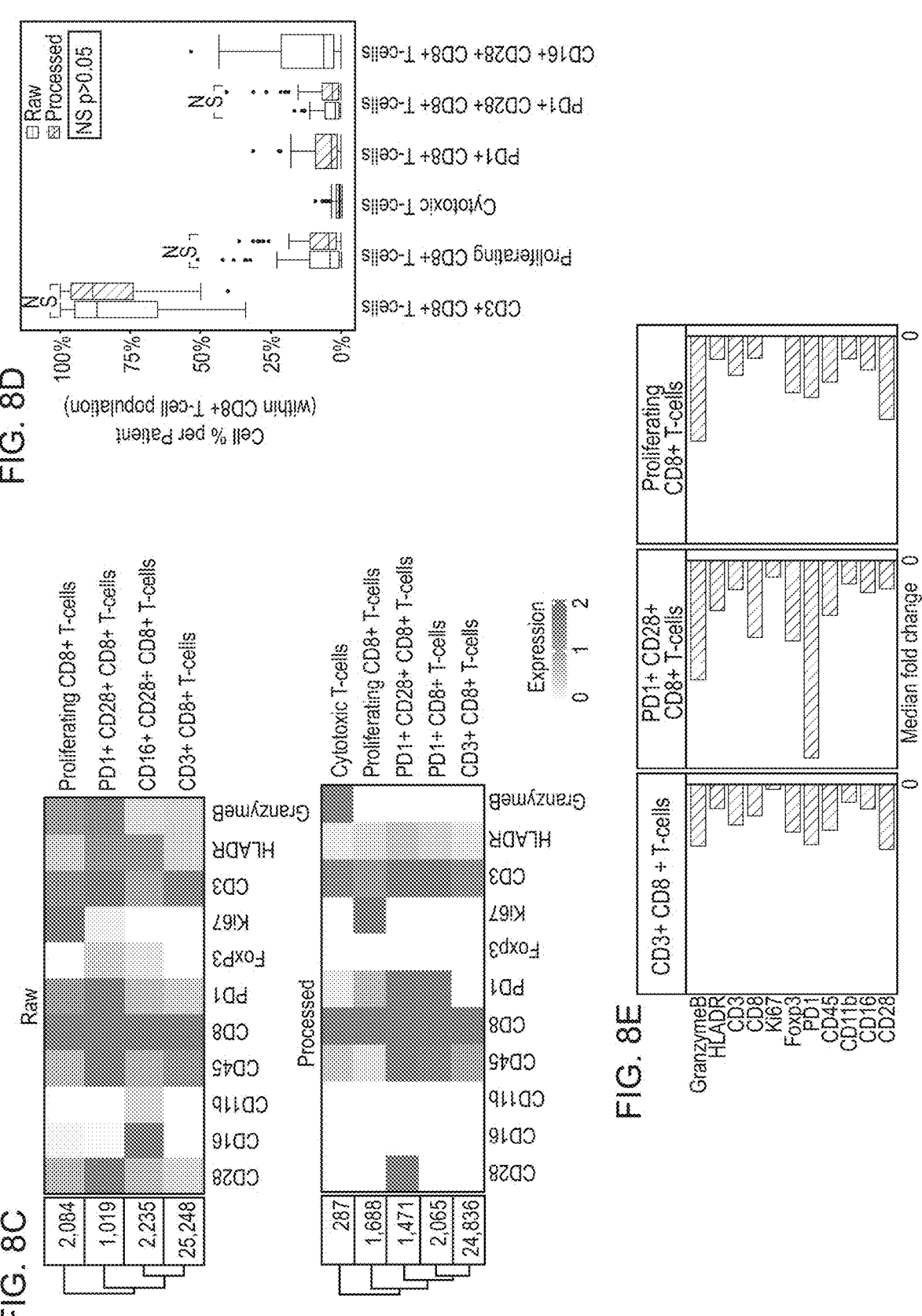

FIG. 9B

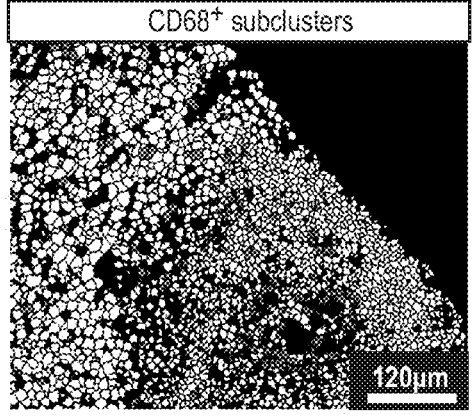

CD68⁺ subclusters

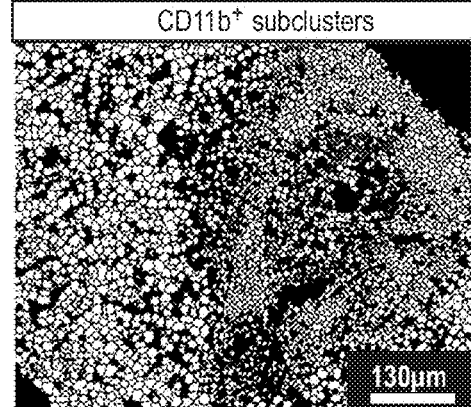

CD11b⁺ subclusters

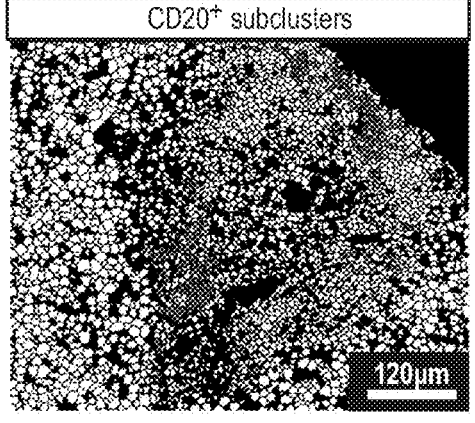

CD20⁺ subclusters

120μm

Legend
- 1. M1 macrophages
- 2. M2 macrophages
- 3. Proliferating M1 macrophages
- 4. Proliferating M2 macrophages
- 5. CD16+ M1 macrophages
- 6. CD16+ M2 macrophages
- 7. HLADR+ M2 macrophages
- 8. Classical monocytes
- 9. Intermediate monocytes
- 10. Activated monocytes
- 11. B cells
- 12. Proliferating B cells
- 13. PD1+ B cells
- 14-35. T-cells and non-immune cells

FIG. 9E

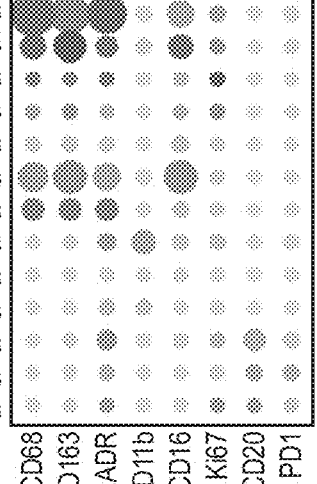

M1 macrophages
M2 macrophages
Proliferating M1 macrophages
Proliferating M2 macrophages
CD16+ M1 macrophages
CD16+ M2 macrophages
HLADR+ M2 macrophages
Classical monocytes
Intermediate monocytes
Activated monocytes
B cells
PD1+ B cells
Proliferating B cells CD68 CD163 HLADR CD11b CD16 Ki67 CD20 PD1

Relative change after
pre-processing (%)

0 2 4

0 2 4 6

Positive marker percentage
in a cell phenotype in
pre-processed data (%)

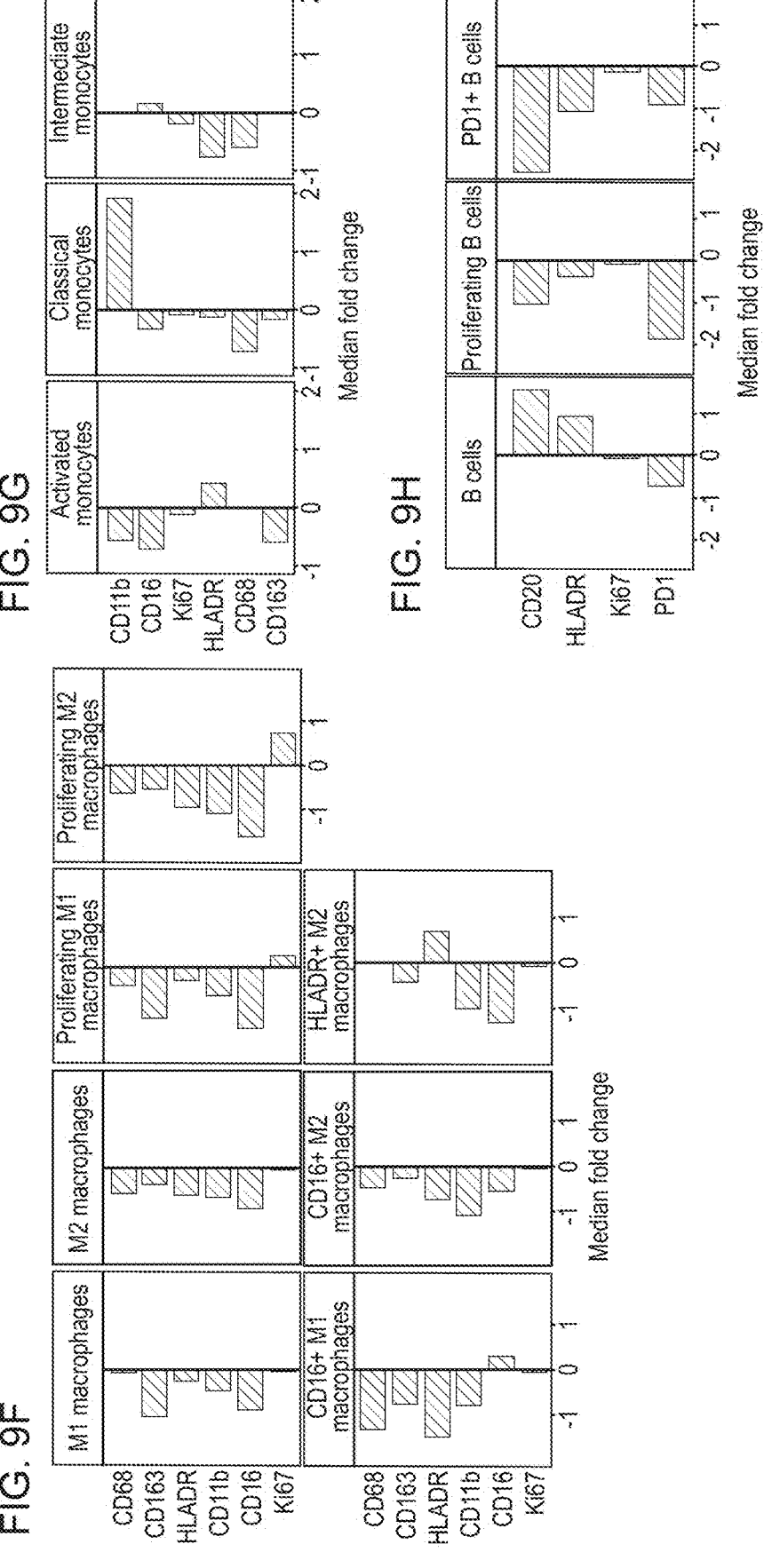

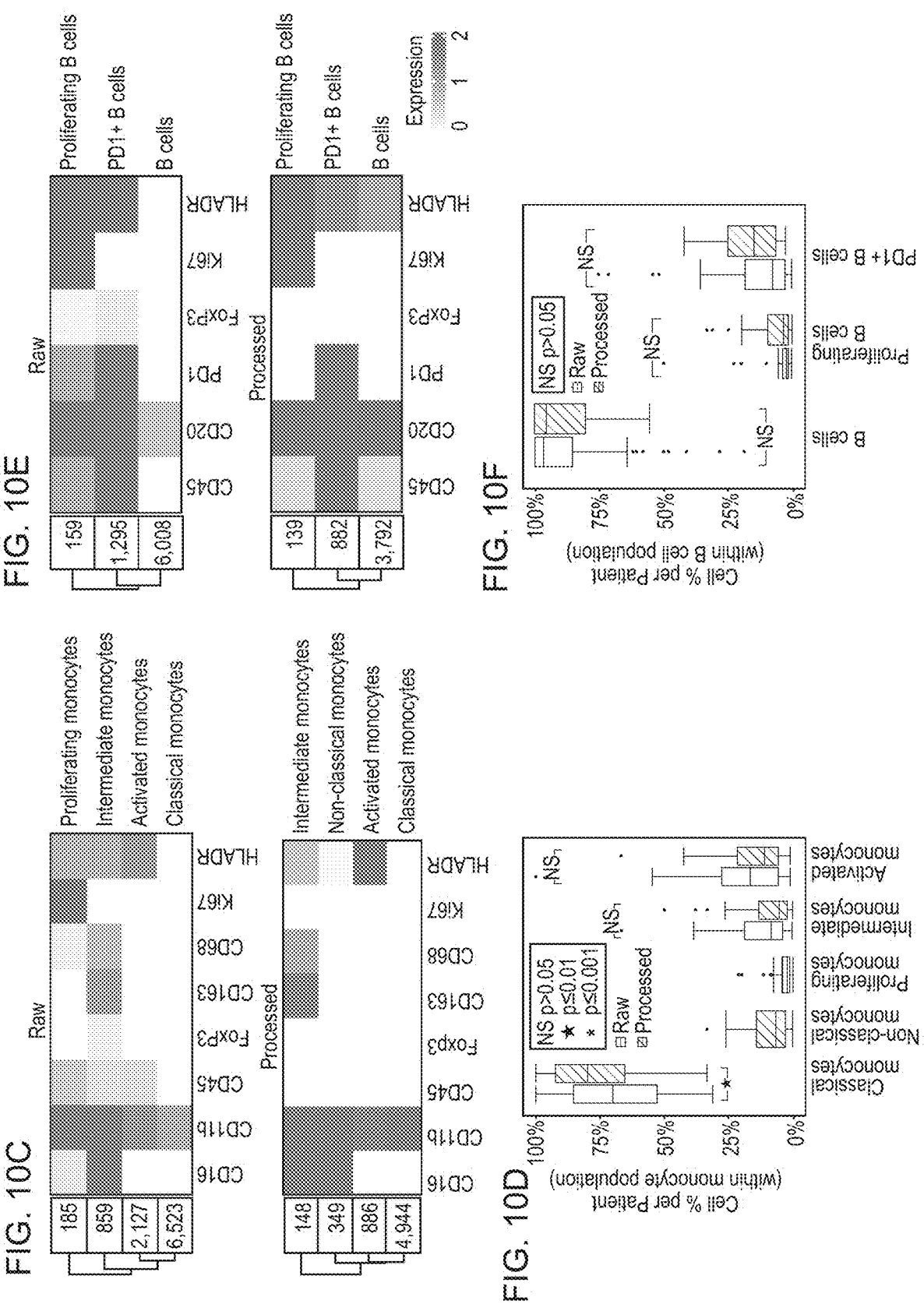

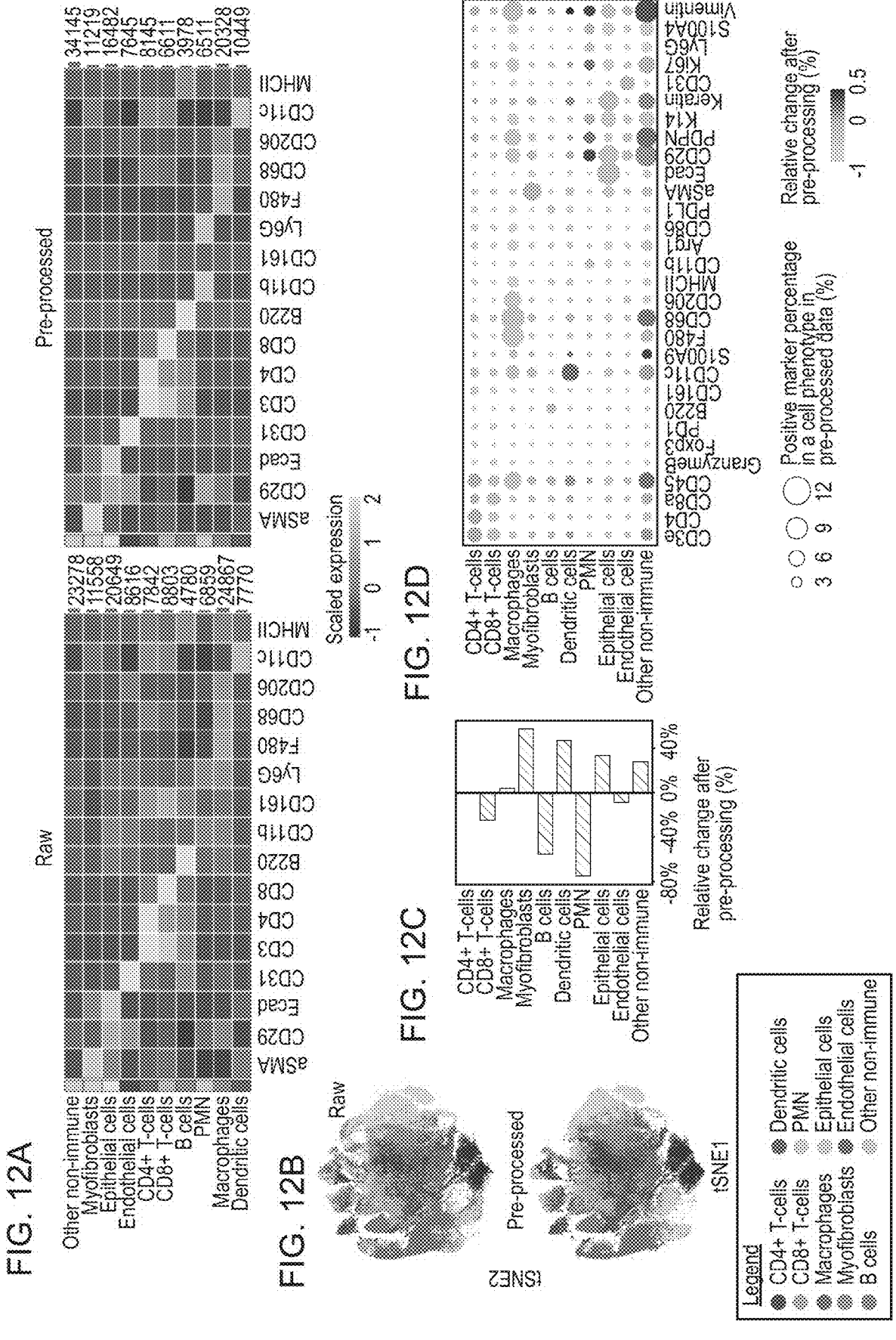

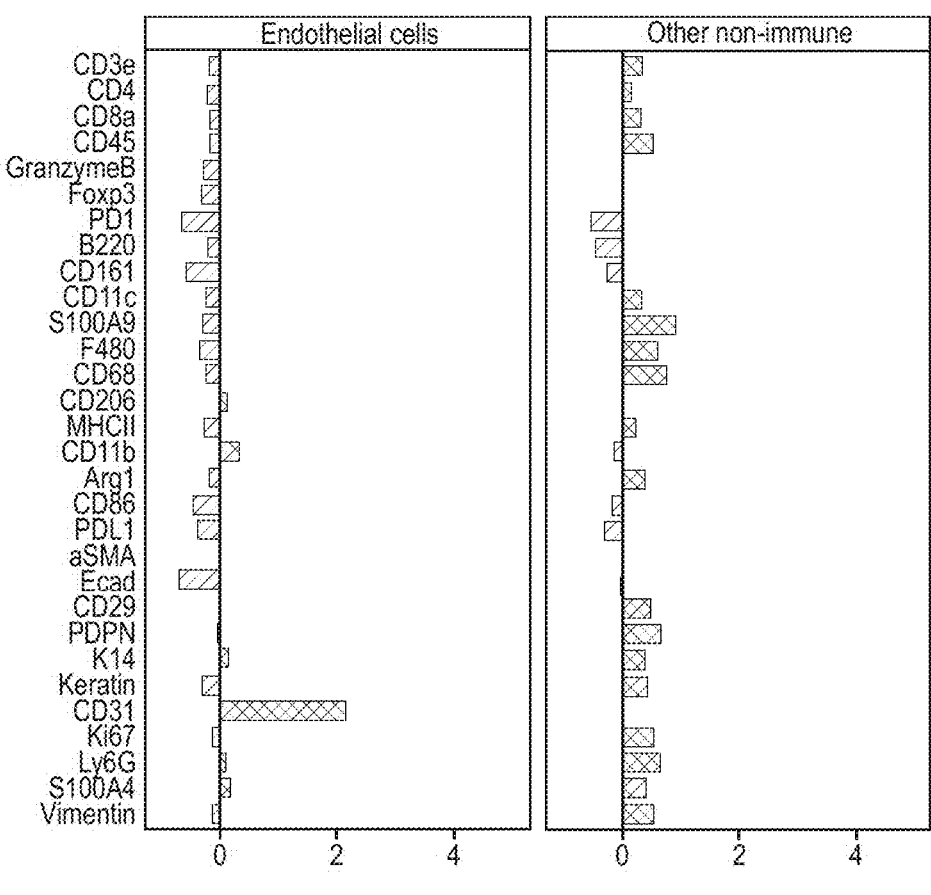
Relative change after pre-processing (%)
FIG. 12E cont.
FIG. 12F
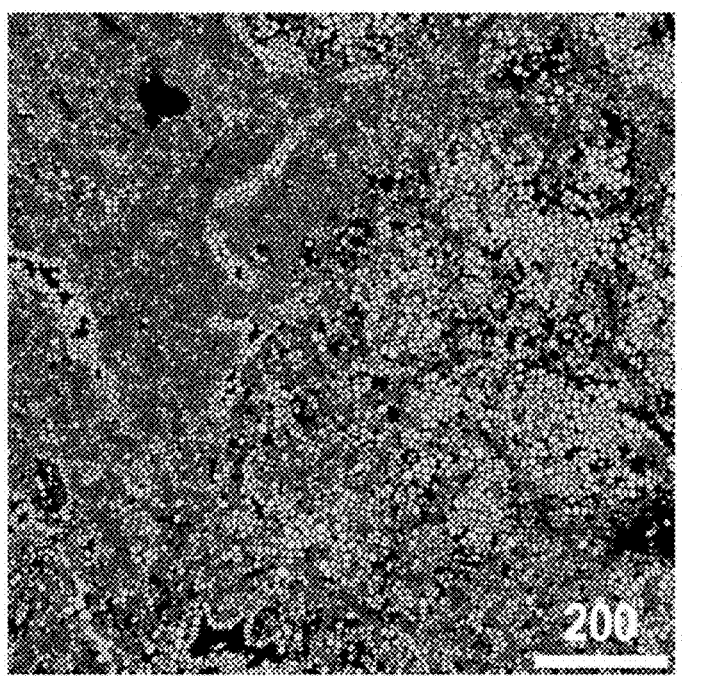
Legend
● CD4+ T-cells
● CD8+ T-cells
● Macrophages
● Myofibroblasts
● B cells
● Dendritic cells
● PMN
● Epithelial cells
● Endothelial cells
● Other non-immune

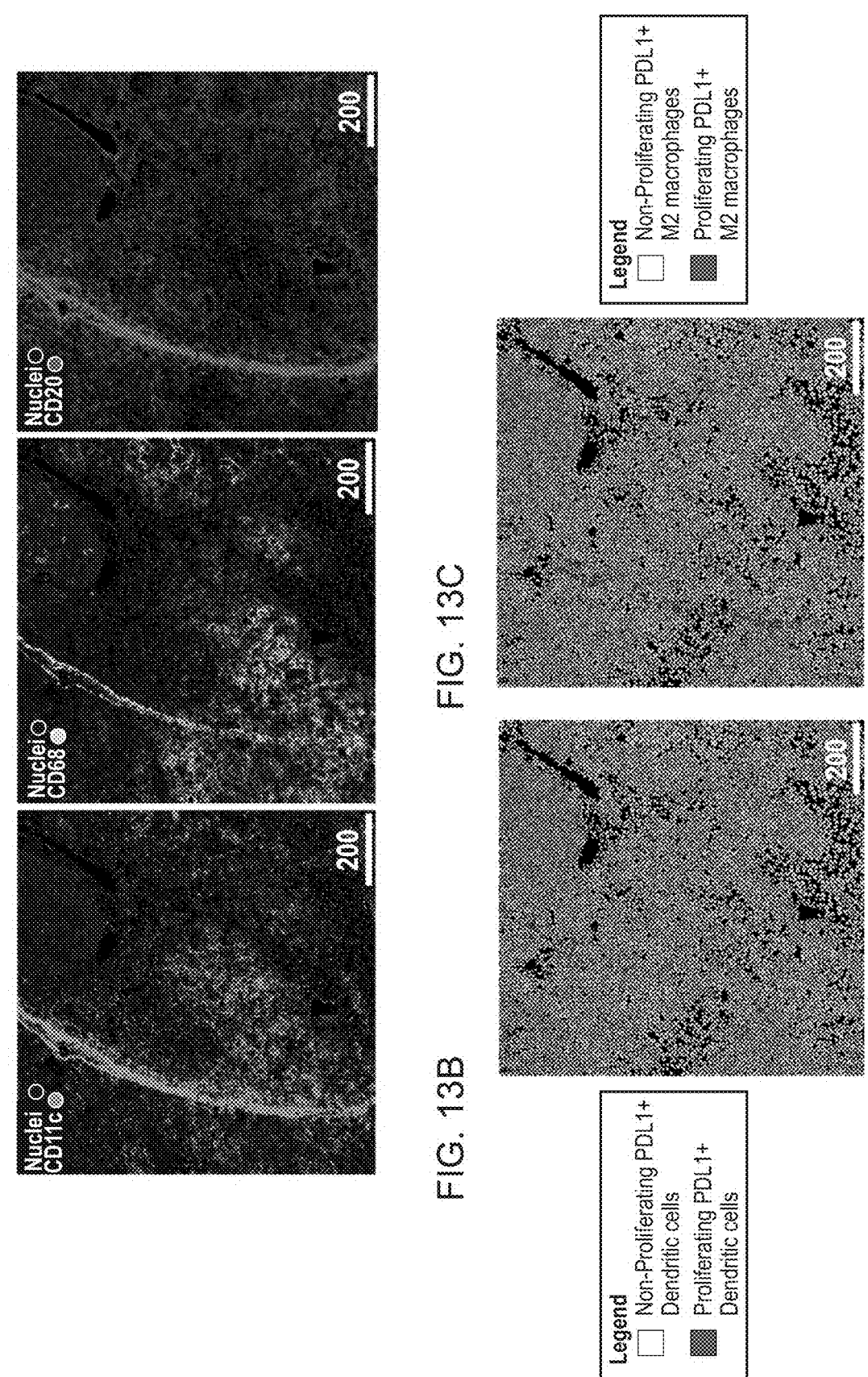

Mixed cell phenotype

B-Cells

Macrophages

Relative change after pre-processing (%)

PROCESSING MULTIPLEX IMAGES AND ANALYSIS OF IMMUNE ENRICHED SPATIAL PROTEOMIC DATA

CROSS-REFERENCE TO RELATED APPLICATION

The present application is a non-provisional application of and claims the benefit and priority under 35 U.S.C. 119 (e) of U.S. Provisional Application No. 63/562,886, filed on Mar. 8, 2024, the entire contents of which is incorporated herein by reference in its entirety for all purposes.

STATEMENT OF GOVERNMENT SUPPORT

This invention was made with government support under Grant No. CA245220 awarded by the National Institutes of Health (NIH). The government has certain rights in the invention.

FIELD

The present disclosure is directed generally to imaging processing, and in particular to techniques for removing artifact signals to improve image quality for data analysis.

BACKGROUND

High-throughput spatial imaging technologies involve advanced methodologies designed to concurrently detect and analyze multiple biomolecules or cellular components within tissue samples, while preserving their spatial context. These technologies are instrumental in unraveling the intricate organization and interactions of cells within tissues, offering valuable insights into various biological processes and disease mechanisms.

An example of high-throughput spatial imaging technologies is Imaging Mass Cytometry. Imaging mass cytometry operates on the principle of amalgamating mass spectrometry and metal tags to achieve the simultaneous detection of numerous proteins or markers in tissue sections at subcellular resolution. Utilizing antibodies labeled with stable isotopes, typically metal isotopes, imaging mass cytometry enables the targeted identification and quantification of specific biomolecules or cellular components through mass spectrometry. In a typical imaging mass cytometry workflow, tissue sections are prepared and treated with a panel of metal-conjugated antibodies, each designed to target a distinct protein or marker of interest. Subsequently, laser ablation is employed to analyze the tissue, where each laser pulse removes a small portion of the sample. The ablated material undergoes ionization, and the resulting ions are subjected to mass spectrometry analysis, revealing the presence and abundance of the labeled proteins.

Applications of high-throughput spatial imaging technologies span various domains, with significant contributions to cancer research, particularly in studying tumor microenvironments, heterogeneity, and immune cell interactions. In neuroscience, high-throughput spatial imaging has proven instrumental in investigating the molecular composition of brain tissues, aiding the understanding of neural circuits and neurodegenerative diseases. Furthermore, high-throughput spatial imaging finds application in immunology, enabling the detailed study of immune responses and the distribution of different immune cell types within tissues. In essence, these high-throughput spatial imaging technologies, exemplified by imaging mass cytometry, significantly contribute to advancing our comprehension of complex biological systems by providing detailed, multiplexed information while retaining the spatial context within tissues.

SUMMARY

Image processing techniques disclosed herein (e.g., a computer implemented method, system and operations thereof, and non-transitory computer-readable medium storing code or instructions executable by one or more processors) for removing artifact signals to improve image quality for data analysis.

Disclosed herein are techniques for removing artifact signals to improve image quality for data analysis. More specifically, these techniques encompass image pre-processing and a semi-supervised clustering for optimization and analysis of immune-enriched single-cell proteomics data generated via multiplexed imaging technologies. This is achieved through an image pre-processing pipeline (described herein as the IMClean pipeline), which converts image data contained in one type of file (e.g., .mcd) into another type of file (e.g., .tiff) and removes artifact signals from the image data using various algorithms to generate improved image data. Thereafter, a semi-supervised clustering pipeline (described herein as the IMmuneCite clustering pipeline) analyzes the improved image data using various techniques, including implementing a supervised algorithm to identify metaclusters such as general immune phenotypes (e.g., CD4–T-cells, Macrophages, Neutrophils, etc.) as well as non-immune phenotypes while implementing an unsupervised algorithm that enables the identification of specific subclusters and a more in-depth cellular status characterization. Advantageously, the image pre-processing pipeline facilitates downstream cell classification and identification of different cell phenotypes, while the semi-supervised clustering pipeline offers a robust and detailed description of the wide spectrum of clusters such as immune cell phenotypes associated with each tissue pathology in samples (e.g., human liver tissue). Lastly, described herein are algorithms and models that then extract a signal from the identified cell states (i.e., cellular status characterization from the semi-supervised clustering pipeline) and uses the signal to make a clinical prediction such as a prediction on a class of rejection (e.g., no rejection, T-cell mediated rejection, chronic rejection, etc.) for a transplant organ.

In various embodiments, a computer-implemented method is provided comprising: accessing an image file of a specimen stained with a panel of antibodies, wherein: the image file comprises regions of interest files of the specimen, the regions of interest files comprise individual signal files corresponding to each antibody in the panel of antibodies used to stain the specimen, and the individual signal files comprise artifact signals corresponding to background noise; performing an image pre-processing method to remove the artifact signals from the individual signal files, wherein the image pre-processing method comprises: performing an iterative process comprising: (a) applying, to a first individual signal file of the individual signal files from a first region on interest file of the regions of interest files using a denoising filter, a first denoising threshold value to generate a first noise signal and a second denoising threshold value to generate a second noise signal, (b) removing, from the first individual signal file, the first noise signal and the second noise signal to generate a denoised image, (c) comparing the first individual signal file to the denoised image to determine the performance quality of the denoising filter, and (d) choosing, based on the comparing, to: (i)

repeat steps (a)-(c) on the first individual file from the first region of interest file by modifying the first denoising threshold value and the second denoising threshold value, (ii) repeat steps (a)-(c) on the first individual signal file from a second or subsequent region of interest file of the regions of interest files, or (iii) ending the iterative process for the first individual signal file, and repeating the iterative process on a second or subsequent individual signal file of the individual signal files from the first region of interest to generate a set of denoised images for the specimen; and outputting the set of denoised images.

In some embodiments, the image file is obtained from imaging mass cytometry.

In some embodiments, (i) the panel of antibodies comprise two or more antibodies that recognize CD66b, CD20, CD28, CD16, CD163, CD11b, CD45, CD4, CD31, CD279, CD68, Foxp3, CK7, Ki-67, CD8a, Collagen Type I, CD3e, CD138, HLA-DR, Granzyme B, DNA1, DNA2, or any combination thereof, and (ii) the panel of antibodies are labeled with metal tags and wherein the metal tags comprise 139La, 142Nd, 144Nd, 146Nd, 147Sm, 149Sm, 152Sm, 153Eu, 154Sm, 156Gd, 159Tb, 160Gd, 164Dy, 167Er, 168Er, 169Tm, 170Er, 172Yb, 174Yb, 175Lu, 191Ir, 193Ir, or any combination thereof.

In some embodiments, the first denoising threshold value is a minimum filter value dependent upon the antibody panel and corresponding to a signal level below a designated minimum threshold, and the second denoising threshold value is a uniform filter value used to average pixel intensities, and (i) the minimum filter value is set to a desired integer and the uniform threshold value is set to null, (ii) the minimum filter value is set to a null value and the uniform threshold value is set to a desired integer value, (iii) the minimum filter value is set to a desired integer and the uniform threshold value is set to a desired integer value, or (iv) the minimum filter value is set to a null value and the uniform threshold value is set to a null value.

In some embodiments, repeating steps (a)-(c) on the first individual file from the second or subsequent regions of interest files comprises: (i) applying the first denoising threshold value and the second denoising threshold value to all the first individual files in the second or subsequent regions of interest files, (ii) applying new minimum threshold values and uniform threshold values to each of the first individual signal files in the second or subsequent regions of interest files, or (iii) a combination of (i) and (ii).

In some embodiments, the image pre-processing further comprises: performing another iterative process starting with a first denoised image from the set of denoised images, (e) processing the first denoised image using a spillover correction filter to generate a spillover corrected image, (f) processing the spillover corrected image using an aggregate removal filter to generate an aggregate removal image, and (g) repeating steps (e) and (f) for a second or subsequent denoised image from the set of denoised images to generate a set of stacked images comprising the aggregate removal images.

In some embodiments, the computer-implemented method further comprises performing downstream analysis on the set of stacked images, wherein the downstream analysis comprises: generating, by a cell segmentation tool using the set of stacked images, single-cell masks and a marker-expression matrix; generating, by a cell-phenotype identification pipeline using the single-cell masks and the marker-expression matrix, subclusters of cells based on their expression of lineage markers; generating, by an extraction algorithm using the expression of lineage markers associated with each subcluster of cells, a labeled dataset comprising a list the subclusters of cells and their corresponding expression patterns of the lineage markers; determining, by inputting the labeled dataset into a machine learning model, a clinical outcome based on the subclusters of cells.

In some embodiments, a system is provided that includes one or more processors, and a memory that is coupled to the one or more processors and stores a plurality of instructions which, when executed by the one or more processors, cause the one or more processors to perform any of the methods disclosed herein.

In some embodiments, a computer-program product is provided that is tangibly embodied in a non-transitory computer-readable memory that includes instructions which, when executed by the one or more processors, cause the one or more processors to perform any of the methods disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The figures are intended to illustrate certain embodiments and/or features of the compositions and methods, and to supplement any description(s) of the compositions and methods. The figures do not limit the scope of the compositions and methods, unless the written description expressly indicates that such is the case.

FIGS. 4A-4D show that the IMmuneCite clustering algorithm eliminates non-biologic marker clustering of different cell lineages. FIG. 4A is a heatmap showing clusters derived from the IMmuneCite clustering algorithm. The IMmuneCite clustering algorithm allows a granular identification of distinct cell phenotypes while eliminating the presence of clusters expressing markers from different cell lineages. FIG. 4B is a heatmap showing a FlowSOM-based unsupervised clustering including 19 markers used to identify different immune cell subpopulations and structural components. The resulting FlowSOM clusters show association of markers from different immune cell lineages which can confound and make phenotype assignment more difficult. Non-biological cell population are highlighted in red. FIG. 4C is a heatmap showing a Phenograph-based unsupervised clustering including 19 markers used to identify different immune cell subpopulations and structural components. A lower number of different clusters was identified via Phenograph compared to IMmuneCite (FIG. 4A) and FlowSOM (FIG. 4B), reducing the possibility of a detailed description of different cell subpopulations, while still presenting clusters with non-biological marker association (colored boxes). FIG. 4D. shows t-SNE plots showing differences in metacluster density and distribution in raw vs IMClean-processed for NR and CR samples.

FIGS. 5A-5E show that optimization of IMClean pre-processing allows removal of image artifacts and downstream identification of non-biological immune cell phenotypes. FIG. 5A. shows CD68 and FoxP3 raw signal after IMClean application and optimization. Also shown is an overlay of the optimized signals demonstrating enhanced true signal. FIG. 5B shows original CD68 and FoxP3 signals, while FIG. 5C shows their signals prior to IMClean optimization with spillover of CD68 in FoxP3 (white circle), noise, and aggregates still visible. FIG. 5D. shows a heatmap displaying two clusters for FoxP3+ macrophages as a result of image artifacts still present in the signal. FIG. 5E. shows an example of a too aggressive image pre-processing which eliminates some true signal, especially in CD68.

FIGS. 6A-6F show that the IMmuneCite workflow facilitates and improves phenotyping of immune cells within immune enriched human liver tissue. FIG. 6A illustrates an example of representative CR liver tissue section showing raw signal and IMClean-processed signal; IMClean enhances the identification of CD4+ T-cells, CD8+ T-cells, and macrophages compared to the same raw signal image as shown in the corresponding cell masks (Scale bar unit=μm). FIG. 6B. shows t-SNE plots showing differences in metacluster density and distribution in raw vs IMClean-processed TCMR data. FIG. 6C. shows the relative change in cell percentage within each metacluster before and after image pre-processing; IMClean increased the number of macrophages, plasma cells, neutrophils, and hepatocytes identified in the human liver rejection IMC dataset. FIG. 6D. shows that IMClean reduces non-specific marker signal while enhancing the specific ones within the appropriate cell types. The circle size indicates the positive marker percentage in a particular phenotype, and the circle color indicates the relative change of the positive rate for a particular marker after pre-processing. FIG. 6E. shows that IMClean pre-processing increases the specificity of the immune metacluster phenotyping; in relation to each marker, the ratios of specific metaclusters expressing a certain marker increase while the ratios of non-specific phenotypes for a particular marker decrease, thus showing a biologically appropriate correlation between markers and assigned metacluster. The relative change is defined as the difference in percentage composition of each cell type between IMClean-processed and raw data. FIG. 6F. shows that IMClean reduces the frequency of cells showing mixed phenotypes—cells that express markers belonging to different cell lineages (e.g. CD20 and CD8, or CD68 and CD4)—thus decreasing the rate of non-biological immune phenotypes.

FIGS. 7A-7E show that the IMmuneCite workflow enhances T lymphocyte subcluster identification and provides details on cell activation states. FIG. 7A shows that IMClean pre-processing increases the specificity of the immune subcluster phenotyping; for each marker, the ratio of each specific subcluster increases while those of non-specific phenotypes decrease, making cell phenotype and expressed markers biologically appropriate. For example: after IMClean pre-processing, ratio of cells with a positive PD1 expression was increased in CD4+ and CD8+ T-cell subclusters while a negative (decrease) ratio of PD1 positive cells was observed in non-T and B-cell subclusters (Subclusters 12-35=12: M1 macrophages; 13: M2 macrophages; 14: Proliferating M1 macrophages, 15: Proliferating M2 macrophages; 16: CD16+ M1 macrophages; 17: CD16+ M2 macrophages; 18: HLADR+ M2 macrophages; 19: Classical monocytes; 20: Intermediate monocytes; 21: Activated monocytes; 22: B cells; 23: Proliferating B cells; 24: PD1+ B cells; 25: Neutrophils; 26: Plasma cells; 27: Cholangiocytes; 28: Proliferating Cholangiocytes; 29: HLADR+ Cholangiocytes; 30: Endothelial cells; 31: Proliferating Endothelial cells; 32: HLADR+ Endothelial cells, 33: Hepatocytes; 34: Proliferating Hepatocytes; 35: HLADR+ Hepatocytes). FIG. 7B. shows a representative zoomed-in liver tissue section highlighting CD4+ T-cells colored by cell subpopulation (see color key legend). Among the subpopulations identified via unsupervised clustering within the CD4+ T-cell metacluster in both the raw and preprocessed datasets, eight emerged to be common to both datasets: Resident Memory CD4+ T-cells, CD3+CD4+ T-cells, Activated (HLADRhi) CD4+ T-cells, CD16+CD4+ T-cells, Naïve CD4+ T-cells, HLADR+CD4+ Tregs, HLADR-CD4+ Tregs, and PD1+CD4+ T-cells. FIG. 7C. shows a representative zoomed-in liver tissue section highlighting the CD8+ compartment (see color key legend); after using unsupervised clustering algorithm, three CD8+ T-cell subclusters were identified to have the same expression patterns in both the raw and the IMClean-processed datasets (CD3+CD8+ T-cells, Proliferating (Ki67+) T-cells, and PD1+CD28+ T-cells) for which marker expressions were compared before and after IMClean pre-processing (as show in A). FIG. 7D. shows the comparison of marker expression between raw and IMClean-processed T-cell subclusters showed that IMClean reduces non-specific marker signal while enhancing the specific ones within cell types. The circle size indicates the positive marker percentage in a particular phenotype, and the circle color indicates the relative change of the positive rate for a particular marker after pre-processing. FIG. 7E. displays the median fold change of marker expression between raw and IMClean-processed for CD4+ T-cell subclusters.

FIGS. 8A-8E show a comparison of CD4+ and CD8+ T-cell subpopulations identified in the raw dataset vs the dataset processed following the IMmuneCite workflow. FIG. 8A shows heatmaps illustrating CD4+ T-cell subpopulations identified via unsupervised clustering within the CD4+ T-cell metacluster using the expression values from specific markers—CD28, CD16, CD11b, CD45, CD4, PD1, FoxP3, Ki67, CD3, and HLADR—within both the raw and IMClean-processed datasets. This approach identified eight subpopulations in the raw IMC data vs nine in the pre-processed IMC data; it was not possible to identify a proliferating CD4+ T-cell population in the raw data. FIG. 8B. shows that the percentage of each CD4+ T-cell subcluster was compared between the two datasets; IMClean allowed for a greater identification of resident memory and CD3+CD4+ T-cells. FIG. 8C. shows heatmaps illustrating CD8+ T-cell subclusters identified via unsupervised clustering within the CD8+ T-cell compartment using selected markers—CD28, CD16, CD11b, CD45, CD3, CD8, GranzymeB, PD1, FoxP3, Ki67, and HLADR—in both the raw and IMClean-processed single-cell datasets. This approach identified 4 distinct subclusters in the raw data and 5 distinct subclusters in the pre-processed data. Three subclusters shared the same marker expression pattern, CD3+CD8+ T-cell, Proliferating (Ki67+) CD8+ T-cells, and PD1+ CD28+CD8+ T-cells. FIG. 8D. shows boxplots showing comparison of CD8+ subpopulations as a percentage of cells per patient (Kruskal-Wallis test). There were no differences in CD8+ T-cell subsets shared between the two datasets. FIG. 8E. shows that the median fold change of marker expression in the CD8+ T-cell compartment between raw and IMClean-processed data.

FIGS. 9A-9H show that the IMmuneCite workflow enables an accurate phenotyping and depiction of cellular states of Monocyte, Macrophage and B cell subclusters. FIG. 9A shows that IMClean pre-processing increases the specificity of subcluster phenotyping within the monocyte, macrophage, and B cell compartments; given a certain positive marker, the ratio of each specific subcluster (for that marker) increases while that of non-specific phenotypes decreases, making cell phenotype and expressed markers biologically appropriate. For example: after IMClean pre-processing, ratio of cells with a positive CD68 expression was increased only in macrophage subclusters while a negative (decrease) ratio of CD68 positive cells was observed in T and B-cell subclusters (Subclusters 14-35=14: CD3+ CD4+ T-cells; 15: Resident memory CD4+ T-cells; 16: HLADR+ CD4+ Tregs; 17: HLADR− CD4+ Tregs; 18: Naïve CD4+ T-cells; 19: PD1+ CD4+ T-cells; 20: Activated CD4+ T-cells; 21: CD16+ CD4+ T-cells; 22: CD3+ CD8+ T-cells; 23: Proliferating CD8+ T-cells; 24: PD1+ CD28+ CD8+ T-cells; 25: Neutrophils; 26: Plasma cells; B cells; 23: Proliferating B cells; 24: PD1+ B cells; 25: Neutrophils; 26: Plasma cells; 27: Cholangiocytes; 28: Proliferating Cholangiocytes; 29: HLADR+ Cholangiocytes; 30: Endothelial cells; 31: Proliferating Endothelial cells; 32: HLADR+

Endothelial cells, 33: Hepatocytes; 34: Proliferating Hepatocytes; 35: HLADR+ Hepatocytes). FIG. 9B. shows a representative zoomed-in liver tissue section highlighting macrophages colored by cell subpopulation (see color key legend). Subpopulations were identified via unsupervised clustering within the macrophage metacluster in both raw and pre-processed datasets. Seven distinct subpopulations emerged to be common between the two datasets: M1 and M2 populations, Proliferating (Ki67+) M1 macrophages, Proliferating (Ki67+) M2 macrophages, CD16+ M1 macrophages, CD16+ M2 macrophages, and HLADR+ M2 macrophages. FIG. 9C. shows a representative zoomed-in liver tissue section highlighting monocyte subpopulations (see color key legend); after unsupervised clustering applied to both datasets, three subpopulations were identified to have the same expression patterns in both the raw and the IMClean-processed datasets: Classical monocytes (CD11b+), Intermediate (CD16+CD68+CD163+) monocytes and Activated (HLADRhigh) monocytes. FIG. 9D. shows a representative zoomed-in liver tissue section showing B-cell subclusters identified via unsupervised clustering in both raw and IMClean-processed datasets, which shared the following B-cell subpopulations: B cells (CD45+CD20+ HLADR+), PD1+ B cells (CD45+CD20+HLADR+PD1+), and proliferating B cells (CD45+CD20+HLADR+Ki67+). FIG. 9E. shows the comparison of marker expressions between raw and IMClean-processed for monocyte, macrophage, and B cell subclusters showed that IMClean reduces non-specific marker signal while enhancing the specific ones within cell types. The circle size indicates the positive marker percentage in a particular phenotype, and the circle color indicates the relative change of the positive rate for a particular marker after pre-processing. FIGS. 9F-H. displays the median fold change of marker expression between raw and IMClean-processed for macrophage, monocyte, and B cell subclusters, respectively.

FIGS. 10A-10F show the comparison of macrophage, monocyte, and B cell subpopulations identified in the raw dataset vs the dataset processed following the IMmuneCite workflow. FIG. 10A are heatmaps showing macrophage subpopulations identified via unsupervised clustering using the expression values from select markers—HLADR, CD68, CD163, CD16, Ki67, CD45, CD11b, and FoxP3—in raw vs pre-processed single-cell datasets. Seven and nine distinct subclusters were identified in the raw vs IMClean-processed datasets, respectively. FIG. 10B. are boxplots of macrophage subclusters of raw vs pre-processed data. A different distribution was observed between the two datasets for M1 and M2 macrophages as well as CD16+ M1 and M2 macrophages. FIG. 10C. are heatmaps showing monocyte subpopulations identified via unsupervised clustering using specified markers—CD16, CD11b, CD45, CD68, CD163, HLADR, FoxP3, and Ki67—in raw vs pre-processed single-cell datasets. This approach identified 4 distinct subclusters in the raw data and 4 distinct subclusters in the pre-processed data, with similar expression profiles in 3 out 4 subclusters: Classical monocytes (CD11b+), Intermediate monocytes (CD11b+ CD68+ CD163+ CD16+ HLADR+), and Activated monocytes (HLADR+ CD11b+). FIG. 10D. are boxplots showing the comparison of monocyte subclusters as a percentage of cells per patient (Kruskal-Wallis test). A greater percentage of classical monocytes was identified in IMClean-processed data. FIG. 10E. are heatmaps showing B cell subpopulations identified via unsupervised clustering using the expression values from select markers— HLADR, CD20, Ki67, CD45, PD1, and FoxP3—in raw vs pre-processed single-cell datasets. B-cell subclusters identified in both datasets presented the same expression patterns which led to the identification of a generic B-cell subpopulation (CD20+ CD45+HLADR+), PD1+ (CD20+ CD45+ HLADR+) B-cells, and Proliferating (Ki67+CD20+ CD45+ HLADR+) B-cells. FIG. 10F. are boxplots comparing distribution of B cell subclusters between the two datasets with no differences in cell proportion observed.

FIGS. 12A-12F illustrate validation of the IMmuneCite workflow in IMC data from murine HCC tissue demonstrates an enhancement in the quality of data in structurally complex immune enriched tissues. FIG. 12A are heatmaps showing scaled marker expression within the 10 metaclusters identified in both raw and IMClean-processed external IMC mouse data, with grey bars indicating the total number of cells per cell type. FIG. 12B. shows t-SNE plots comparing raw and pre-processed data showing different density and distribution of cell metaclusters in raw vs IMClean-processed data. FIG. 12C. shows the relative change in cell percentage within each metacluster before and after image pre-processing; IMClean increased the number of macrophages, myofibroblasts, dendritic cells, and epithelial cells identified after image pre-processing. FIG. 12D. shows that within each metacluster, IMClean reduces non-specific marker signal while enhancing the specific ones for a particular cell phenotype. The circle size indicates the positive marker percentage in a particular phenotype, and the circle color indicates the relative change of the positive rate for a particular marker after pre-processing. FIG. 12E. shows that IMClean pre-processing increases the specificity of the metacluster phenotyping; in relation to each marker, the ratios of specific metaclusters expressing a certain marker increase while the ratios of non-specific phenotypes for a particular marker decrease, thus showing a biologically appropriate correlation between markers and assigned metacluster. Relative percentage change was computed as positive cell (%) in the IMClean-processed data minus positive cell (%) in raw data divided by the total number of cells in the raw data. FIG. 12F. is a representative tissue section showing the spatial location of the ten identified metaclusters, which highlights structural components and infiltrating immune cells within mouse HCC tissue (Scale bar unit=μm).

FIGS. 13A-13E show that IMmuneCite workflow allows detection of image artifacts and exclusion of false data as proven in mouse HCC IMC data. FIG. 13A is an example of raw signal from CD11c, CD68, and CD29 highly co-expressed in a specific area of the tissue corresponding to a wrinkle artifact in the tissue staining. The high expression of all the markers was noted in the above tissue section as well as in some other samples. FIGS. 13B and 13C show that the cells detected in those areas were classified by the IMmuneCite clustering algorithm as either proliferating PDL1 dendritic cells (FIG. 13B) or proliferating PDL1 M2 macrophages (FIG. 13C); these expression profiles were not specific for their main cell lineages. Those cells were visualized on the tissue (as shown in FIG. 13B and FIG. 13C) and proven to all be located in the same area corresponding to the artifacts in FIG. 13A. Those cells were thus excluded from the analysis. FIG. 13D. shows that IMClean reduces the frequency of cells showing mixed phenotypes—cells that express markers belonging to different cell lineages (e.g. CD20 and CD8, or CD20 and CD4/CD8)—thus decreasing the rate of non-biological immune phenotypes. FIG. 13E displays cell percentages for each immune subcluster were compared between raw and IMClean-processed mouse IMC data.

FIG. 14A is a heatmap showing 25 immune clusters identified in raw imaging mass cytometry data obtained from mouse HCC mouse models. FIG. 14B shows 24 immune clusters identified in the same mouse HCC imaging mass cytometry dataset after IMClean pre-processing.

FIGS. 15A-15G show that the IMmuneCite workflow allows a discrete phenotyping of lymphocytes in mouse HCC models. FIG. 15A illustrates that assessment of IMC data from HCC mouse models showed that the IMmuneCite workflow increases the specificity of CD4+ and CD8+ T-cell subcluster phenotyping; for each marker, the ratio of specific subclusters with positive expression increases while the ratio of non-marker specific phenotypes decreases. FIG. 15B. shows the comparison of marker expression between raw and IMClean-processed for CD4+ and CD8+ T-cells showed that pre-processing reduces the non-specific marker signal while the specific ones are enriched in their respective cell types. The circle size indicates the positive marker percentage in a particular phenotype, and the circle color indicates the relative change of the positive rate for a particular marker after pre-processing. FIG. 15C. is a representative zoomed-in of mouse HCC liver tissue section highlighting CD4+ T-cells colored by cell subpopulation (see color key legend). Subpopulations identified via unsupervised clustering within the CD4+ T-cell metacluster in both the raw and processed datasets are CD3+ CD4+ T-cells, PD1+ (PD1+ CD3+) CD4+ T-cells, CD4+ (CD161+ Granzyme B+ CD3+) NKT cell, and CD4+ (CD3+ FoxP3+) Tregs. FIG. 15D. is a representative zoomed-in mouse HCC liver tissue section highlighting CD8+ T-cell compartment (see color key legend); after using unsupervised clustering algorithm, four CD8+ T-cell subclusters were identified to have the same expression patterns in both the raw and the IMClean-processed datasets: CD3+CD8+ T-cells, Proliferating (Ki67+) T-cells, and PD1+ (CD3+) CD8+ T-cells, and Cytotoxic (Granzyme B+ CD3+ CD8+) T-cell. FIG. 15E. illustrates that in the B cell compartment, IMClean increases the specificity of subcluster phenotyping; the ratio of specific subclusters with positive scaled expression for a certain marker increases while the ratio of non-specific subclusters decreases. FIG. 15F. shows the comparison of marker expressions between raw and IMClean-processed in B cell subclusters showed that IMClean reduces non-specific marker signal while enhancing the specific ones within cell types. The circle size indicates the positive marker percentage in a particular phenotype, and the circle color indicates the relative change of the positive rate for a particular marker after pre-processing. FIG. 15G. is a representative case showing spatial distribution of B cell subclusters within mouse HCC tissue section including generic B cells (CD45+ B220+), Proliferating (Ki67+ CD45+) B cells, and PDL1+ (CD45+) B cells.

FIGS. 16A and 16B illustrates that the IMmuneCite workflow ameliorates both specificity (FIG. 16A) and sensitivity (FIG. 16B) of macrophage sub-phenotyping; for a certain marker with a positive scaled expression, the ratios of specific subclusters increase while the ratios of non-specific subclusters decrease, as shown in FIG. 16A. For each macrophage subcluster, processing reduces the non-specific marker signal while the specific ones are enriched (FIG. 16B). The circle size indicates the positive marker percentage in a particular phenotype, and the circle color indicates the relative change of the positive rate for a particular marker after IMClean pre-processing. FIG. 16C. is a representative zoomed-in mouse HCC liver tissue section highlighting macrophages colored by cell subpopulation (see color key legend). Subpopulations commonly identified via unsupervised clustering within macrophage compartments in both the raw and processed datasets are M1 macrophages (CD45+ F480+ CD68+), M2 macrophages (CD206+ CD68+ F480+), Proliferating PDL1+ macrophages (CD45+ PDL1+ MHCII+ CD68+ F480+) and CD86+ M1 (CD45+ MHCII+ CD68+ F480+) macrophages, S100A9+ M1 (CD45+ CD68+ F480+) macrophages, and S100A9 (CD206+ F480+) M2 macrophages. FIGS. 16D and 16E. show that IMClean increases the specificity and sensitivity of dendritic cell subcluster phenotyping; the ratios of specific subclusters with positive scaled expression for a certain marker increase (FIG. 16D). Comparison of marker expressions between raw and IMClean-processed for dendritic cell subclusters showed that IMClean enhances the specific marker signal within cell types. The circle size indicates the positive marker percentage in a particular phenotype, and the circle color indicates the relative change of the positive rate for a particular marker after pre-processing. FIG. 16F. is a representative case showing spatial distribution of dendritic cell subclusters commonly identified in both datasets in mouse HCC tissue section including Dendritic cells (CD11c+) and PDL1+ (CD45+ CD86+ MHCII+ CD11c+) Dendritic cells (see color key legend).

DETAILED DESCRIPTION

Introduction

Figure 1:
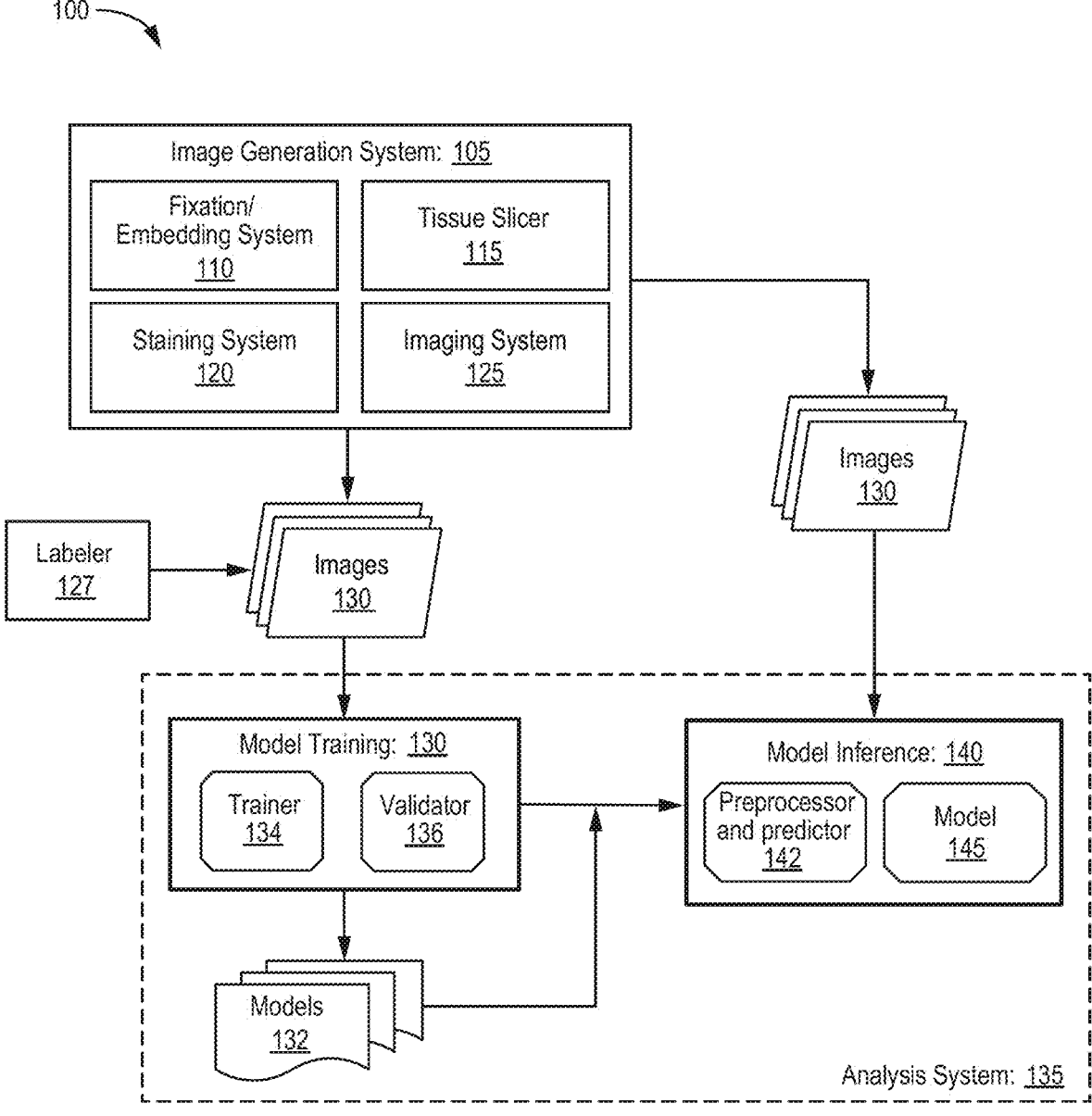
FIG. 1 shows an exemplary computing system for generating a representative dataset for training and using a machine-learning model in accordance with various embodiments.

High-throughput spatial imaging technologies, including Imaging Mass Cytometry and Multiplexed Ion Beam Imaging Technology (MIBI), allow quantification of protein expression at single-cell resolution alongside robust analysis of spatial interactions due to the preservation of native tissue architecture. These imaging platforms have been used to characterize immune microenvironments associated with tumor biology, infectious processes, and inflammatory diseases through simultaneous detection of more than 40 protein antigens. Data generated by this technology is comprised of a set of images, one for each measured metal ion channel, which are then analyzed using different computational biology algorithms.

Although spatial proteomics represent a powerful technology with growing use in biomarker discovery and therapeutic monitoring, its widespread adoption has been hampered by two major challenges: (i) the presence of images artifacts which can deteriorate the quality of data and (ii) the choice of computational approaches to perform cell segmentation and assign cell phenotypes. This is particularly relevant when examining immune microenvironments within tissue sections, where many different cell types, each with multiple phenotypic markers, coexist within an inflammatory lesion.

To the first point, image artifacts (e.g., background noise, channel cross talk, and antibody aggregation) impair the quality of the data and impend downstream analysis of the images, specifically in spatial proteomics analysis. While imaging mass cytometry is not affected by autofluorescence, which is typical of fluorophore-based technologies, a certain amount of signal spillover (or channel crosstalk), is still present and represents a source of background noise which can affect experimental results. Channel crosstalk is mainly due to metal isotopic impurity, oxide formation, and abundance sensitivity and can be only partially addressed by a careful design of the antibody panel and selection of highly pure metal isotopes used for antibody conjugation. Additional sources of noise can be related to non-specific antibody binding, ion counting imaging-based technology, antibody concentration and tissue quality. Lastly, image artifacts can be presented as hot pixels, which may be derived from the deposition on the tissue of antibodies aggregates that are not related to any biological structure but cause areas with high ions counts which may lead to a false positive interpretation of that signal. Thus, overcoming these image artifacts remains an important step in data preprocessing to ensure a biologically valid conclusion.

Several methods have been developed to address image artifacts and pre-processing in spatial proteomics experiments. Some allow for spillover correction only, as in the case of the R-based package called CATALYST. A semi-automated Ilastik-based method, and more recently, the imaging mass cytometry-Denoise pipeline, based on the self-supervised deep learning-based shot noise imagining filtering (DeepSNiF) algorithm, were both developed to correct for technical and sample-specific noise. Imaging mass cytometry-Denoise also allows for hot pixel removal by applying differential intensity map-based restoration (DIMR). Conversely, in most cases, correction of only hot pixels has been performed by using thresholding methods. More recently, SPEX (Spatial Expression Explorer) a modular and customizable pipeline, allows for channel spillover correction and denoising by applying global background correction, median filter denoising and non-local means (NLM) denoising. Currently, only MAUI (MBI Analysis User Interface), a MATLAB based user friendly interface pipeline enables correction of all three types of image artifacts, channel crosstalk, noise, and hot pixel. Together, these analytic tools can overcome challenges related to image pre-processing in spatial proteomics. However, data formatting challenges across multiple platforms, some of which are not free and open source (e.g. MATLAB), advanced bioinformatics expertise across each of these platforms, and the need for deep knowledge of normal and abnormal tissue architecture, pathophysiology, and immunology, make these software cumbersome to apply to studies examining the immune microenvironment.

After pre-processing imaging mass cytometry data, the assignment of cell phenotypes (identification and classification) remains one of the most challenging tasks in spatial proteomics, particularly when studying the immune microenvironment. This is due to close proximity of cells which can cause lateral spillover of the signal from one object into another, especially in areas with dense immune infiltrates, where the cell-to-cell interaction creates physical overlap of cell membranes and cytoplasm, or where the overlapping of cell fragments can create a mismatch of nuclear signals and membranes. Additionally, irregular cell shapes (e.g., macrophages, dendritic cells) represent another cause of lateral signal spillover from one cell mask into an adjacent cell mask. This can result in non-biological co-expression patterns (e.g., CD4/CD68, CD3/CD20, CD66/CD4) which lead to the identification of implausible immune cell phenotypes. Correction of lateral spillover was attempted with the development of RedDSEA, a MATLAB-based algorithm. However, it has a limited ability to correct for lateral spillover in the case of multiple overlapping cells, is unable to perform cell clustering, and its performance depends on quality of image segmentation.

Currently, cell phenotyping of pre-processed single cell datasets generated from spatial proteomics relies on either unsupervised or supervised clustering methods. Unsupervised clustering approaches (e.g. FlowSOM, Phenograph, Gaussian mixture model) require manual annotation of each identified cluster, which comes with the arbitrary assignment of phenotype, including those with confounding markers expression patterns. Supervised algorithms require a priori knowledge of marker expressions or the creation of a ground-truth dataset, thus limiting both the identification of novel or rare cell phenotypes and an in-depth characterization of cell status. Additionally, these algorithms have been developed for cell suspension assays such as single-cell RNA sequencing (scRNA-seq), flow cytometry, and Cytometry by Time-Of-Flight (CyTOF), which lack the cell-to-cell spatial interaction component and are not affected by lateral spillover. Overall, few algorithms have been specifically designed for cell classification in spatial proteomics assays, with none being immune-focused.

To address these challenges and limitations, techniques disclosed herein describe an image pre-processing workflow for removing artifact signals from imaging data, thus providing improved and higher quality "clean" images for downstream analysis. This method comprises accessing an image file of a specimen stained with a panel of antibodies, wherein the image file comprises regions of interest files of the specimen, the regions of interest files comprise individual signal files corresponding to each antibody in the panel of antibodies used to stain the specimen, and the individual signal files comprise artifact signals corresponding to background noise; applying, to the individual signal files for each region of interest, a denoising filter to remove the artifact signals, wherein the denoising filter removes artifact signals by: in an iterative process starting with a first individual signal file from a first region of interest of the image file, (a) inputting, into the denoising filter, the first individual signal file, and denoising threshold values, (b) applying, to the first individual signal file, a first denoising threshold value to generate a first noise signal, (c) applying, to the first individual signal file, a second denoising threshold value to generate a second noise signal, (d) removing, from the first individual signal file, the first noise signal and the second noise signal to generate a denoised image, (e) comparing the first individual signal file to the denoised image, and (f) choosing to either (i) repeat steps (a)-(e) on the first individual file from the first region of interest file by updating the minimum threshold value and the uniform threshold value, (ii) repeat steps (a)-(e) on the first individual file from a second or subsequent region of interest files of the specimen from the image file, or (iii) finalizing the iterative process; repeating the iterative process on a second or subsequent individual signal files from the first region of interest to generate a set of denoised images for the specimen; and outputting the set of denoised images to be used for downstream analysis.

Moreover, the techniques described herein may be part of a larger workflow that encompasses the image pre-processing workflow described above in combination with cell segmentation, a semi-supervised clustering algorithm, a cell state signal extraction algorithm or model, or any combination thereof for optimization and analysis of immune-enriched single-cell proteomics data generated via multiplexed imaging technologies. For example, in one particular aspects, the computer-implemented method comprises accessing an image file of a specimen stained with a panel of antibodies, wherein: the image file comprises regions of interest files of the specimen, the regions of interest files comprise individual signal files corresponding to each antibody in the panel of antibodies used to stain the specimen, and the individual signal files comprise artifact signals; performing, to the region of interest files, an image pre-processing method to remove the artifact signals from the individual signal files, wherein the image pre-processing method comprises: in an iterative process starting with a first individual signal file from a first region of interest of the image file, (a) processing the first individual signal file using a first artifact filter, wherein the first output of the first artifact filter corresponds to a spillover corrected image, (b) processing the spillover corrected image using a second artifact filter, wherein the second output of the second artifact filter corresponds to a denoised image, (c) processing the denoised image using a third artifact filter, wherein the third output of the third artifact filter corresponds to an aggregate removal image, and (d) repeating steps (a)-(c) for the first individual signal file from a second or subsequent regions of interest file; repeating the iterative process on a second or subsequent individual signal file from the first region of interest file of the image file to generate a set of stacked images, wherein the stack of images comprise the aggregate removal images from each of the regions of interest files; inputting, into a cell segmentation tool, the set of stacked images to obtain single-cell masks and a marker-expression matrix; inputting, into a cell-phenotype identification pipeline, the single-cell masks and the marker-expression matrix, wherein the cell-phenotype identification pipeline comprises a clustering algorithm and an unsupervised clustering algorithm; and outputting, from the cell-phenotype identification pipeline, subclusters of cells for visualization and downstream analysis.

As used herein, the terms "about," "similarly," "substantially," and "approximately" are defined as being largely but not necessarily wholly what is specified (and include wholly what is specified) as understood by one of ordinary skill in the art. In any disclosed embodiment, the term "about," "similarly," "substantially," or "approximately" may be substituted with "within [a percentage] of" what is specified, where the percentage includes 0.1 percent, 1 percent, 5 percent, and 10 percent, etc.

As used herein, when an action is "based on" something, this means the action can be based at least in part on at least a part of the something.

Generating Image Dataset for Training and Using a Machine Learning Model

FIG. 1 shows an exemplary system 100 for generating images for training and using a machine-learning model. Images are generated at an image generation system 105. The images may be biomedical images, such as histopathological images, computed tomography (CT) images, magnetic resonance imaging (MRI) images, ultrasound images, high-throughput spatial imaging technologies such as Imaging Mass Cytometry, or any other suitable biomedical images. The images may be of a specimen, e.g., a biological sample, obtained from a patient. The specimen can be a cell-containing liquid or a tissue. The specimen can comprise, but is not limited to, amniotic fluid, tissue biopsies, blood, blood cells, bone marrow, fine needle biopsy samples, peritoneal fluid, amniotic fluid, plasma, pleural fluid, saliva, semen, serum, tissue or tissue homogenates, frozen or paraffin sections of tissue. Methods of obtaining a specimen include but are not limited to biofilms, aspirations, tissue sections, swabs, drawing blood or other fluids, surgical or needle biopsies, and the like. The specimen can be obtained from a healthy subject, a subject with a disease, a subject who received an organ transplant, or a subject rejecting an organ transplant.

As described herein, "patient," and "subject" are used interchangeably and refer to any single animal, more preferably a mammal (including humans and non-human animals such as dogs, cats, horses, rabbits, rats, cows, pigs, sheep, and non-human primates). Thus, the methods described herein are applicable to both human and veterinary disease. In certain embodiments, subjects are "patients," i.e., living humans that are receiving medical care for a disease or condition. This includes persons with no defined illness who are being investigated for signs of pathology. Patients may have received an organ transplant and are being monitored for signs of transplant rejection. In other cases, the patient received an organ transplant and is rejecting the organ. Transplant rejection may include functional and structural deterioration of the tissue/organ due to an active immune response expressed by the recipient, and independent of non-immunologic causes of organ dysfunction. Acute transplant rejection can result from the activation of recipient's T cells and/or B cells; the rejection primarily due to T cells is classified as T cell mediated acute rejection (TCMR) (also known as acute cellular rejection (ACR)) and the rejection in which B cells are primarily responsible is classified as antibody mediated acute rejection (ABMR). Examples of tissues and/or organs that may be transplanted, without limitation, include liver, heart, lungs, kidney, stomach, intestine, trachea, cornea, bone, tendon, skin, pancreas, heart valves, nerves, or vascular tissue.

In other instances, the subject may have a disease or condition. One skilled in the art would also recognize that terms such as "disease", "disorder", "condition", "morbidity", "sickness", "illness", or the like may be used interchangeably. A disease is an abnormal condition that adversely affects the structure or function of all, substantially all, or part of an organism and is not immediately due to any external injury. In other words, a disease is a condition that impairs normal functioning of the body. Diseases may also be known as medical conditions that are associated with signs or symptoms that can be either known or unknown to the disease. A disease may be an infectious disease, a deficiency disease, a hereditary disease (e.g., including both genetic (mutation(s) or de novo) and non-genetic (asthma, multiple sclerosis, Chron's, IBD, etc.) hereditary diseases), and physiological diseases. An infectious disease (e.g., infection by a pathogen) may include, without limitation, infection by viruses, bacteria, fungi, protozoa, multicellular organisms, and aberrant proteins known as prions. Examples of disease, without limitation can include: neurodegenerative diseases (e.g., Alzheimer's disease and other dementias, Parkinson's disease (PD) and PD-related disorders, prion disease, motor neuron diseases, Huntington's disease, spinocerebellar ataxia, spinal muscular atrophy, etc.); cancer (bladder, breast, cervical, colorectal, gynecological, head and neck, kidney, liver, lung, mesothelioma, myeloma, prostate, skin, etc.); autoimmune (e.g., psoriasis, rheumatoid arthritis, multiple sclerosis, Type 1 diabetes, IBD, celiacs, lupus, etc.); and any other disease where a biological sample comprising cell-containing liquid or a tissue sample may be obtained.

For histopathological images, a fixation/embedding system 110 fixes and/or embeds a tissue sample (e.g., a sample from a transplanted organ) using a fixation agent (e.g., a liquid fixing agent, such as a formaldehyde solution) and/or an embedding substance (e.g., a histological wax, such as a paraffin wax and/or one or more resins, such as styrene or polyethylene). Each slice may be fixed by exposing the slice to a fixating agent for a predefined period of time (e.g., at least 3 hours) and by then dehydrating the slice (e.g., via exposure to an ethanol solution and/or a clearing intermediate agent). The embedding substance can infiltrate the slice when it is in liquid state (e.g., when heated).

A tissue slicer 115 then slices the fixed and/or embedded tissue sample (e.g., a sample from a transplanted organ) to obtain a series of sections, with each section having a thickness of, for example, 4-5 microns. Such sectioning can be performed by first chilling the sample and then slicing the sample in a warm water bath. The tissue can be sliced using (for example) a vibratome or compresstome.

Because the tissue sections and the cells within them are virtually transparent, preparation of the slides typically includes staining (e.g., automatically staining) the tissue sections in order to render relevant structures more visible. In some instances, the staining is performed manually. In some instances, the staining is performed semi-automatically or automatically using a staining system 120.

The staining can include exposing an individual section of the tissue to one or more different stains (e.g., consecutively or concurrently) to express different characteristics of the tissue. For example, each section may be exposed to a predefined volume of a staining agent for a predefined period of time. A duplex assay includes an approach where a slide is stained with two biomarker stains. A singleplex assay includes an approach where a slide is stained with a single biomarker stain. A multiplex assay includes an approach where a slide is stained with two or more biomarker stains.

One exemplary type of tissue staining is histochemical staining, which uses one or more chemical dyes (e.g., acidic dyes, basic dyes) to stain tissue structures. Histochemical staining may be used to indicate general aspects of tissue morphology and/or cell microanatomy (e.g., to distinguish cell nuclei from cytoplasm, to indicate lipid droplets, etc.). One example of a histochemical stain is hematoxylin and eosin (H&E). Other examples of histochemical stains include trichrome stains (e.g., Masson's Trichrome), Periodic Acid-Schiff (PAS), silver stains, and iron stains. The molecular weight of a histochemical staining reagent (e.g., dye) is typically about 500 kilodaltons (kD) or less, although some histochemical staining reagents (e.g., Alcian Blue, phosphomolybdic acid (PMA)) may have molecular weights of up to two or three thousand kD. One case of a high-molecular-weight histochemical staining reagent is alpha-amylase (about 55 kD), which may be used to indicate glycogen.

Another type of tissue staining is immunohistochemistry (IHC, also called "immunostaining"), which uses a primary antibody that binds specifically to the target antigen of interest (e.g., a biomarker, a cell lineage marker, a cell surface protein). IHC may be direct or indirect. In direct IHC, the primary antibody is directly conjugated to a label (e.g., a chromophore or fluorophore). In indirect IHC, the primary antibody is first bound to the target antigen, and then a secondary antibody that is conjugated with a label (e.g., a chromophore or fluorophore) is bound to the primary antibody. The molecular weights of IHC reagents are much higher than those of histochemical staining reagents, as the antibodies have molecular weights of about 150 kD or more.

The term "antibody" as used herein refers to an immunoglobulin (Ig) molecule, an antigen binding fragment thereof or a binding derivative thereof. An antigen binding fragment of an antibody contains an antigen binding site that specifically binds an antigen. The antibodies (Abs) may be monoclonal antibodies, polyclonal antibodies, or multi-specific antibodies (e.g., bispecific antibodies). Examples of antibodies include immunoglobulin (Ig) types IgG, IgD, IgE, IgA and IgM. The antibodies may be native antibodies or recombinant antibodies. The antibodies may be produced by host cells. The term antibody is not restricted to immunoglobulins derived from any particular mammalian species and includes murine, human, equine, and camelids antibodies (e.g., human antibodies). The term "antibody" encompasses antibodies isolatable from natural sources or from animals following immunization with an antigen as well as engineered antibodies including monoclonal antibodies, bis-pecific antibodies, tri-specific, chimeric antibodies, humanized antibodies, human antibodies, CDR-grafted, veneered, or deimmunized (e.g., to remove T-cell epitopes) antibodies.

The term "human antibody" includes antibodies obtained from human beings as well as antibodies obtained from transgenic mammals comprising human immunoglobulin genes such that, upon stimulation with an antigen the transgenic animal produces antibodies comprising amino acid sequences characteristic of antibodies produced by human beings. The term "antibody" should not be construed as limited to any particular means of synthesis and includes naturally occurring antibodies isolatable from natural sources as well as engineered antibodies molecules that are prepared by "recombinant" means including antibodies isolated from transgenic animals that are transgenic for human immunoglobulin genes or a hybridoma prepared therefrom, antibodies isolated from a host cell transformed with a nucleic acid construct that results in expression of an antibody, antibodies isolated from a combinatorial antibody library including phage display libraries.

Another type of tissue staining, similar to IHC, is imaging mass cytometry, which uses a panel of antibodies labeled with stable isotopes, typically metal isotopes. In a typical imaging mass cytometry workflow, tissue sections are prepared (e.g., formalin fixed, paraffin embedded tissue sections) and treated with a panel of metal-conjugated antibodies, each designed to target a distinct protein or marker of interest (e.g., cell surface proteins). A panel of antibodies or a panel of metal-conjugated antibodies includes a group of antibodies (two, three, four, five, six, seven, eight, nine, ten, or more), where the quantity, activity, or target of each antibody depends on the specimen obtained from a subject and the purpose of the staining. For example, a liver section from a patient suspected to be experiencing transplant rejection may require a panel of immune markers that recognize immune cells. As way of another example, a cancerous tissue section may require a different panel of immune markers from those used in the liver section. In another example, a tissue section from a healthy brain may be stained using a panel of metal-conjugated antibodies to detect general clusters of astrocytes, microglia, and neurons or more specific subclusters of cells such as excitatory neurons or inhibitory neurons. Further, a panel of antibodies may include any antibodies validated for imaging mass cytometry, any custom antibody conjugated with a heavy metal tag to be used for imaging mass cytometry, and the like.

The panel of antibodies may be labeled with heavy metal isotope tags such as rare-earth metals, nobel and post-transion metal isotopes, halogens and the like. Examples of metal tag labels include, without limitation, 113In, 115In (In=indium); 209Bi (Bi=bismuth); 89Y (Y=yttrium); 139La (La=lanthanum); 140Ce (Ce=cerium); 141Pr (Pr=praseodymium); 142Nd, 143Nd, 144Nd, 145Nd, 146Nd, 148Nd, 150Nd (Nd=neodymium); 147Sm, 149Sm, 152Sm, 154Sm (Sm=samarium); 151Eu, 153Eu (Eu=europium); 155Gd, 156Gd, 157Gd, 158Gd, 160Gd (Gd=gadolinium); 159Tb (Tb=terbium); 161Dy, 162Dy, 163Dy, 164Dy (Dy=dysproium); 165Ho (Ho=holmium); 166Er, 167Er, 168Er, 170Er (Er=erbium); 169Tm (Tm=thulium); 171Yb, 172Yb, 173Yb, 174Yb, 176Yb (Yb=ytterbium); 175Lu (Lu=lutetium); 103Rh (Rh=rhodium); 102Pd, 104Pd, 105Pd, 105Pd, 108Pd, 110Pd (Pd=palladium); 191Ir, 193Ir (Ir=iridium); 194Pt, 195Pt, 196Pt, 198Pt (Pt=platinum); and 127I (I=iodine). Additional metals and their corresponding isotopes that may also be used include Cadmium (Cd), tellurium (Te), silver (Ag), and osmium (Os).

The sections may then be individually mounted on corresponding slides, which an imaging system 125 can then scan or image to generate raw digital-pathology, or histopathology digital images 130a-n. In some instances, each section may be mounted on a slide, which is then scanned by imaging system 125 to create a digital image. In the specific instances of imaging mass cytometry, the stained images undergo laser ablation by imaging system 125 where each laser pulse removes a small portion of the sample. The ablated material is ionized, and the resulting ions are subjected to mass spectrometry analysis followed by multi-dimensional imaging where the output is a digital file (e.g., a .mcd file). The images 130a-n may be subsequently examined by digital pathology image analysis and/or interpreted by a human pathologist (e.g., using image viewer software). The pathologist may review and manually annotate the images of the slides (e.g., tissue degeneration, tissue damage, etc.) to enable the use of image analysis algorithms to extract meaningful quantitative measures (e.g., to detect and classify biological objects of interest). Conventionally, the pathologist may manually annotate each successive image of multiple tissue sections from a tissue sample to identify the same aspects on each successive tissue section.

The computing system 100 can further include a labeler 127 that labels the images 130 from the imaging system 125. Images that contain regions of interests (e.g., structural and/or functional biological entities associated with a disease/condition) may be given an "anomaly" label while those images that do not contain regions of interest may be give a label such as a "healthy" label.

Once generated, images 130a-n may be input into an analysis system 135 to train and execute a machine-learning model. Although not explicitly shown, prior to model training and execution, images 130a-n may be split into training and validation datasets so that the system can train and test prediction models 132a-n ('n' represents any natural number). The splitting of the images 130a-n may be performed randomly (e.g., a 90/10% or 70/30%) or the splitting may be performed in accordance with a more complex validation technique such as K-Fold Cross-Validation, Leave-one-out Cross-Validation, Leave-one-group-out Cross-Validation, Nested Cross-Validation, or the like to minimize sampling bias and overfitting. In addition to training and validation datasets, a portion of the images 130a-n may be saved and used in the inference subsystem 140 to test the trained model on images it has never seen before.

The model training subsystem 130 comprises two systems: a trainer 134 and a validator 136 for training and validating prediction models 132 to be used by the other subsystems, such as the model inference subsystem 140 for a given task. The prediction models 130 can be a convolutional neural network ("CNN"), e.g., an inception neural network, a U-Net, a V-Net, a residual neural network ("Resnet"), or a recurrent neural network, e.g., long short-term memory ("LSTM") models or gated recurrent units ("GRUs") models, other variants of Deep Neural Networks ("DNN") (e.g., a multi-label n-binary DNN classifier or multi-class DNN classifier). The prediction models 130 can also be any other suitable machine learning model that is unsupervised, semi-supervised, or supervised. Examples of machine learning algorithms include, without limitation, a random forest or random decision forest classifier, a Generative adversarial network (GAN), Naive Bayes Classifier, Linear Classifier, Support Vector Machine, Bagging Models such as random forest or random decision forest classifier, Boosting Models, Shallow Neural Networks, or combinations of one or more of such techniques—e.g., CNN-HMM or MCNN (Multi-Scale Convolutional Neural Network). In some instances, the prediction models 130 may be either a supervised algorithm or a completely automated and pre-trained deep learning algorithm to predict cell segmentation masks. In other instances, prediction models 130 may be supervised algorithm used to predict metaclusters of general cell phenotypes based on cell lineage markers. In a further example, prediction models 130 may be an unsupervised algorithm used to predict subclusters of cells based on the expression level of cell lineage markers. The system 100 may employ the same type of machine-learning model or different types of machine-learning models for making predictions. Still other types of machine-learning models may be implemented in other examples according to this disclosure.

Trainer 134 and validator 136 are part of a machine learning operationalization framework comprising hardware such as one or more processors (e.g., a CPU, GPU, TPU, FPGA, the like, or any combination thereof), memory, and storage that operates software or computer program instructions (e.g., TensorFlow, PyTorch, Keras, and the like) to execute arithmetic, logic, input and output commands for the random forest classifier model. Specifically, trainer 134 performs iterative operations of training that involve inputting portions of training data (e.g., images) into prediction models 130 to find a set of model parameters (e.g., weights and/or biases) that minimizes or maximizes an objective function (e.g., a loss function, a cost function, a contrastive loss function, etc.). Trainer 134 also performs the process of selecting hyperparameters, using an optimization algorithm, to find the model parameters that correspond to the best fit between prediction and actual outputs. Example optimization algorithms include a stochastic gradient descent algorithm or a variant thereof such as batch gradient descent or mini-batch gradient descent. The hyperparameters are settings that can be tuned or optimized to control the behavior of the prediction model 130. Most models explicitly define hyperparameters that control different aspects of the models such as memory or cost of execution. However, additional hyperparameters may be defined to adapt a model to a specific scenario. For example, the hyperparameters may include the number of hidden units of a model, the learning rate of a model, the convolution kernel width, the number of kernels for a model, the number of graph connections to make during a lookback period, the maximum depth of a tree in a random forest, a minimum sample split, a maximum number of leaf nodes, a minimum number of leaf nodes, and the like.

Once a set of model parameters are identified, the model has been trained and is then tested or validated using the validation datasets (e.g., images) by validator 136. The validation process includes iterative operations of inputting the validating datasets into the prediction models 130 using a validation technique such as K-Fold Cross-Validation, Leave-one-out Cross-Validation, Leave-one-group-out Cross-Validation, Nested Cross-Validation, or the like to fine tune the hyperparameters and ultimately find the optimal set of hyperparameters. Once the optimal set of hyperparameters are obtained, a reserved set of testing data, from the initial splitting of the preprocessed data, are input into trained model 145 to obtain output, and the output is evaluated versus ground truth values using correlation techniques such as Bland-Altman method and the Spearman's rank correlation coefficients and calculating performance metrics such as the error, accuracy, precision, recall, receiver operating characteristic curve (ROC), etc.

The model training subsystem 110 outputs trained models 145 with an optimized set of model parameters and hyperparameters for use in the model inference subsystem 140. The model inference subsystem 140 generates an inference phase prediction provided to users using a preprocessor and predictor 142 and the trained model 145. For example, the preprocessor and predictor 142 executes processes for inputting sample images into a trained model 145. Then the trained model 145 will output predictions. For example, if trained model 145 is a model that predicts cell segmentation masks, predictions may include applying boarders around individual cells in a tissue slice. In other instances, if trained model 145 is a supervised algorithm for generating meta-clusters of general cell phenotypes based on cell lineage markers, the prediction may include a list of general cell populations identified in a tissue section. In a further example, if the trained model 145 is an unsupervised algorithm for generating subclusters of cells based on the expression level of cell lineage markers, the predictions may include a list of subclusters identified in a tissue section.

Preprocessor and predictor 142 are part of the machine learning operationalization framework comprising hardware such as one or more processors (e.g., a CPU, GPU, TPU, FPGA, the like, or any combination thereof), memory, and storage that operates software or computer program instructions (e.g., Application Programming Interfaces (APIs), Cloud Infrastructure, Kubernetes, Docker, TensorFlow, Kubeflow, Torchserve, and the like) to execute arithmetic, logic, input and output commands for executing a machine learning model in a production environment. In some instances, the preprocessor and predictor 142 implement deployment of the model using a cloud platform such as Amazon Web Services (AWS), Google Cloud Platform (GCP), and Microsoft Azure. A cloud platform makes machine learning more accessible, flexible, and cost-effective while allowing developers to build and deploy the model faster.

Computing Environment

Figure 2:
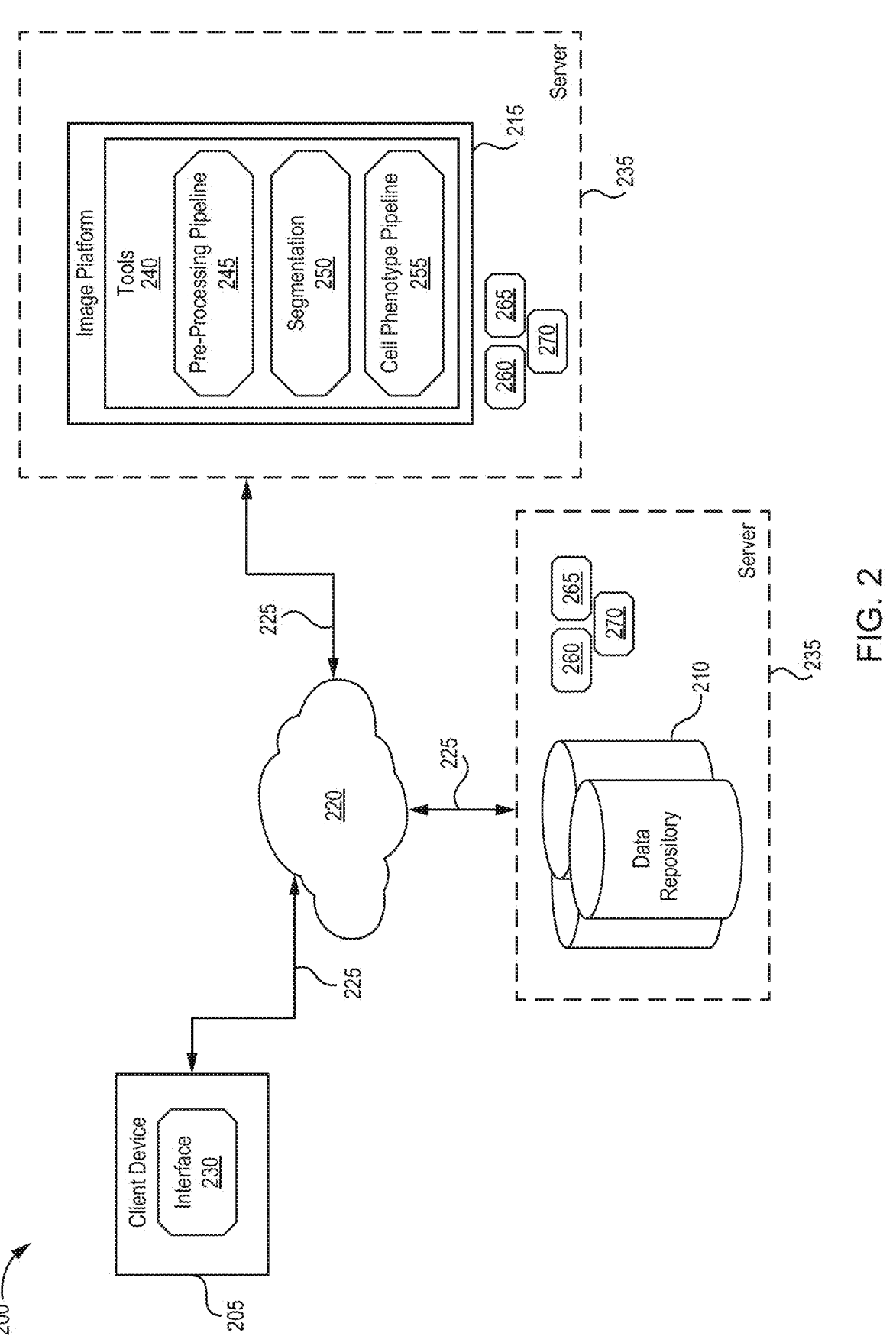
FIG. 2 shows a computing environment in accordance with various embodiments.

FIG. 2 shows a computing environment 200 in accordance with aspects of the present disclosure. Computing environment 200 includes a client device 205, a data repository 210, and image platform 215 connected to each other by a network 220. Although FIG. 2 illustrates a particular arrangement of a client device 205, a data repository 210, image platform 215, and a network 220, this disclosure contemplates any suitable arrangement of a client device 205, a data repository 210, an image platform 215, and a network 220. As an example, and not by way of limitation, two or more client devices 205, a data repository 210, and image platform 215 may be connected to each other directly, bypassing network 220. As another example, two or more client devices 205, a data repository 210, and an image platform 215 may be physically or logically co-located with each other in whole or in part. Moreover, although FIG. 2 illustrates a particular number of a client device 205, a data repository 210, an image platform 215, and network 220, this disclosure contemplates any suitable number of client devices 205, data repositories 210, discovery platforms 215, and networks 220. As an example, and not by way of limitation, computing environment 200 may include multiple client devices 205, data repositories 210, discovery platforms 215, and networks 215.

Network 220 may facilitate communication and exchange of data between client device 205, data repository 210, and image platform 215. Network 220 may include one or more networks that may be of the same or different types. Network 220 may support one or more communication protocols, including wired and/or wireless protocols, for facilitating the communications.

Links 225 may connect a client device 205, a data repository 210, and an image platform 215 to a network 220 or to each other. This disclosure contemplates any suitable links 225. In particular embodiments, one or more links 225 include one or more wireline (such as for example Digital Subscriber Line (DSL) or Data Over Cable Service Interface Specification (DOCSIS)), wireless (such as for example Wi-Fi or Worldwide Interoperability for Microwave Access (WiMAX)), or optical (such as for example Synchronous Optical Network (SONET) or Synchronous Digital Hierarchy (SDH)) links. In particular embodiments, one or more links 225 each include an ad hoc network, an intranet, an extranet, a VPN, a LAN, a WLAN, a WAN, a WWAN, a MAN, a portion of the Internet, a portion of the PSTN, a cellular technology-based network, a satellite communications technology-based network, another link 225, or a combination of two or more such links 225. Links 225 need not necessarily be the same throughout a computing environment 200. One or more first links 225 may differ in one or more respects from one or more second links 225.

Client device 205 may include various types of computing systems such as portable handheld devices, general purpose computers such as personal computers and laptops, workstation computers, wearable devices, various messaging devices, and the like. These computing devices may run various types and versions of software applications and operating systems (e.g., Microsoft Windows®, Apple Macintosh®, UNIX® or UNIX-like operating systems, Linux or Linux-like operating systems such as Google Chrome™ OS) including various mobile operating systems (e.g., Microsoft Windows Mobile®, iOS®, Windows Phone®, Android™, BlackBerry®, Palm OS®). Portable handheld devices may include cellular phones, smartphones, (e.g., an iPhone®), tablets (e.g., iPad®), personal digital assistants (PDAs), and the like. Further, client device 205 may be capable of operating one or more client applications. A user may use client device 205 to interact with network 220, such as to facilitate communication and exchange of data between the client device 205 and network 220. This disclosure contemplates any suitable client device 205 configured to generate and output product target discovery content to a user. For example, users may use client device 205 to execute one or more applications, which may generate one or more discovery or storage requests that may then be serviced in accordance with the teachings of this disclosure. A client device 205 may provide an interface 230 (e.g., a graphical user interface) that enables a user of the client device 205 to interact with the client device 205. The client device 205 may also output information to the user via this interface 230. Although FIG. 2 depicts only one client device 205, any number of client devices 205 may be supported.

A data repository 210 is a data storage entity (or sometimes entities) into which data has been specifically partitioned for an analytical or reporting purpose. The data repository 210 may be used to store data and other information for use by the image platform 215 and client device 205. For example, one or more of the data repositories 210(*a*) and 210(*b*) may be used to store data and information to be used as input into the image platform 215 for product target discovery. In some instances, the data and information relate to publicly or privately available images obtained by performing imaging mass cytometry and other information used by the image platform 215 when performing image cleaning functions (e.g., image artifact removal). The data repositories 210 may reside in a variety of locations including servers 235. For example, a data repository used by server 235 may be local to server 235 or may be remote from server 235 and in communication with server 235 via a network-based or dedicated connection of network 220. Data repositories 210(*a*) and 210(*b*) may be of different types or of the same type. In certain examples, a data repository may be a database. A database is an organized collection of data stored and accessed electronically from one or more storage devices such as one or more servers 235. The one or more servers 235 may be configured to execute a database application that provides database services to other computer programs or to computing devices (e.g., client device 205 and image platform 215) within the computing environment, as defined by a client-server model. One or more of these databases may be adapted to enable storage, update, and retrieval of data to and from the database in response to SQL-formatted commands or like programming language that is used to manage databases and perform various operations on the data within them.

Servers 235 may be composed of one or more general purpose computers, specialized server computers (including, by way of example, PC (personal computer) servers, UNIX® servers, mid-range servers, mainframe computers, rack-mounted servers, etc.), server farms, server clusters, or any other appropriate arrangement and/or combination. Servers 225 may include one or more virtual machines running virtual operating systems, or other computing architectures involving virtualization such as one or more flexible pools of logical storage devices that may be virtualized to maintain virtual storage devices for the server. In various examples, servers 225 may be adapted to run one or more services or software applications that provide the functionality described in the foregoing disclosure.

The computing systems in servers 225 may run one or more operating systems including any of those discussed above, as well as any commercially available server operating system. Servers 225 may also run any of a variety of additional server applications and/or mid-tier applications, including HTTP (hypertext transport protocol) servers, FTP (file transfer protocol) servers, CGI (common gateway interface) servers, JAVA® servers, database servers, and the like.

Exemplary database servers include without limitation those commercially available from Oracle®, Microsoft®, Sybase®, IBM® (International Business Machines), and the like.

In some implementations, servers 235 may include one or more applications to analyze and consolidate data feeds and/or data updates received from users of client computing devices 205. As an example, data feeds and/or data updates may include, but are not limited to, in vivo feeds, in silico feeds, or real-time updates received from public studies, user studies, one or more third party information sources, and data streams (continuous, batch, or periodic), which may include real-time events related to sensor data applications, biological system monitoring, and the like. Server 235 may also include one or more applications to display the data feeds, data updates, and/or real-time events via one or more display devices of client computing devices 205.

In various instances, servers 235 may be adapted to run one or more services or software applications that enable one or more embodiments described in this disclosure. In certain instances, servers 235 may also provide other services or software applications that may include non-virtual and virtual environments. In some examples, these services may be offered as web-based or cloud services, such as under a Software as a Service (SaaS) model to the users of client device 205. The term cloud service is generally used to refer to a service that is made available to users on demand and via a communication network such as the Internet by systems of a service provider. Typically, in a public cloud environment, servers and systems that make up the cloud service provider's system are different from the customer's own on-premise servers and systems. The cloud service provider's systems are managed by the cloud service provider. Customers may thus avail themselves of cloud services provided by a cloud service provider without having to purchase separate licenses, support, or hardware and software resources for the services. For example, a cloud service provider's system may host an application (e.g., the IMmuneCite pipeline described above), and a user may, via the Internet, on demand, order and use the application without the user having to buy infrastructure resources for executing the application. Cloud services are designed to provide easy, scalable access to applications, resources and services. Several providers offer cloud services. For example, several cloud services are offered by Google Cloud, Microsoft Azure, Amazon Web Services, and others.

Users operating client device 205 may in turn utilize one or more client applications to interact with server 235 to utilize the services provided by these components (e.g., database and discovery applications). In the configuration depicted in FIG. 2, servers 235 may include one or more components 260, 265 and 270 that implement the functions performed by servers 235. These components may include software components that may be executed by one or more processors, hardware components, or combinations thereof. It should be appreciated that various different device configurations are possible, which may be different from computing environment 200. The example shown in FIG. 2 is thus one example of a computing environment (e.g., a distributed system for implementing an example computing system) and is not intended to be limiting.

An image platform 215 (referred to as IMmuneCite in below descriptions) comprises a set of tools 240 for the purpose of processing, analyzing and visualizing data (i.e., data stored in data repository 210). The image platform 215 is an agnostic platform for processing image files to remove artifact signals and for identifying clusters of specific cell types. In the configuration depicted in FIG. 2, the set of tools 240 include a preprocessing pipeline 245 (referred to as IMClean in below descriptions), a segmentation tool 250, and a cell phenotyping pipeline 255 that implement the functions performed by the image platform 215. In some instances, the image platform 215 is used to: (i) preprocess raw images having artifact signals obtained from imaging experiments (e.g., image mass cytometry) to produce artifact free images, (ii) perform cell segmentation on the artifact free images using either a supervised classification method or a fully automated and pre-trained deep-learning enabled segmentation algorithm, and (iii) perform cell phenotype identification using a semi-supervised approach that includes identifying metaclusters of cells based on lineage markers and an unsupervised-based approach to identify specific cell subclusters, as described in detail below. The image platform 215 may reside in a variety of locations including servers 235. For example, an image platform 215 used by server 235 may be local to server 235 or may be remote from server 235 and in communication with server 235 via a network-based or dedicated connection of network 220. The image platform 215 may be of different configurations or of the same configuration. The one or more servers 235 may be configured to execute a discovery application that provides discovery services to other computer programs or to computing devices (e.g., client device 205) within the computing environment, as defined by a client-server model.

Denoising of Images

Artifact signals in images (e.g., the images acquired via systems and processes described with respect to FIGS. 1 and 2) may occur as a result of (i) channel spillover (or channel crosstalk) due to metal isotope impurity or oxide formation, (ii) background noise related to non-specific antibody binding, ion counting imaging-based technology, antibody concentration and tissue quality, (iii) aggregation signals presented as "hot pixels" caused by the aggregation of antibodies unrelated to a biological structure, and other technical issues associated with staining and fluorescence methods. The presence of artifact signals deteriorates the quality of the image and hinders downstream analysis. To overcome this, a method for processing imaging data to remove artifact signals is described.

Initially, a file image of a specimen, collected from a subject, stained with a panel of antibodies is accessed. The file image may be accessed from data repositories (e.g., data repositories 210 described with respect to FIG. 2). The image file is made up of region of interest files (subfiles) of the specimen, where the region of interest files represents regions indicated by a clinical pathologist showing signs of pathological concern. Depending on the health state of the subject (e.g., healthy, with a disease, transplant recipient, etc.) and the biological sample collected (e.g., cell-containing liquid or tissue), the regions of interest indicated by the clinical pathologist will differ. In the case of a liver transplant rejection, regions of interest may include lymphocytic infiltrate in bile duct, subendothelial lymphocytes infiltration (endotheliitis), bile duct loss (ductopenia), loss of hepatic arterioles, sinusoidal foam cell accumulation, and cholestasis. In other cases, such as cancer images, regions of interest may include abnormal appearance in size, number, shape, etc. of cells, areas of invasion, areas with high mitotic rate, and lymph node infiltration. Further, the region of interest files have individual signal files that correspond to each antibody (e.g., antibody channel) used in the panel of antibodies to stain the specimen. As way of example, and without limitation, an image file may have 10 regions of interest files, where each region of interest file has its own set of individual signal files that correspond the number of antibodies on the panel of antibodies. If 22 unique antibodies are used to stain the specimen, then each region of interest file has 22 individual signal files. In other words, a single specimen may have a total of 220 individual signal files with artifact signals that need removed.

In some instances, the file image of the specimen stained with a panel of antibodies is generated using any of the staining techniques (e.g., H&E, IHC, imaging mass cytometry, etc.) discussed with respect to the image generation system 105 described in FIG. 1. In some instances, the file image of the specimen stained with a panel of antibodies is obtained from imaging mass cytometry. The specimen can be a tissue sample obtained by tissue biopsy from a health patient, a patient with a disease, or a patient who received an organ transplant. In some instances, the specimen is a tissue sample obtained from a patient with a disease (e.g., cancer). In other instances, the specimen is a tissue sample obtained from a patient who is an organ transplant recipient. In a further example, the specimen is from a patient with organ transplant rejection. In some cases, the specimen is a liver tissue sample obtained from a patient with liver transplant rejection.

As described with respect to FIG. 1, the panel of antibodies may include any antibodies validated for imaging mass cytometry, any custom antibody conjugated with a heavy metal tag to be used for imaging mass cytometry, and the like. Further, the panel of antibodies is designed to target a distinct protein or marker of interest (e.g., cell surface proteins) based on the cells expected to be present in the biological sample and the purpose of the staining. By way of example, without limitation, the file image may be of a specimen (e.g., a human patient with a liver transplant rejection) stained with a panel of antibodies that target CD4+ T-cells, CD8+ T-cells, B cells, macrophages, monocytes, plasma cells, neutrophils, endothelial cells, cholangiocytes, hepatocytes, or any combination thereof based on the expression profile given off by the panel of antibodies. Further, the panel of antibodies can distinguish more specific types of cells such as cholangiocytes, endothelial cells, hepatocytes, B cells, proliferating B cells, PD1+ B cells, CD3+ CD4+ T cells, resident memory CD4+ T cells, naïve CD4+ T cells, HLADR+ CD4+ T regulatory cells, HLADR− CD4+ T regulatory cells, PD1+ CD4+ T cells, proliferating CD4+ T cells, activated CD4+ T cells, CD16+ CD4+ T cells, CD3+ CD8+ T cells, cytotoxic T cells, proliferating CD8+ T cells, PD1+ CD8+ T cells, PD1+ CD28+ CD8+ T cells, M1 macrophages, proliferating M1 macrophages, CD11b+ M1 macrophages, CD16+ M1 macrophages, M2 macrophages, CD11b+ M2 macrophages, CD16+ M2 macrophages, HLADR+ M2 macrophages, classical monocytes, non-classical monocytes, intermediate monocytes, activated monocytes, neutrophils, plasma cells, or any combination thereof. To detect the above mentioned cell types in a specimen (e.g., a human patient with a liver transplant rejection) the panel of antibodies may include two, three, four, five, six, seven, eight, nine, ten, or more antibodies that recognize cell surface proteins such as CD66b (neutrophils), CD20 (B-cells), CD28, CD16, CD163, CD11b, CD45 (pan-leukocyte marker), CD4, CD31, CD279, CD68 (macrophages), Foxp3, CK7, Ki-67, CD8a (cytotoxic T-cells), Collagen Type I (non-immune marker for tissue architecture), CD3e (T-cell receptor), CD138, HLA-DR, Granzyme B, DNA1, and DNA2 targets (also see Table 1 and FIG. 4A-4D).

Figure 14A:
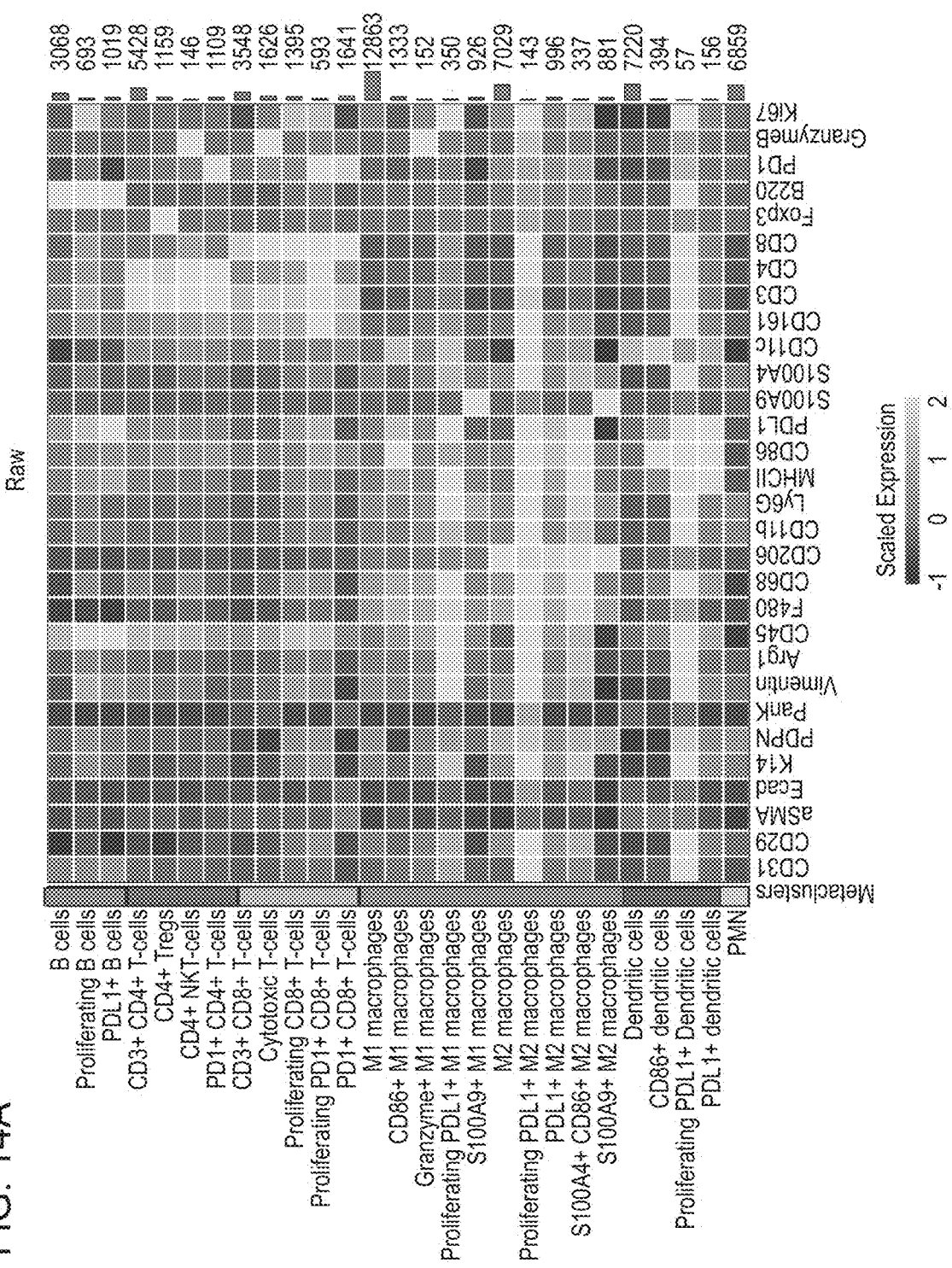
FIGS. 14A and 14B show the validation of the IMmuneCite workflow in HCC mouse models.
Figure 14B:
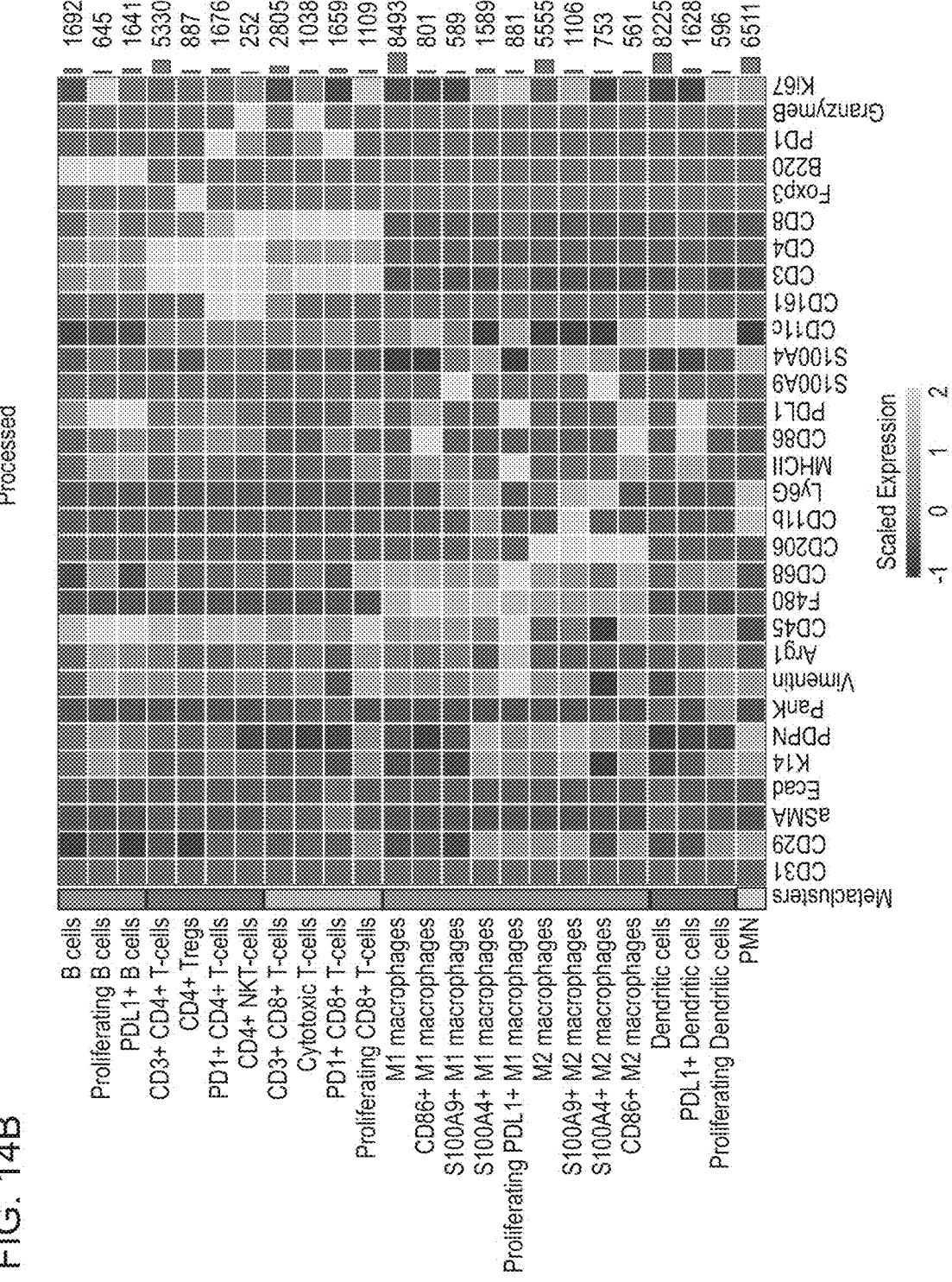

In some instances, the panel of antibodies may include more than 22 unique antibodies, for example 25, 30, 35, 40, 45, 50 or more unique antibodies that recognize cell surface proteins. As an additional example, the file image may be of a specimen (e.g., a mouse hepatocellular carcinoma model) stained with a panel of antibodies that may include two, three, four, five, six, seven, eight, nine, ten, or more antibodies that recognize cell surface proteins such as aSMA, CD29, Ecad, CD31, CD3, CD4, CD8, B220, CD11b, CD161, Ly6G, F480, CD68, CD206, CD11c, MHCII, S100A9, S100A4, PDPN, K14, PanK, Vimentin, Arg1, Foxp3, CD86, GranzymeB, CD45, PDL1, PD1, and Ki67 (see FIGS. 14A and 14B). The provided panel of antibodies in this particular example may be used to detect B cells, T-cells, macrophages, dendritic cells, and polymorphonuclear cells. The provided panel of antibodies may be used to distinguish between general cell types and identify more specific cell types such as B cells, proliferating B cells, PDL1+ B cells, CD3+ CD4+ T cells, CD4+ T regulatory cells, CD4+ NKT cells, PD1+ CD4+ T cells, CD3+ CD8+ T cells, cytotoxic T cells, proliferating CD8+ T cells, proliferating PD1+ CD8+ T cells, PD1+ CD8+ T cells, M1 macrophages, CD86+M1 macrophages, Granzyme+ M1 macrophages, proliferating PDL1+ M1 macrophages, S100A9+ M1 macrophages, M2 macrophages, PDL1+ M2 macrophages, S100A4+ CD86+ M2 macrophages, S100Ad+ M2 macrophages, dendritic cells, CD86+ dendritic cells, PDL1+ dendritic cells, and polymorphonuclear cells. One skilled in the art should appreciate from the examples provided, that the image processing techniques described herein can be applied to both human and animal samples, to a vast array of clinical images (liver rejection images, cancer images, etc.), and that different panels of antibodies are used depending on the subject, tissue, disease/condition, staining purposes, and the like.

The panel of antibodies may include a user defined panel of antibodies that depend on the specimen type and cells present in the specimen. For example, a specimen may be from heart tissue and comprise adipocytes, lymphoids, mesothelial cells, myeloid cells, neuronal cells, pericytes, smooth muscle cells, fibroblasts, atrial cardiomyocytes, ventricular cardiomyocytes, and the like. Thus, a user will design an antibody panel comprising antibodies that recognize cell surface proteins (e.g., cell lineage markers) on adipocytes, lymphoids, mesothelial cells, myeloid cells, neuronal cells, pericytes, smooth muscle cells, fibroblasts, atrial cardiomyocytes, ventricular cardiomyocytes, and the like. Accordingly, the panel of antibodies allow for distinction of general cell type (e.g., a metacluster) and more specific cell types within a metacluster (e.g., a subcluster). For example, to distinguish neuronal cells from endothelial cells, an antibody panel may include antibodies that target PLP1, NRXN1, NRXN3, and other neural cell specific markers and antibodies that target VWF, PECAM1, CDH5, and other endothelial cell specific markers.

Further, the panel of antibodies may be labeled with heavy metal isotope tags such as rare-earth metals, noble and post-transition metal isotopes, halogens and the like when the image file is generated by image mass cytometry. Examples of metal tag labels include, without limitation, 113In, 115In (In=indium); 209Bi (Bi=bismuth); 89Y (Y=yttrium); 139La (La=lanthanum); 140Ce (Ce=cerium); 141Pr (Pr=praseodymium); 142Nd, 143Nd, 144Nd, 145Nd, 146Nd, 148Nd, 150Nd (Nd=neodymium); 147Sm, 149Sm, 152Sm, 154Sm (Sm=samarium); 151Eu, 153Eu (Eu=europium); 155Gd, 156Gd, 157Gd, 158Gd, 160Gd (Gd=gadolinium); 159Tb (Tb=terbium); 161Dy, 162Dy, 163Dy, 164Dy (Dy=dysproium); 165Ho (Ho=holmium); 166Er, 167Er, 168Er, 170Er (Er=erbium); 169Tm (Tm=thulium); 171Yb, 172Yb, 173Yb, 174Yb, 176Yb (Yb=ytterbium); 175Lu (Lu=lutetium); 103Rh (Rh=rhodium); 102Pd, 104Pd, 105Pd, 105Pd, 108Pd, 110Pd (Pd=palladium); 191Ir, 193Ir (Ir=iridium); 194Pt, 195Pt, 196Pt, 198Pt (Pt=platinum); and 127I (I=iodine). Additional metals and their corresponding isotopes that may also be used include Cadmium (Cd), tellurium (Te), silver (Ag), and osmium (Os). In some instances, the heavy metal tags may comprise 139La, 142Nd, 144Nd, 146Nd, 147Sm, 149Sm, 152Sm, 153Eu, 154Sm, 156Gd, 159Tb, 160Gd, 164Dy, 167Er, 168Er, 169Tm, 170Er, 172Yb, 174Yb, 175Lu, 191Ir, or 193Ir.

In some cases, the artifact signals are due to background noise. To remove the artifact signals, an image pre-processing method (see pre-processing pipeline 245 described with respect to FIG. 2) using a denoising filter is performed on the individual signal files. In an iterative process starting with a first individual signal file of the individual signal files from a first region on interest file of the regions of interest files, a first denoising threshold value is applied to generate a first noise signal, and a second denoising threshold value is applied to generate a second noise signal. In various instances, the first denoising threshold value is a minimum filter value dependent upon the antibody panel and corresponding to a signal level below a designated minimum threshold, and the second denoising threshold value is a uniform filter value used to average pixel intensities. A user may enter values for the minimum threshold parameter and the uniform threshold parameter. The minimum threshold value may be dependent on the antibodies used. Typically, noise signals have a lower expression (e.g., signal level) compared to true signals. With the minimum filter, any signal with an expression/signal level below the designated minimum threshold is considered noise and is set to a null value (e.g., a first noise signal). In some instances, signal from noise is from a different origin and has different characteristics compared to a true signal. For example, true signals correlate with patterns of cellular structures (e.g., cell nuclei, membranes, vessels, or the like). On the other hand, false signals do not correlate with a pattern. By smoothing the signal with a uniform filter, based on the uniform threshold value input by the user, individual expression/signal are replaced with an average signal value of its neighboring pixels' expression/signals. Any signal from pixels that are not part of a larger pattern (e.g., cellular structure) represent noise and are set to a null value (e.g., a second noise signal).

In some instances, the minimum filter value may be set to a desired integer, and the uniform threshold value may be set to a null value, indicating the uniform filter is not applied. In other instances, the minimum filter value may be set to a null value (and thus not applied) while the uniform threshold value may be set to a desired integer value. In a further example, the minimum filter value may be set to a desired integer value, and the uniform threshold value may be set to a desired integer value indicating both filters are applied to the region. Once the value for both the minimum filter and the uniform filter are selected, the filters are applied to the image (e.g., the first noise signal and the second noise signal) to remove the noise from the image and generate a denoised image.

The denoised image may then be compared to the first individual signal file (i.e., the original file) to determine the performance quality of the denoising filter. In some cases, a user may decide to reapply the denoising filter and repeat the above-described process on the first individual signal file from the first region of interest file but select a different minimum threshold value and uniform threshold value. In other cases, the user may repeat the above-described process on the first individual file from a second or subsequent region of interest files. In this instance, the user has the option to either (i) apply the same minimum threshold value and uniform threshold value to all the first individual files in the second or subsequent regions of interest files, (ii) apply different minimum threshold value and uniform threshold value to each of the first individual files in the second or subsequent regions of interest files, or (iii) a combination of (i) and (ii). The final option is for the user to finalize the iterative process. If the user finalizes the iteration, the iterative process will continue to a second or subsequent individual signal file from the first region of interest file to generate a set of denoised images for the specimen. The set of denoised images may then be output and stored in a data repository (as described with respect to FIG. 2) for downstream analysis (e.g., cell segmentation, cell phenotype identification) or they may undergo additional image cleaning/image pre-processing filter(s) to remove other artifact signals, such as antibody aggregates or channel spillover.

The image pre-processing method described herein may include one or more additional artifact removal filters. By way of example, the image pre-processing method can further comprise performing another iterative process to remove artifacts from the set of denoised images. Initially, a first denoised image from the set of denoised images is processed using a spillover correction filter to generate a spillover correction image. Then, the spillover correction image is processed using an aggregate removal filter to generate an aggregate removal image. These steps may be repeated for a second or subsequent denoised image from the set of denoised images to generate a set of stacked images comprising the aggregate removal images.

Overview of IMmuneCite Pipeline

In some aspects, a method for processing imaging data, specifically a method for removing artifact signals from imaging data to generate clean, high-quality images for cell identification is described herein. In the description below, this method is referred to as the IMmuneCite pipeline.

Figure 3:
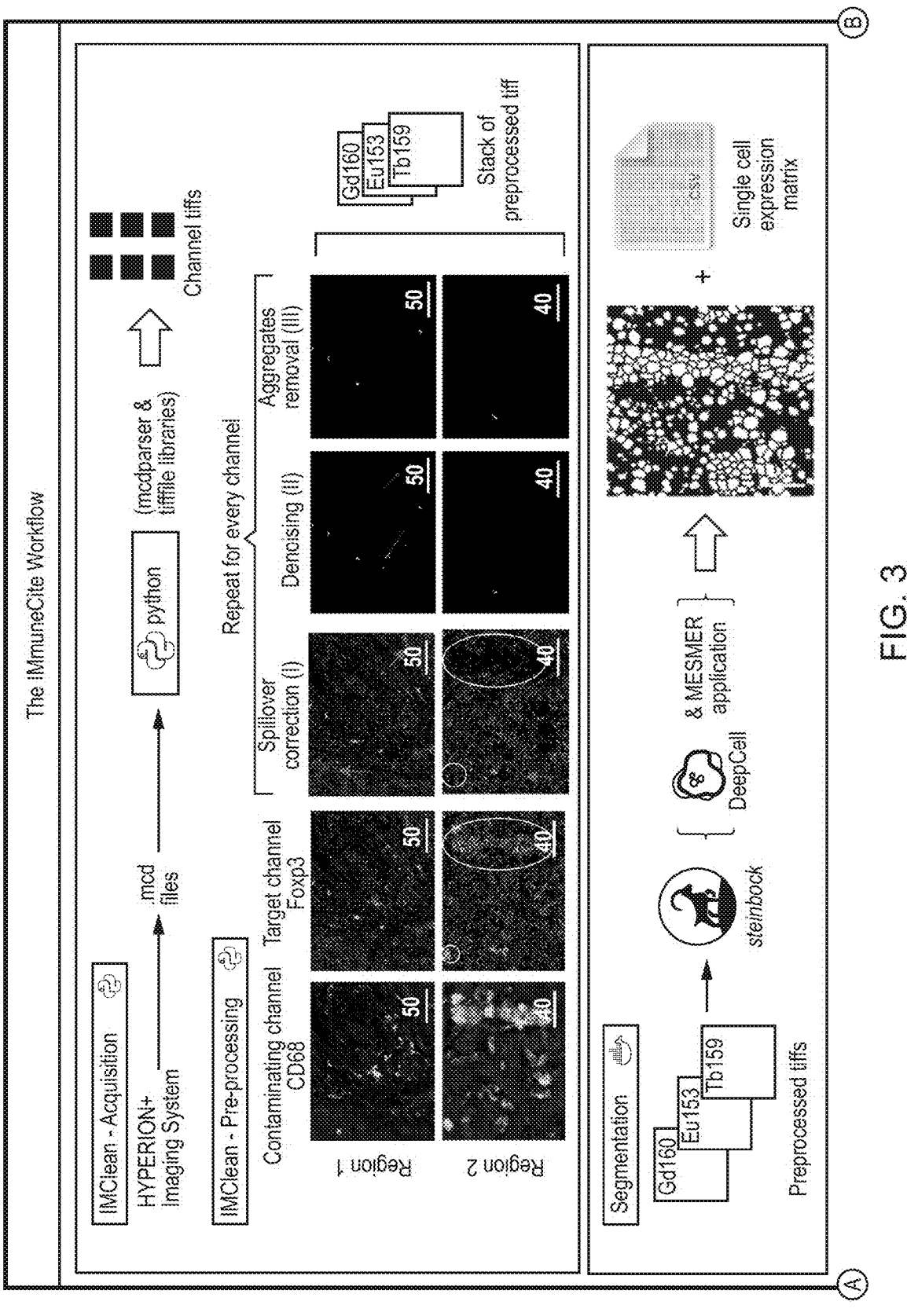
FIG. 3 shows an overview of the IMmuneCite workflow for spatial proteomic data comprising pre-processing (IMClean, blue), segmentation (orange), and cell phenotyping (green). The IMClean Acquisition section shows med files obtained after tissue ablation by the Hyperion system are imported into the IMClean pipeline and converted into tiff. files (a single tiff file corresponds to a single channel). The IMClean Preprocessing section illustrates that each single channel image is processed in a three-step approach: channel spillover correction (or channel crosstalk removal), denoising and aggregate removal. For example: in region 2, the raw image shows two areas of channel spillover (white ovals), which are corrected for in the first processing step (background removal). Green arrows point to areas of unspecific signal (noise) corrected for in the second imaging processing step (denoising). Red arrows (region 1) highlight antibody aggregates that are removed during the final step (aggregates removal). Afterwards, a stack of tiffs is created for each tissue section (also known as ROI) to include each channel to be used for analysis and is ready for image segmentation. The segmentation section shows segmentation of the IMClean-processed images using Mesmer to obtain single-cell masks and expression matrix to use for downstream analysis. The Cell Phenotype section illustrates how marker expression measurements are read into R and used for cell phenotype assignment using the IMmuneCite clustering algorithm for human samples. Information on the top three highest expressed markers is extracted and used for cell categorization and metaclusters phenotype assignment based on the algorithmic tree schematized in Cell Phenotyping section. (Needs to have a positive value; To account for imperfect CD4 staining (cells co-expressing CD4 and CD8) and spillover of signal from macrophages (due to their shape) into adjacent cell masks (cells co-expressing CD68/CD163 and CD4/CD8). The Single-cell Data Visualization and Analysis section shows that single-cell data can be statistically compared, and cell phenotype can be visualized onto the mask of the corresponding tissue section. (Scale bar unit=μm).
Figure 3:
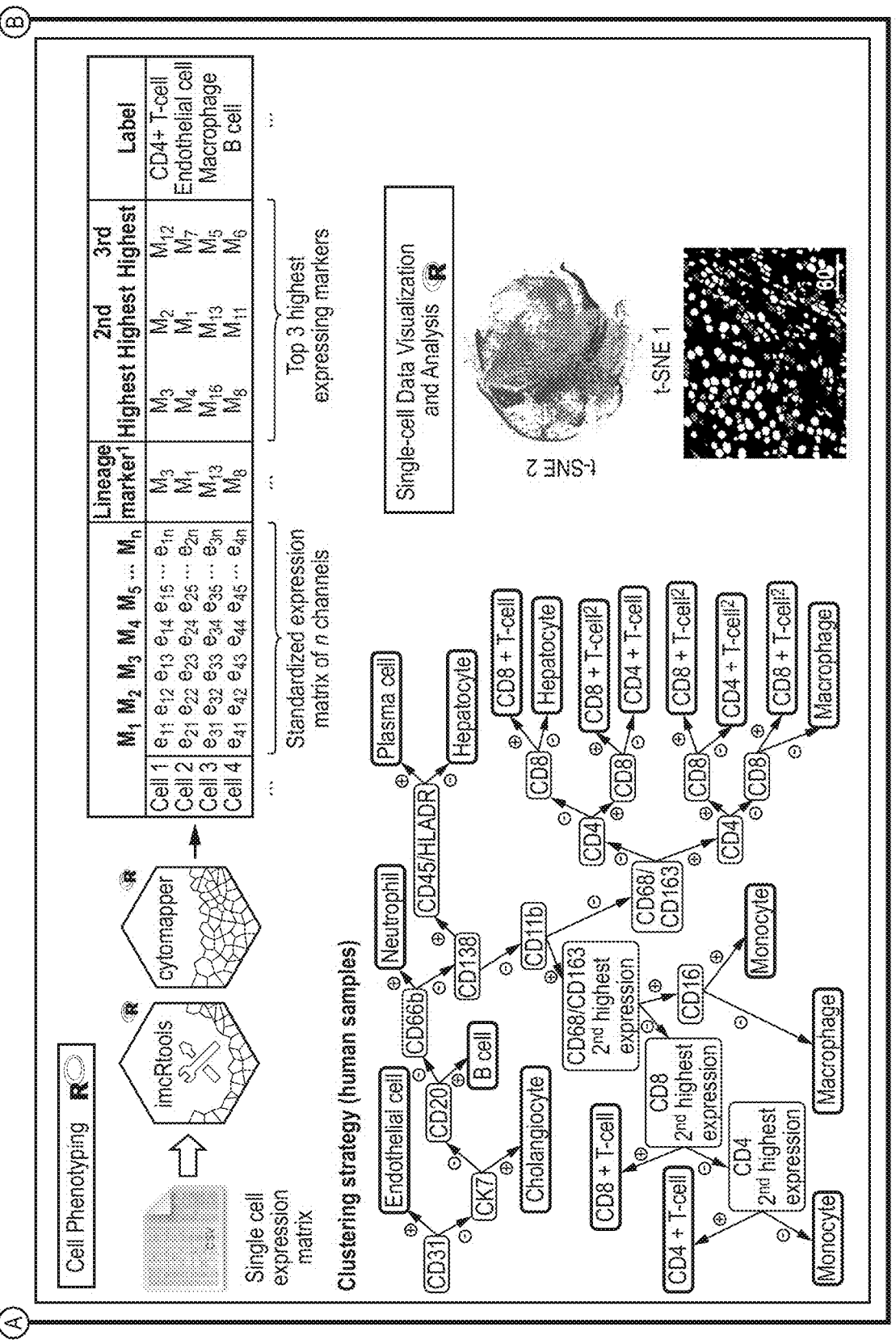

The IMmuneCite pipeline (i.e., the image platform 215 described with respect to FIG. 2) executes a three-step framework that allows pre-processing of raw images and cell identification through integration of newly developed tools to create an accurate single-cell proteomic dataset to feed into downstream statistical and spatial analyses (FIG. 3). Each step—pre-processing (preprocessing pipeline 245 described with respect to FIG. 2), segmentation (segmentation tool 250 described with respect to FIG. 2), and cell phenotyping (cell phenotype pipeline 255 described with respect to FIG. 2)—may be executed individually through their respective files or all together. Further, these tools run on freely available platforms such as python, docker, R, and the like, whereas other similar workflows in the art require specialized and costly platforms to run on.

The first step of the IMmuneCite pipeline, IMClean (FIG. 3), includes image pre-processing. Image pre-processing starts with data acquisition by transforming MCD files generated by a multi-channel imaging system (e.g., the Hyperion imaging system), into single channel tiff file images. This transformation may be done using a set of computational tools (e.g., imctools, tifffile, and shutil packages). The transformation of MCD files into tiff files serves several purposes. The first being that MCD files have vendor specific formatting. By converting to tiff files, all downstream analysis and visualization of generated images is done so in a vendor independent fashion, increasing the accessibility of the disclosed imaging processing technology. The second main reason for file transformation is that a single MCD file stores all the information regarding the regions of interest and all the antibodies used in the antibody panel, making image processing impractical. In order to improve the imaging processing, individual tiff files are extracted from the MCD files. Each individual tiff file comprises the information for a single antibody channel for a single region of interest. Accordingly, a more customized and thorough "cleaning" of the images is achieved.

After file transformation, the individual tiff files are stored as a single image file. Accordingly, the image file is made up of region of interest files of the specimen, where the region of interest files have individual signal files that correspond to each antibody (e.g., antibody channel) used in the panel of antibodies to stain the specimen. The individual files have artifact signals (e.g., channel spillover contamination, noise, signal aggregates, and the like) diminishing the quality of the images and their use for downstream analysis. Thus, an image pre-processing method (e.g., IMClean Pre-processing shown in FIG. 3) is performed on the region of interest files to remove the artifact signals from each of the individual signal files comprising each of the regions of interest. In one exemplary embodiment, the image pre-processing (e.g., IMClean Pre-processing shown in FIG. 3) pipeline occurs in an iterative process starting with a first individual signal file from a first region of interest. The first individual signal file has artifact signals, such as channel spillover contamination, noise, signal aggregates, and the like, diminishing its overall quality. The first individual signal file is processed by (1) a first artifact filter, (2) a second artifact filter, and (3) a third artifact filter to generate an artifact free or "clean" image that is of much higher quality for downstream analysis. Pre-processing is done on one individual signal image at a time for each region of interest. For example, the first individual signal file from region of interest 1 is Foxp3. The Foxp3 signal file from region of interest 1 is processed by the first artifact filter, the second artifact filter, and then the third artifact filter. After artifact filtering, one option is to apply the exact Foxp3 cleaning parameters/thresholds used in region of interest 1 to the Foxp3 signal file in the remaining region of interest files or the cleaning parameters/thresholds may be individually selected. After Foxp3 is processed for all region of interest files, the IMClean pipeline moves on to the next antibody and repeats the pre-processing steps. In so doing, each antibody is given a different set of thresholds/parameters specific for that antibody.

(1) Processing of the first individual signal file involves the use of the first artifact filter. The output of the first artifact filter corresponds to a spillover corrected image. Channel spillover occurs when one channel ("source") contaminates another channel ("target"). This is caused by either ionic contamination or by isotopic impurities in the metal stocks (e.g., metal tag labels on the antibodies in the panel of antibodies) that are used for antibody conjugation. In one exemplary embodiment, the first artifact filter is a spillover correction filter that performs a series of steps, (a)-(h), to remove artifacts attributed to channel spillover as described below.

a) Extracting, from the first region of interest file, a source channel and a target channel, wherein the target channel is the first individual signal file from the first region of interest file.

b) Into the spillover correction filter, the source channel, the target channel, a cap threshold value, a Gaussian radius value, a binarizing threshold value, and a removal value are input. The target channel is the first individual signal file from the first region of interest file. The source channel is processed first by capping, smoothing, and binarizing the signal to generate a mask.

c) Capping involves applying, to the source channel, the cap threshold value specified by the user, which is proportional to the expected intensity of the contaminating channel. The cap threshold value is the maximum signal value for the source channel.

d) To smooth the signal values, a Gaussian radius filter (based on the user input the Gaussian radius value) is applied to the source channel. The Gaussian radius filter blurs and smooth the signal, where the higher the Gaussian radius value, the higher the blurring.

e) Binarizing involves applying, to the source channel, the binarizing threshold value specified by the user. This value sets any signal value above the binarizing threshold value to a first predetermined value (e.g., an integer such as "1") and any signal value below the binarizing threshold value to a second predetermined value (e.g., a null value such as "0") to generate a binarized mask corresponding to the areas in the source channel that are either positive for signal spillover or negative for signal spillover.

f) A spillover corrected image is generated by applying, to the target channel, the removal value selected by the user. The removal value is subtracted from all the pixels in the target channel that correspond to the pixels in the binarized mask image with the predetermined value (e.g., "1").

g) To determine the performance quality of the spillover correction filter, the raw signal from the target channel is compared to the signal in the spillover corrected image.

h) At the end of the spillover correction process, the user selects an option: (i) repeat, for the first individual signal file, steps (a)-(g) with updated values input for the cap threshold, the Gaussian radius, the binarizing threshold, the removal, or any combination thereof, (ii) perform a second spillover correction by repeating steps (a)-(g) with a new source channel selected from the individual signal files from the first region of interest file, or (iii) finalize the spillover correction step and output a spillover corrected image.

The spillover corrected image may then be stored in a data repository (as described with respect to FIG. 2) for downstream analysis (e.g., cell phenotype identification) or the spillover corrected image may be input into another image cleaning step to remove additional artifact signals, such as background noise or antibody aggregates. For example, the spillover corrected image may be input into a process that uses a second artifact filter to remove background noise. The spillover correction step is based on the MAUI software package as described in Baranski A, Milo I, Greenbaum S, et al. MAUI (MBI Analysis User Interface)—An image processing pipeline for Multiplexed Mass Based Imaging. PLOS Comput Biol. 2021; 17(4):e1008887. doi:10.1371/JOURNAL.PCBI.1008887.

(2) Processing of the spillover corrected image involves the use of the second artifact filter. The output of the second artifact filter corresponds to a denoised image. Image noise can occur due to a variety of reasons such as instrumentation used during imaging mass cytometry staining, tissue quality, and nonspecific antibody binding, all of which can result in the generation of weak, non-biological signal. In an exemplary embodiment, the second artifact filter is a noise removal filter and performs a series of steps, (a)-(f), to remove artifacts attributed to background noise as described below.

a) Into the noise removal filter, the spillover corrected image, a minimum threshold value, and a uniform threshold value are input.

b) The minimum threshold value, which is dependent on the antibody panel used, is applied to the spillover corrected image. Typically, noise signals have a lower expression (e.g., signal level) compared to true signals. With the minimum filter, any signal with an expression/signal level below the designated minimum threshold is considered noise and set to a null value to generate a first noise signal.

c) The uniform filter value is used to set a uniform filter that is then applied to the spillover corrected image. In some instances, signal from noise is from a different origin and has different characteristics compared to a true signal. For example, true signals correlate with pattern of cellular structures (e.g., cell nuclei, membranes, vessels, or the like). On the other hand, false signals do not correlate with a pattern. By smoothing the signal with a uniform filter, based on the uniform threshold value input by the user, individual expressions/signals are replaced with an average of its neighboring pixels' expression/signals. Any signal from pixels that are not part of a larger pattern, and thus represent noise, are set to a null value to generate a second noise signal.

In some instances, the minimum filter value may be set to a desired integer and the uniform threshold value may be set to a null value (e.g., "0"), indicating the uniform filter is not applied. In other instances, the minimum filter value may be set to a null value (and thus not applied) while the uniform threshold value may be set to a desired integer value. In a further example, the minimum filter value may be set to a desired integer value, and the uniform threshold value may be set to a desired integer value indicating both filters are applied to the region. As a final example, the minimum filter value may be set a null value, and the uniform threshold value may also be set to a null value indicating that neither filter is applied to the region of interest.

d) Once the value for both the minimum filter and the uniform filter are selected, the filters are applied to the image (e.g., the first noise signal and the second noise signal) to remove the noise associated with background artifact signals. This generates a first denoised image.

e) To determine the performance quality of the noise removal filter, the spillover corrected image is compared to the denoised image. At the end of the noise removal process, the user selects an option: (i) repeat, steps (a)-(e) with different values selected for the minimum threshold value and the uniform threshold value, or (ii) finalize the denoising step to generate a denoised images.

If the user finalizes the denoising step, the output denoised image may then be stored in a data repository (as described with respect to FIG. 2) for downstream analysis (e.g., cell phenotype identification) or the denoised image may be input into another image cleaning step to remove additional artifact signals, such as channel spillover or antibody aggregates. For example, the denoised image may be input into a process that uses a third artifact filter to remove antibody aggregates.

(3) Processing of the denoised image involves the use of the third artifact filter. The output of the third artifact filter corresponds to an aggregate removal image. Aggregates can occur due to conglomerations of antibodies that result in high counts in concentrated areas. This impacts downstream analysis as the aggregates lead to false positive artifact signals in antibody staining. Detection and removal of antibodies requires caution as it can result in removal of true signal, thus expert knowledge of the tissue, cellular shapes, and how antibodies are supposed to stain is necessary. In an exemplary embodiment, the third artifact filter is an aggregate removal filter and performs a series of steps, (a)-(f), to remove artifacts attributed to conglomerations of antibodies as described below.

a) Into the aggregate removal filter, the denoised image, a Gaussian radius value, and a size threshold value, are input.

b) The Gaussian radius value is applied to the denoised image to blur and smooth the denoised image, generating a blurred image. Blurring aids in the distinction of true signal from false positive signals. For example, nearby patches of true signal merge together to become a larger structure, such as a cell or vessel, while antibody aggregates tend to remain on their own and therefore have a smaller size/radius.

c) Binarizing involves applying, to the blurred image, the size threshold value specified by the user. This value sets any structure with size/radius value above the size threshold value to a predetermined value (e.g., "1") and any structure with size/radius value below the size threshold value to a null value (e.g., "0") to generate a binarized mask corresponding to the areas in the blurred image that are either true positive signal or aggregate signal.

d) An aggregate removal image is generated by removing, from the blurred image, the structures whose size/radius value correspond to the structures in the binarized mask given a null value.

e) To determine the performance quality of the aggregate removal filter, the denoised image is compared to the aggregate removal image.

f) At the end of the aggregate removal process, the user selects an option: (i) repeat, for the denoised image, steps (a)-(e) with different values selected for the Gaussian radius value and the binarizing threshold value, or (ii) finalize the aggregate removal step and output an aggregate removal image.

If the user finalizes the aggregate removal step, the aggregate removal image may be stored in a data repository (as described with respect to FIG. 2) for downstream analysis (e.g., cell phenotype identification) or the aggregate removal image may be input into another image cleaning step to remove additional artifact signals, such as channel spillover or noise removal. For example, the aggregate removal image may be input into a pipeline for downstream analysis, such as the cell segmentation step and IMmuneCite Clustering pipeline described in detail below. The aggregate removal filter is based on the MAUI software package as described in Baranski A, Milo I, Greenbaum S, et al. MAUI (MBI Analysis User Interface)—An image processing pipeline for Multiplexed Mass Based Imaging. PLOS Comput Biol. 2021; 17(4):e1008887. doi:10.1371/JOURNAL.PCBI.1008887.

Once the first individual signal file from the first region of interest is processed by the first artifact filter, the second artifact filter, and the third artifact filter, the processing is repeated for the first individual signals from a second or subsequent regions of interest file. Prior, the user may select one of three options: (i) apply the same values selected for the first artifact filter, the second artifact filter, and the third artifact filter used for the first individual signal file from the first region of interest file to each of the other first individual signal files in the other regions of interest files, (ii) select new values for the first artifact filter, the second artifact filter, and the third artifact filter to be applied to each of the other first individual signal files in the other regions of interest files, or (iii) a combination of (i) and (ii).

After all the first individual signal files are processed, the iterative process proceeds onto a second or subsequent individual signal file for the first region of interest. The processed files may be exported and saved in a data repository. In addition, processed files are combined to create a stack of .tiff files per region of interest, as required for cell segmentation. The stack of .tiff files comprise the aggregate removal images generated for each region of interest of the specimen. This is again done by using the tifffile package.

In the second step of the IMmuneCite workflow (FIG. 3), cell segmentation is performed on the single image stacks. The user can alternatively select between two cell segmentation approaches: Ilastik/Cellprofiler, a supervised pixel classification method, or Mesmer, a completely automated and pre-trained deep-learning-enabled segmentation algorithm. In the current study, cell segmentation was performed using Mesmer. Segmentation outputs include single-cell data (including expression matrix as well as morphological and spatial features), segmentation masks, and antibody signal images ready to be used for cell phenotyping (FIG. 3) and downstream visualization and analysis (FIG. 3).

IMmuneCite Clustering Description and Implementation

The final step of the IMmuneCite pipeline enables cell phenotype identification (FIG. 3). This step is comprised of a semi-supervised approach with a two-step process-identification of metaclusters and identification of subclusters. Data is first arcsine transformed and then standardized by channel to account for differences in signal intensities.

Metaclusters represent general cell phenotypes and are recognized using lineage markers (e.g., CD4, CD8, CD68, CD163, CD20). Identification of metaclusters is based on rules and thresholds of the scaled marker expression. The user will specify a set of rules for how the metaclusters are identified. Each rule needs to state the lineage marker used to identify a particular metacluster, whether certain markers need to be expressed above a certain threshold, and whether the highest expressing markers (e.g., top 2, 3, 4, or 5 markers) should include or exclude a set of markers. Further, for each cell, information on lineage marker and the top highest expressed markers (e.g., the top three highest) are then extracted and used to assign cell phenotypes using a combination of these user-defined thresholds for the lineage markers of interest and logical operators (FIG. 3). For example, a user may wish to identify the B cell metacluster in human samples as follows: CD20 as the lineage marker, a positive expression of CD20 (that is, the scaled expression of CD20 is above 0), and the 3 highest expressing markers exclude markers such as CD4, CD8, CD68, CD163, CD66b, CD31, CK7, and Granzyme B. The latter is to ensure that cells with a non-biological phenotype (for example, cells that express both B cell and macrophage markers) were excluded. The user may also use multiple set of rules to identify a particular metacluster. For example, to identify macrophages in human samples, a user may define a set of rules using CD68 as the lineage marker and another set of rules using CD163 as the lineage marker. The accuracy of the threshold is confirmed by examining the overlapping of the raw signal and the identified cell cluster projected onto tissue masks. Examples of general cell populations (e.g., metaclusters) may include, without limitation, macrophages, CD4+ T-cells, CD8+ T-cells, endothelial cells, cholangiocytes, B cells, neutrophils, plasma cells, hepatocytes, monocytes, etc.

By way of example, and not limitation, lineage markers that can be used to identify metaclusters include CD66b, CD20, CD28, CD16, CD163, CD11b, CD45, CD4, CD31, CD279, CD68, Foxp3, CK7, Ki-67, CD8a, Collagen Type I, CD3e, CD138, HLA-DR, Granzyme B, DNA1, DNA2, or any combination thereof. Table 1 shows lineage markers and their corresponding metacluster cell population as a further example. It should be understood that other examples may use different lineage markers to identify metacluster cell populations. The present disclosure contemplates any lineage marker or combination of lineage markers that may be used to identify metacluster cell populations.

TABLE 1

| Lineage Marker | Metacluster |
|---|---|
| CD68 | Macrophages (M1) |
| CD163 | Macrophages (M2) |
| CD31 | Endothelial Cells |
| CK7 | Cholangiocytes |
| CD11b | Monocytes |
| CD20 | B cells |
| CD66b | Neutrophils |
| CD4+ CD3 | CD4 T-cells |
| CD8+ CD3 | CD8 T-cells |
| CD138+ CD45+ HLADR | Plasma cells |
| CD138 | Hepatocytes |

In another example, hepatocytes are identified via negative selection due to the lack of a specific marker in the panel. Thus, cells may be assigned to the hepatocytes compartment if they have low expression of most of the markers or high levels of CD138 only, as Syndecan-1 (CD138) is normally expressed on the hepatocytes surface. After careful examination, any cell not falling under any of the defined metaclusters may be assigned to the hepatocyte compartment. Metacluster labels are verified by reviewing concurrent metacluster label and channel expression on tissue sections, and rules and thresholds are adjusted as needed.

The second part of the IMmuneCite clustering pipeline identifies cell subclusters. This is done on each metacluster individually and can therefore be performed on all metaclusters or a subset of metaclusters. For a particular metacluster, a subset of the data is extracted to include that metacluster only and used for subclustering. The user then has the option of performing unsupervised clustering right away or sub-setting the data even further. For example, for macrophages in human samples, the user may wish to divide all macrophages into M1 and M2 macrophages first using the expression of a particular marker such as CD163 and then perform unsupervised clustering on M1 and M2 macrophages separately. For unsupervised clustering, the user first defines which functional markers are used. For example, for M2 macrophages in human samples, a user may wish to look at CD16, CD11b, Ki67, and HLADR as well as CD68 and CD163. Table 2 shows exemplary lineage markers whose expression is associated with a specific subcluster of cells from a metacluster cell population.

TABLE 2

| Lineage Marker | Metacluster | Functional markers |
|---|---|---|
| CD68 | Macrophages (M1) | Ki67: Proliferating M1 macrophages, HLADR: M1 macrophages, CD11b: CD11b+ M1 macrophages, CD16: CD16+ M1 macrophages, |
| CD163 | Macrophages (M2) | Ki67: Proliferating M2 macrophages, HLADR: HLADR+ M2 macrophages, CD11b: CD11b+ M2 macrophages, CD16: CD16+ M2 macrophages, |
| CD31 | Endothelial Cells | HLADR: HLADR+ Endothelial cells Ki67: Proliferating Endothelial cells |
| CK7 | Cholangiocytes | HLADR: HLADR+ Cholangiocytes Ki67: Proliferating Cholangiocytes |
| CD11b | Monocytes | CD16: Non-classical monocytes, CD16+, CD163+, GranzymeB+: Intermediate monocytes HLADR: Activated monocytes, Ki67: low expression in monocytes |
| CD20 | B cells | Ki67, HLADR+: proliferating B cells, CD279+ and CD45+: PD1+ B cells |
| CD66b | Neutrophils | Granzyme B and Ki67: low expression in Neutrophils |
| CD4+ CD3 | CD4 T-cells | CD4+: Resident memory CD4+ T cells FoxP3+, HLADR+/−: HLADR+/− Tregs, HLADR+ CD4+: Activated CD+ T cells Ki67: Proliferating CD4+ T cells, CD279: PD1+ CD4+ T cells, CD28+ CD45+: naive CD4+ T cells CD16: CD16+ CD4+ T cells, CD3+ CD4+: CD3+ CD4+ T cells |
| CD8+ CD3 | CD8 T-cells | FoxP3, HLADR: low expression in CD8 T cells Ki67: Proliferating CD8 T cells, CD28+ CD45+ CD279: PD1+ CD28+ CD8+ T cells Granzyme B: Cytotoxic T cells, CD45+ CD279+: PD1+ CD8+ T cells CD3+ CD8+: CD8+ T cells |
| CD138+ CD45+ HLADR | Plasma cells | HLADR: Plasma cells |
| CD138 | Hepatocytes | HLADR: HLADR+ Hepatocytes Ki67: Proliferating Hepatocytes |

After defining the markers, unsupervised clustering is performed using the FlowSOM-based algorithm and the expression level of user-defined functional markers, thus providing in-depth information about the multiplexed status of cells within the same metacluster. Examples of subclusters that may be identified from the general cell populations (e.g., metaclusters) include, without limitation, cholangiocytes, endothelial cells, hepatocytes, B cells, proliferating B cells, PD1+ B cells, CD3+ CD4+ T cells, resident memory CD4+ T cells, naïve CD4+ T cells, HLADR+ CD4+ T regulatory cells, HLADR− CD4+ T regulatory cells, PD1+ CD4+ T cells, proliferating CD4+ T cells, activated CD4+ T cells, CD16+ CD4+ T cells, CD3+ CD8+ T cells, cytotoxic T cells, proliferating CD8+ T cells, PD1+ CD8+ T cells, PD1+ CD28+CD8+ T cells, M1 macrophages, proliferating M1 macrophages, CD11b+ M1 macrophages, CD16+ M1 macrophages, M2 macrophages, CD11b+ M2 macrophages, CD16+ M2 macrophages, HLADR+ M2 macrophages, classical monocytes, non-classical monocytes, intermediate monocytes, activated monocytes, neutrophils, and plasma cells.

Figure 4A:
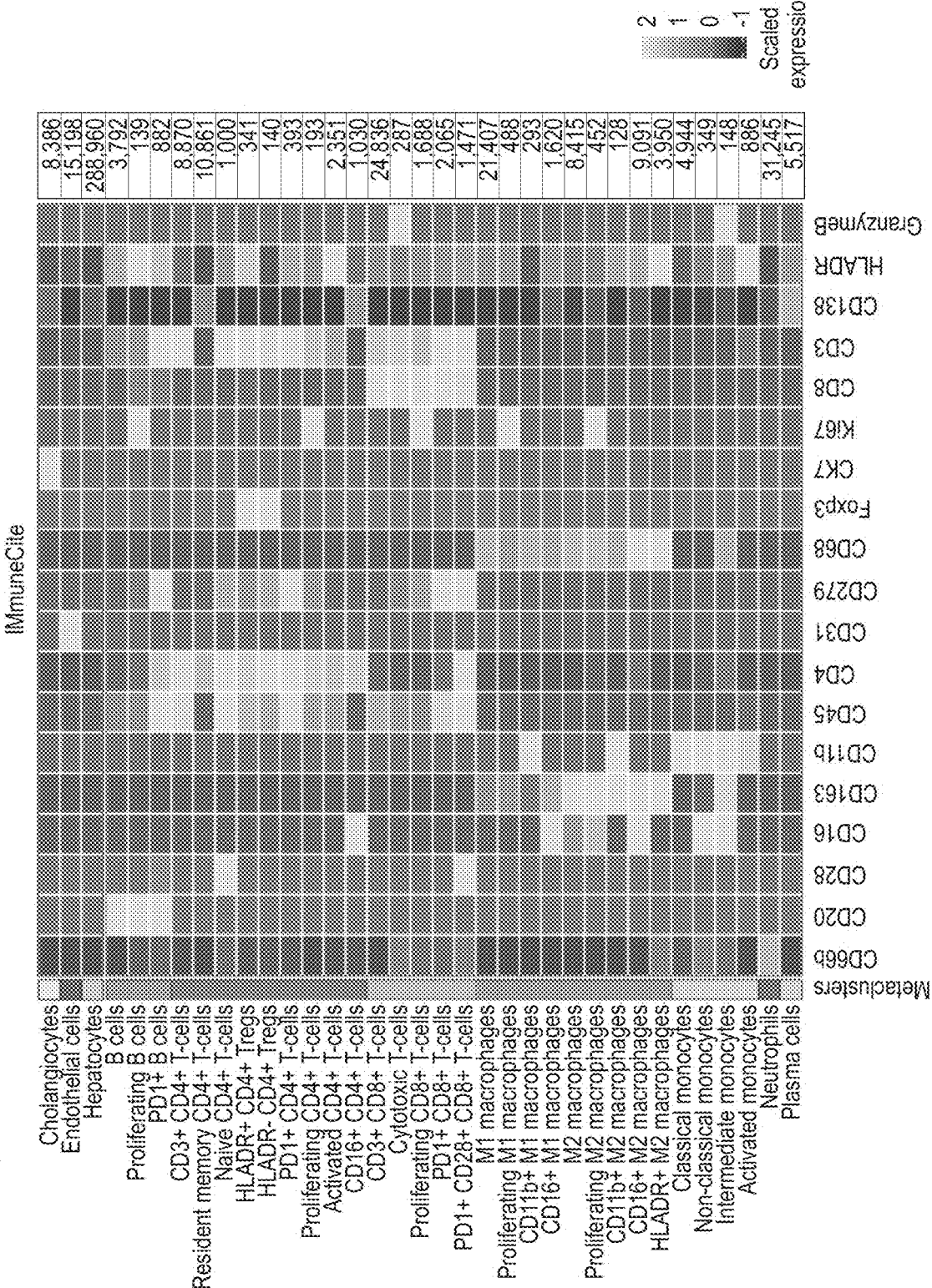
Figure 4C:
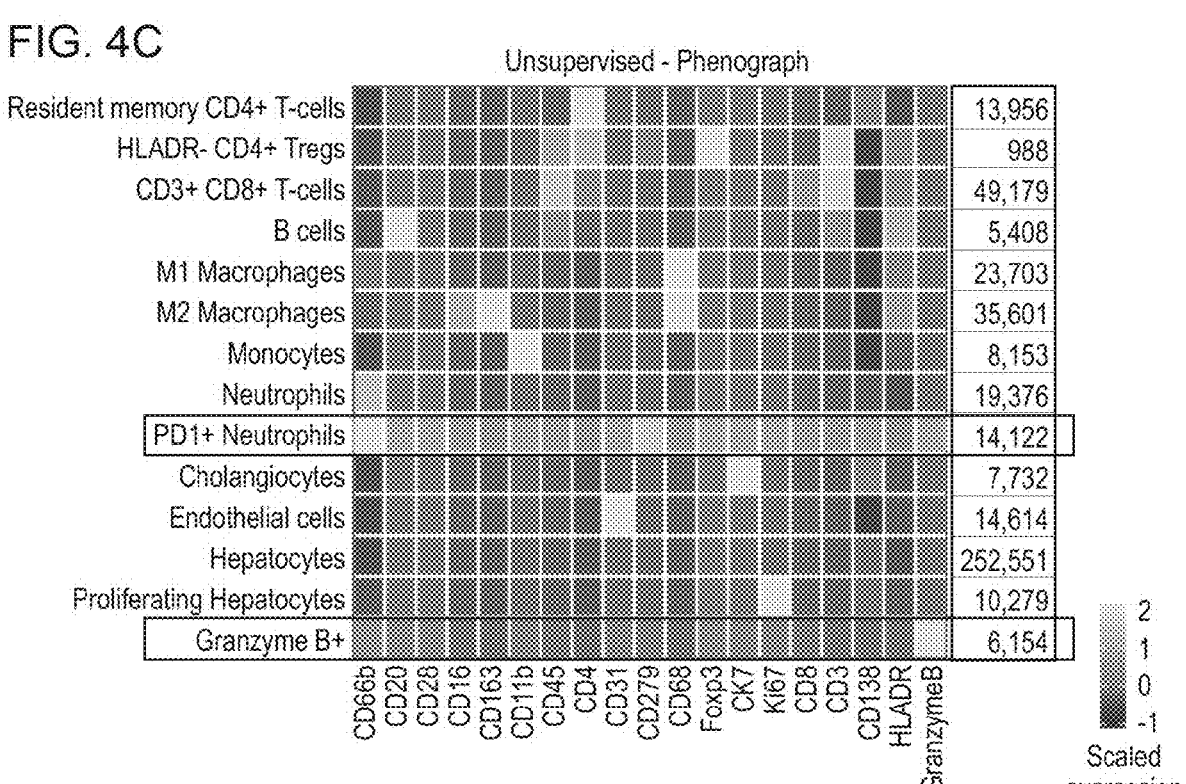

Although default parameters are set to obtain 9 clusters, the user has the option of modifying these parameters to increase or decrease the number of desired clusters. Clusters are then visualized using a heatmap and can be merged and labelled based on their phenotypic expression. By using an unsupervised algorithm and the expression level of user-defined functional markers, the method provides in-depth information about the multiplex status of cells within the same metacluster. Compared to fully unsupervised algorithms, this method allows for a reduction of cells with simultaneous expression of different lineage markers which would result in false annotation or implausible immune cell phenotypes (FIG. 4A). Additionally, this detailed phenotyping has been shown to enable the identification of rare cell populations unique to certain disease states which would otherwise remain unnoticed when using solely unsupervised clustering algorithms (FIG. 4B). Lastly, distinct cell types are used for downstream statistical comparison across different experimental conditions and more advanced spatial analysis (FIG. 3).

After performing subclustering on each desired metacluster, the subcluster data is combined into a single dataset. This step requires the user to manually identify which subclusters to be incorporated and what their final subcluster label are. Here, too, users have the option to exclude cells with a non-biological phenotype. After incorporating all individual information into the main object, the user is advised to visualize the phenotypic expression of all subclusters, both combined and by metacluster, to verify subclusters have been labelled and combined appropriately. Subclusters can also be verified by reviewing concurrent subcluster label and channel expression on tissue sections.

EXAMPLES

The following examples are offered by way of illustration, and not by way of limitation.

This study was approved by the Health Science Campus Institutional Review board of the University of Southern California (HS-18-00708). Given the retrospective nature of this study informed consent was waived.

Spatial proteomics enable detailed analysis of tissue at single cell resolution. However, creating reliable segmentation masks and assigning accurate cell phenotypes to discrete cellular phenotypes is challenging. Disclosed herein is a computational framework (i.e., IMmuneCite) for comprehensive image pre-processing and single-cell dataset creation, focused on defining complex immune landscapes when using spatial proteomics platforms. It was demonstrated that IMmuneCite facilitates the identification of 32 discrete immune cell phenotypes using data from human liver samples while substantially reducing nonbiological cell clusters arising from co-localization of markers for different cell lineages. By applying IMmuneCite to data from murine liver tissue, the versatility and ability of IMmuneCite to accommodate any antibody panel and different species was established. This approach enabled deep characterization of different functional states in each immune compartment, uncovering key features of the immune microenvironment in clinical liver transplantation and murine hepatocellular carcinoma. In conclusion, it was demonstrated that IMmuneCite is a user-friendly, integrated computational platform that facilitates investigation of the immune microenvironment across species, while ensuring the creation of an immune focused, spatially resolved single-cell proteomic dataset to provide high fidelity, biologically relevant analyses.

Example 1: Materials and Experimental Methods

Sample Description

Liver transplant (LT) recipients were retrospectively identified using our institutional transplant database. Patients >18 years at the time of transplant who underwent biopsy of their liver allograft to rule out suspected T-cell mediated rejection (TCMR) or patients with chronic rejection (CR) undergoing re-transplantation between January 2000 and December 2021 met inclusion criteria. Patients were excluded if the histologic diagnosis was associated with reactivation or concurrent viral infection (i.e., Hepatitis C or cytomegalovirus), anatomic causes of graft dysfunction (i.e., vascular stenoses and/or biliary strictures), or advanced fibrosis (bridging fibrosis based on Trichrome staining). Pathology reports were reviewed by a pathologist with expertise in LT to prioritize selection of patients with a rejection activity index (RAI) ≥4 for the TCMR group (n=41 patients, 58 regions of interest (ROIs), median RAI of 5 (Interquartile range (IQR) 5-6)). LT recipients who did not have evidence of rejection on their biopsy (RAI=0) were selected for the no rejection (NR) group (n=24). The CR patients (n=14) were identified at the time of re-transplant for CR with histologic confirmation of CR in the explant.

IMC Staining and Ablation

Formalin-fixed paraffin embedded (FFPE) tissue sections of liver biopsy specimens or explants (4 μm) were selected by the pathologist to identify 1 mm regions of interest for IMC acquisition, focusing on representative periportal regions of the biopsies used in the clinical assessment of RAI. The SC2 Core Facility at Children's Hospital-Los Angeles performed all staining and image acquisition for this study. Slides were stained using a custom 22-marker antibody panel (Table 1). Structural markers included two nuclear intercalator dyes, collagen, CD31 (vascular endothelium), and CK7 (bile ducts). Immune lineage markers included CD3, CD4, CD8, CD20, CD68, CD163, CD66b and CD11b and functional or phenotypic markers included PD1, FoxP3, Ki67, and Granzyme B among others. IMC staining was performed using techniques described in Ung N, Goldbeck C, Man C, et al. Adaptation of Imaging Mass Cytometry to Explore the Single Cell Alloimmune Landscape of Liver Transplant Rejection. Front Immunol. 2022; 13:1363.doi:10.3389/FIMMU.2022.831103/BIBTEX.

Ninety-six ROIs (average of 1.2 ROI/patient) were ablated using the Hyperion Imaging System (Standard Biotools) at a power range of 3.5-4.5 with a laser frequency at 200 Hz. Data were supplied as .txt and .mcd files for use in segmentation and downstream analyses.

Image Pre-Processing Using the IMClean Pipeline

Pre-processing was implemented in three batches by clinical outcome (NR, TCMR, CR) to account for staining differences between disease states. CD68 was used as the 'source' channel for spillover correction; noise removal and channel aggregate removal steps were implemented individually on each channel. After pre-processing, cell segmentation was performed on both the 'raw' and the pre-processed datasets using Mesmer (DeepCell) and following the Bodenmiller Steinbock pipeline.

Phenotypic Clustering Using the IMmune Cite Clustering Pipeline

Cell segmentation outputs were loaded separately into R to perform phenotypic clustering and downstream analysis, first on the raw dataset and then on the pre-processed one. Data were arcsine transformed and standardized by channel to account for differences in signal intensities. Following the IMmuneCite pipeline, 10 lineage markers (CD4, CD8, CD20, CD68, CD163, CD11b, CD66b, CD31, CK7, and CD138) were used to identify the following 10 metaclusters: CD4+ T-cells, CD8+ T-cells, B cells, macrophages, monocytes, plasma cells, neutrophils, endothelial cells, cholangiocytes, and hepatocytes. Labelling accuracy was verified by reviewing concurrent metacluster label and channel expression on tissue sections. Masks were used to visualize cell labels (cytomapper::plotCells). TIFF images were scaled, and channel signals were normalized and visualized individually (cytomapper::plotPixels). Subclustering was subsequently performed on the five most relevant immune metaclusters (CD4+ T-cells, CD8+ T-cells, B cells, macrophages, and monocytes) and the three non-immune metaclusters using a semi-supervised approach. CD8+ T-cell, B cell, monocyte, hepatocyte, endothelial cell, and cholangiocyte subclusters were identified via FlowSOM. For each, the resulting 9 clusters were visualized alongside channel expressions on a heatmap and merged and annotated according to their phenotype. CD4+ T-cells were first divided into CD3 high and CD3 low. FlowSOM clustering was then done on each of the two groups separately. Resulting clusters were merged and annotated to obtain CD4+ T-cell subclusters. The CD4+ Treg subcluster was further divided into HLADR+ CD4+ Tregs and HLADR-CD4+ Tregs. Macrophages were first divided into M1 and M2 macrophages based on their CD163 expression and then clustered separately using FlowSOM to obtain all macrophage subclusters.

Validation Data

A publicly available dataset containing 12 liver samples obtained from mouse HCC (hepatocellular carcinoma) models and stained with a 35-antibody IMC panel was used to validate the IMmuneCluster pipeline. Images were first pre-processed using the IMClean pipeline where CD68 was used as the 'source' channel during channel spillover correction and then the images were segmented. Raw data was also segmented. Raw and pre-processed data were then both loaded into R for single-cell phenotyping using the IMmuneCite clustering algorithm. Metacluster lineage markers include immune markers (CD3, CD4, CD8, B220, CD68, CD11c, F480, CD206, CD11b, Ly6G, MHCII, CD161) and non-immune markers (CD31, CD29, Ecad, aSMA). Functional or phenotypic markers used in subclustering include PD1, FoxP3, Ki67, Granzyme B, PDL1, CD86, S100A9, and S100A4, among others. Identified metaclusters include CD4+ T-cells, CD8+ T-cells, macrophages, myofibroblasts, B cells, dendritic cells, polymorphonuclear cells (PMN), epithelial cells, endothelial cells, and other non-immune cells. Subclustering was performed on select metaclusters (CD4+ T-cells, CD8+ T-cells, macrophages, B cells, and dendritic cells).

Statistical Analysis

Raw and pre-processed data were standardized after integration to allow for better comparison. Signal intensities were compared across the two datasets by channel. Dimensionality reduction was performed using t-Distributed Stochastic Neighbor Embedding (t-SNE) to visualize metacluster differences by clinical outcome across both datasets. Heatmaps were used to visualize phenotype expression by meta- and subcluster across both datasets. To determine differences in cell proportion after pre-processing, the relative change of the median cell proportion by patient (meta- and subcluster) was calculated. Boxplots were used to visualize cell proportion differences by subclusters across both datasets. For each dataset, the positive marker percentage in a particular phenotype was determined. The relative change of these percentages was then used to analyze phenotype sensitivity after pre-processing. The ratio of positive marker percentage within a meta/subcluster vs. all other meta/subclusters was calculated for each dataset. The relative change of the ratios was then used to analyze phenotype specificity after pre-processing. The median fold change was used to calculate the difference in median expression by marker between raw and pre-processed data. The proportion of cells with a mixed phenotype was calculated by analyzing the highest expressing markers in each cell; the relative change was then visualized between raw and pre-processed data. Seeds were set to allow for reproducibility. All statistical tests were carried out in R (v 4.2.2).

Example 2: Quantification of Clustering Recognition Improvement After IMmuneCite Application To evaluate whether the application of IMmuneCite improves image quality and facilitates cluster identification, the workflow was applied to a biobank of human liver rejection samples. This dataset included 96 IMC images comprised of 24 no rejection (NR) liver core biopsies, 41 needle core biopsies with proven acute T-cell mediated rejection (TCMR), and 14 chronic rejection (CR) samples. Formalin-fixed paraffin embedded (FFPE) tissue samples were stained using a customized 22-antibody panel (Table 3).

TABLE 3

| IMC Antibody Panel for Human Liver Tissue | | | | | |
|---|---|---|---|---|---|
| Metal tag | Marker | Clone | Source | Catalog # | Dilution |
| 139La | CD66b | G10F5 | Biolegend | 305102 | 75 |
| 142Nd | CD20 | L26 | Thermo. Scientific | 14-0202-82 | 600 |
| 144Nd | CD28 | EPR22076 | Abcam | GR3252786-4 | 100 |
| 146Nd | CD16 | EPR16784 | Standard biotools | 3146020D | 100 |
| 147Sm | CD163 | Edhu-1 | Standard biotools | 3147021D | 500 |
| 149Sm | CD11b | EPR1344 | Standard biotools | 3149028D | 400 |
| 152Sm | CD45 | CD45-2B11 | Standard biotools | 3152018D | 100 |
| 153Eu | CD4 | EPR68551 | Abcam | ab181724 | 100 |
| 154Sm | CD31 | C31.3 | Novus | NBP2-33154 | 1000 |
| 156Gd | CD279 (PD-1) | NAT105 | Biolegend | 367402 | 50 |
| 159Tb | CD68 | KP1 | Standard biotools | 3159035D | 200 |
| 160Gd | Foxp3 | 236A/E7 | Abcam | ab96048 | 75 |
| 164Dy | CK7 | RCK105 | Standard biotools | 3164020A | 50 |
| 167Er | Ki-67 | B56 | BD Pharmingen | 624084 | 1000 |
| 168Er | CD8a | C8/144B | Biolegend | 372902 | 250 |
| 169Tm | Collagen Type I | Goat polyclonal | Standard biotools | 3169023D | 250 |
| 170Er | CD3e | Polyclonal | Standard biotools | 3170007B | 200 |
| 172Yb | CD138 | 4F3A8 | Proteintech | 67155-1-Ig | 6000 |
| 174Yb | HLA-DR | LN3 | Standard biotools | 3174025D | 800 |
| 175Lu | Granzyme B | EPR20129-217 | Abcam | ab219803 | 500 |
| 191Ir | DNA1 | — | Standard biotools | 201192A | 800 |
| 193Ir | DNA2 | — | Standard biotools | 201192A | 800 |

Figure 5D:
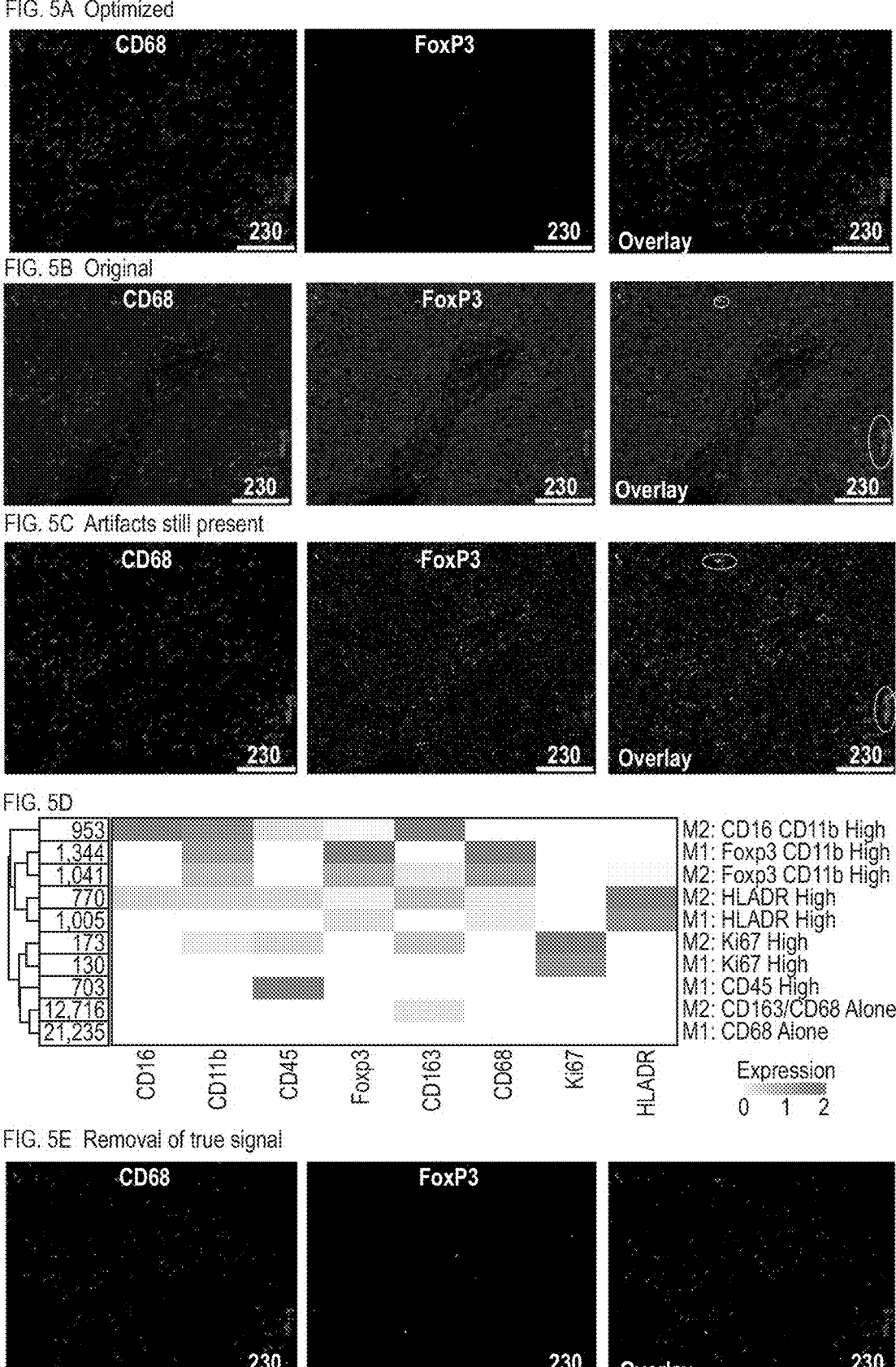

Multiplexed images were used to generate two distinct single-cell datasets for comparison. The first dataset (461,816 cells) was obtained after pre-processing all IMC images using IMClean, the first step in the IMmuneCite workflow. Channel crosstalk correction was performed utilizing CD68 as the contaminating marker, followed by denoising and aggregates removal for each of the markers in the panel (FIG. 3). The image artifacts correction for each channel was optimized (FIG. 5A-5E). Thus, true marker signal was enhanced but not removed (FIG. 5A). For example, both raw images and images where artifacts were not properly corrected, still presented CD68 and FoxP3 signal overlap, which resulted in the presence of FoxP3+ macrophages (FIG. 5B-D). Conversely, an aggressive correction resulted in the removal of true signal, affecting overall macrophage identification (FIG. 5E).

Figure 4D:
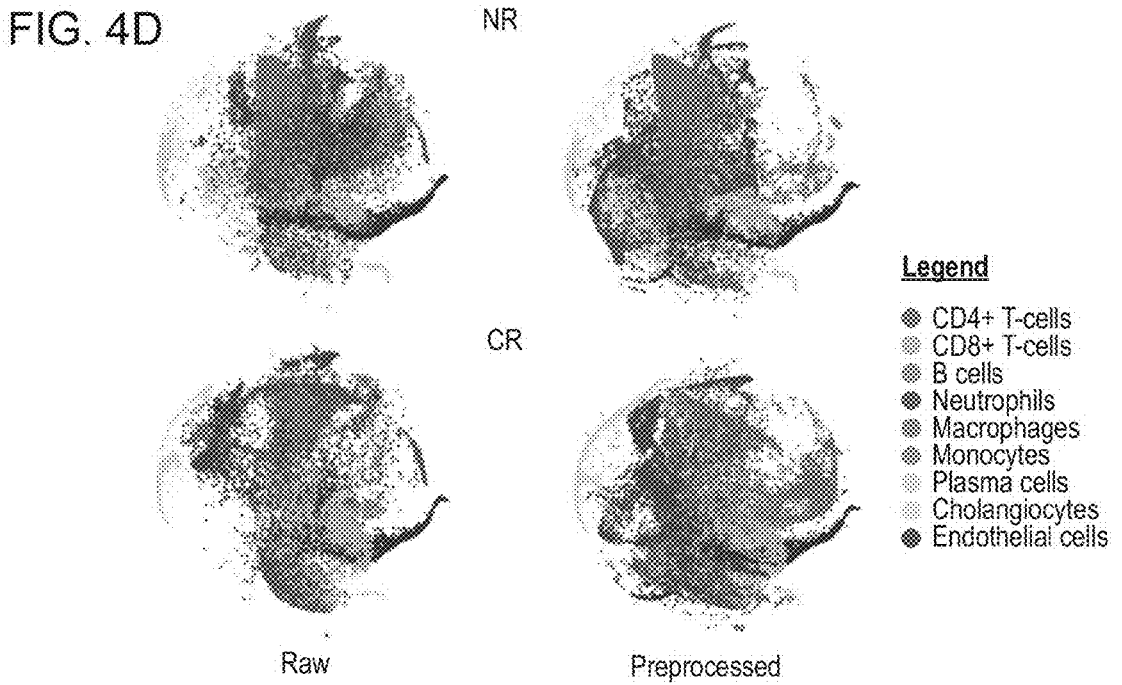
Figures 6E, 6F:

The second database was obtained by segmenting the same 96 raw images with no correction of artifacts and contained a total of 402,287 cells. Correlation analysis showed that a similar number of cells was obtained after segmentation of raw vs. pre-processed IMC data (Spearman correlation=0.97). Subsequently, the cell phenotype identification algorithm was applied to both datasets to identify metaclusters and subclusters (FIG. 6A-6F). The thresholds for the lineage markers were optimized for each dataset separately to guarantee the most reliable cell phenotyping in each condition. By visually inspecting the signal of multiple markers in raw vs. pre-processed images and the corresponding clusters on image masks, an improvement of image quality was observed, which enhanced metacluster identification (FIG. 6A). Additionally, an improved overlapping between lineage marker signal and the corresponding cell plotted on the segmented tissue mask was observed in IMClean-processed images (FIG. 6A). Differences between the two datasets in cell distribution and density for each assigned phenotype is also visible when data are plotted in two dimensions using t-SNE (FIG. 6B and FIG. 4D). After IMClean pre-processing, a decrease was observed in the following metaclusters: CD4+ T-cells (22%), CD8+ T-cells (18%), B cells (84%), monocytes (58%), cholangiocytes (12%), and endothelial cells (19%). Conversely, macrophages, plasma cells, and neutrophils increased by 26%, 70%, and 5%, respectively (FIG. 6C).

How IMClean changes the marker expression pattern within each metacluster was investigated. In the pre-processed dataset, a positive percentage of cells expressing phenotype-specific markers in each metacluster was observed, while the percentage of markers not related to the phenotype was minimal (FIG. 6D, circle size). For example, cells in the CD4+ T-cell population positively expressed both CD4 and CD3. Similarly, cells in the CD8+ T-cell metacluster were positively expressing CD8 and CD3 and cells in the macrophage metacluster were positively expressing CD68, CD163, HLADR (Human leukocyte antigen-DR), and CD16. On the other hand, the proportion of cells expressing markers not specific to these metaclusters such as CD20, CD31, and CK7 was near zero. When compared to the raw dataset, an overall decrease in relative change after pre-processing in the proportion of cells expressing unspecific markers for each metacluster (FIG. 6D, color scale) was observed. This suggests that IMClean increased the sensitivity of phenotyping.

Additionally, after image pre-processing, the expression of each marker was enriched in the specific cell phenotype while decreased in other non-specific phenotypes, suggesting an increased specificity of the phenotypic marker for each metacluster (FIG. 6E, Table 4).

TABLE 4

| Relative change in marker expression by metacluster | | | | |
|---|---|---|---|---|
| Variable | Clusters | Ratio Raw | Ratio Processed | Ratio Relative Change | Change |
| CD11b | B cells | 1.7% | 1.2% | −0.31% | DOWN |
| CD11b | CD4+ T-cells | 10.3% | 4.7% | −0.54% | DOWN |
| CD11b | CD8+ T-cells | 10.2% | 10.0% | −0.01% | DOWN |
| CD11b | Cholangiocytes | 2.5% | 2.0% | −0.22% | DOWN |
| CD11b | Endothelial cells | 4.3% | 2.3% | −0.47% | DOWN |
| CD11b | Hepatocytes | 45.9% | 34.8% | −0.24% | DOWN |
| CD11b | Macrophages | 14.1% | 16.2% | 0.15% | UP |
| CD11b | Monocytes | 4.8% | 23.5% | 3.94% | UP |
| CD11b | Neutrophils | 5.3% | 5.1% | −0.03% | DOWN |
| CD11b | Plasma cells | 0.9% | 0.1% | −0.86% | DOWN |
| CD163 | B cells | 1.5% | 0.5% | −0.65% | DOWN |
| CD163 | CD4+ T-cells | 10.0% | 4.4% | −0.56% | DOWN |
| CD163 | CD8+ T-cells | 14.2% | 9.9% | −0.30% | DOWN |
| CD163 | Cholangiocytes | 0.7% | 0.2% | −0.69% | DOWN |
| CD163 | Endothelial cells | 3.5% | 1.6% | −0.53% | DOWN |
| CD163 | Hepatocytes | 38.6% | 32.3% | −0.16% | DOWN |
| CD163 | Macrophages | 24.2% | 48.0% | 0.98% | UP |
| CD163 | Monocytes | 2.8% | 0.9% | −0.66% | DOWN |
| CD163 | Neutrophils | 3.5% | 1.6% | −0.55% | DOWN |
| CD163 | Plasma cells | 1.0% | 0.5% | −0.51% | DOWN |
| CD20 | B cells | 3.0% | 36.4% | 11.31% | UP |
| CD20 | CD4+ T-cells | 8.2% | 8.0% | −0.03% | DOWN |
| CD20 | CD8+ T-cells | 8.9% | 13.2% | 0.48% | UP |
| CD20 | Cholangiocytes | 1.9% | 0.3% | −0.82% | DOWN |
| CD20 | Endothelial cells | 4.4% | 3.1% | −0.30% | DOWN |
| CD20 | Hepatocytes | 54.8% | 32.9% | −0.40% | DOWN |
| CD20 | Macrophages | 8.8% | 1.6% | −0.82% | DOWN |
| CD20 | Monocytes | 2.1% | 0.8% | −0.64% | DOWN |
| CD20 | Neutrophils | 7.2% | 3.6% | −0.51% | DOWN |
| CD20 | Plasma cells | 0.8% | 0.1% | −0.82% | DOWN |
| CD3 | B cells | 3.2% | 4.5% | 0.40% | UP |
| CD3 | CD4+ T-cells | 15.7% | 17.4% | 0.11% | UP |
| CD3 | CD8+ T-cells | 21.6% | 37.9% | 0.76% | UP |
| CD3 | Cholangiocytes | 1.5% | 0.9% | −0.42% | DOWN |
| CD3 | Endothelial cells | 5.3% | 4.3% | −0.18% | DOWN |
| CD3 | Hepatocytes | 34.6% | 18.2% | −0.47% | DOWN |
| CD3 | Macrophages | 9.2% | 8.4% | −0.09% | DOWN |
| CD3 | Monocytes | 3.1% | 2.4% | −0.24% | DOWN |
| CD3 | Neutrophils | 5.1% | 5.4% | 0.05% | UP |
| CD3 | Plasma cells | 0.7% | 0.6% | −0.14% | DOWN |
| CD4 | B cells | 2.2% | 2.1% | −0.02% | DOWN |
| CD4 | CD4+ T-cells | 13.4% | 28.4% | 1.12% | UP |
| CD4 | CD8+ T-cells | 10.8% | 13.6% | 0.26% | UP |
| CD4 | Cholangiocytes | 0.9% | 0.4% | −0.59% | DOWN |
| CD4 | Endothelial cells | 4.2% | 2.1% | −0.49% | DOWN |
| CD4 | Hepatocytes | 46.7% | 41.8% | −0.11% | DOWN |
| CD4 | Macrophages | 12.9% | 8.2% | −0.37% | DOWN |
| CD4 | Monocytes | 2.6% | 1.0% | −0.61% | DOWN |
| CD4 | Neutrophils | 5.4% | 2.1% | −0.62% | DOWN |
| CD4 | Plasma cells | 0.9% | 0.4% | −0.56% | DOWN |
| CD66b | B cells | 1.9% | 0.7% | −0.66% | DOWN |
| CD66b | CD4+ T-cells | 7.9% | 2.8% | −0.65% | DOWN |
| CD66b | CD8+ T-cells | 9.5% | 6.0% | −0.37% | DOWN |
| CD66b | Cholangiocytes | 1.8% | 0.9% | −0.51% | DOWN |
| CD66b | Endothelial cells | 4.3% | 2.1% | −0.50% | DOWN |
| CD66b | Hepatocytes | 52.0% | 54.2% | 0.04% | UP |
| CD66b | Macrophages | 10.2% | 6.4% | −0.37% | DOWN |
| CD66b | Monocytes | 2.4% | 1.5% | −0.39% | DOWN |
| CD66b | Neutrophils | 9.1% | 25.2% | 1.77% | UP |
| CD66b | Plasma cells | 0.9% | 0.3% | −0.63% | DOWN |
| CD68 | B cells | 1.5% | 0.2% | −0.84% | DOWN |
| CD68 | CD4+ T-cells | 9.3% | 2.4% | −0.74% | DOWN |
| CD68 | CD8+ T-cells | 10.8% | 7.3% | −0.32% | DOWN |
| CD68 | Cholangiocytes | 2.2% | 0.4% | −0.84% | DOWN |
| CD68 | Endothelial cells | 4.9% | 1.0% | −0.79% | DOWN |
| CD68 | Hepatocytes | 48.2% | 37.2% | −0.23% | DOWN |
| CD68 | Macrophages | 14.6% | 49.6% | 2.41% | UP |

TABLE 4-continued

Relative change in marker expression by metacluster

| Variable | Clusters | Ratio Raw | Ratio Processed | Ratio Relative Change | Change |
|---|---|---|---|---|---|
| CD68 | Monocytes | 2.9% | 0.6% | −0.81% | DOWN |
| CD68 | Neutrophils | 4.7% | 1.0% | −0.79% | DOWN |
| CD68 | Plasma cells | 1.0% | 0.3% | −0.69% | DOWN |
| CD8 | B cells | 2.0% | 2.0% | −0.01% | DOWN |
| CD8 | CD4+ T-cells | 12.0% | 3.2% | −0.73% | DOWN |
| CD8 | CD8+ T-cells | 20.8% | 53.9% | 1.60% | UP |
| CD8 | Cholangiocytes | 1.6% | 1.3% | −0.20% | DOWN |
| CD8 | Endothelial cells | 3.9% | 2.9% | −0.26% | DOWN |
| CD8 | Hepatocytes | 42.0% | 26.9% | −0.36% | DOWN |
| CD8 | Macrophages | 9.4% | 6.3% | −0.34% | DOWN |
| CD8 | Monocytes | 2.3% | 1.1% | −0.55% | DOWN |
| CD8 | Neutrophils | 5.4% | 1.9% | −0.64% | DOWN |
| CD8 | Plasma cells | 0.6% | 0.4% | −0.20% | DOWN |
| CK7 | B cells | 1.6% | 0.1% | −0.91% | DOWN |
| CK7 | CD4+ T-cells | 8.3% | 0.8% | −0.91% | DOWN |
| CK7 | CD8+ T-cells | 10.0% | 3.1% | −0.69% | DOWN |
| CK7 | Cholangiocytes | 4.3% | 69.3% | 15.12% | UP |
| CK7 | Endothelial cells | 4.5% | 1.7% | −0.63% | DOWN |
| CK7 | Hepatocytes | 48.5% | 18.3% | −0.62% | DOWN |
| CK7 | Macrophages | 10.1% | 0.9% | −0.91% | DOWN |
| CK7 | Monocytes | 2.4% | 0.6% | −0.75% | DOWN |
| CK7 | Neutrophils | 9.6% | 4.7% | −0.51% | DOWN |
| CK7 | Plasma cells | 0.8% | 0.6% | −0.24% | DOWN |

For instance, post-IMClean, an increased ratio of CD20-expressing cells in the B cell metacluster (relative change=+11.31%) was observed, while the proportion of CD20-expressing cells decreased in the other metaclusters. Similarly, CD66b-expressing cells were enriched in neutrophils (+1.77%), while the proportion of CD66b-expressing cells was reduced in other metaclusters. CD68, CD163, and CD16-expressing cells all increased in the macrophage metacluster (+2.41%, +0.98%, and +0.9%, respectively), while the proportion of cells expressing these markers largely decreased in the other metaclusters. The ratio of CD11b-expressing cells increased in the monocyte metacluster (+3.94%), while it decreased in other metaclusters. A greater proportion of CD4 and CD8-expressing cells in the corresponding metaclusters (+1.12% and +1.60%, respectively) was observed, while their expression decreased in other cell phenotypes. However, a small percentage of CD3-expressing cells in the B cell metacluster (+0.40%) and a small percentage of CD8-expressing cells in CD4+ T-cell compartment (+0.26%) was noted. This is likely due to the close proximity of those cells in immune enriched tissue as is the case of TCMR post-liver transplant, which causes lateral spillover of the signal from one cell mask into the adjacent cell mask. Also observed were increased ratios of CK7-expressing cells in the cholangiocyte metacluster (+15.12%) and CD31-expressing cells in the endothelial cell compartment (+3.9%). Lastly, for markers not restricted to a single cell lineage, an overall positive relative change in biologically appropriate metaclusters was observed, with few exceptions such as CD28, perhaps due to the poor staining observed for this antibody (FIG. 6E).

Whether IMClean reduced the frequency of cells showing mixed phenotypes, defined as cells expressing high level of two different lineage markers, was evaluated. Multiple lineage markers would lead to a conflictive assignment of cell phenotype, and thus a potential false annotation. IMClean reduced the frequency of mixed phenotypes, with a reduction of 74.3% in the co-expression of B and T cell markers (CD4 or CD8). Similarly, the co-expression of CD3 and CD20 had a 25.5% reduction after image pre-processing (FIG. 6F).

Figure 7A:
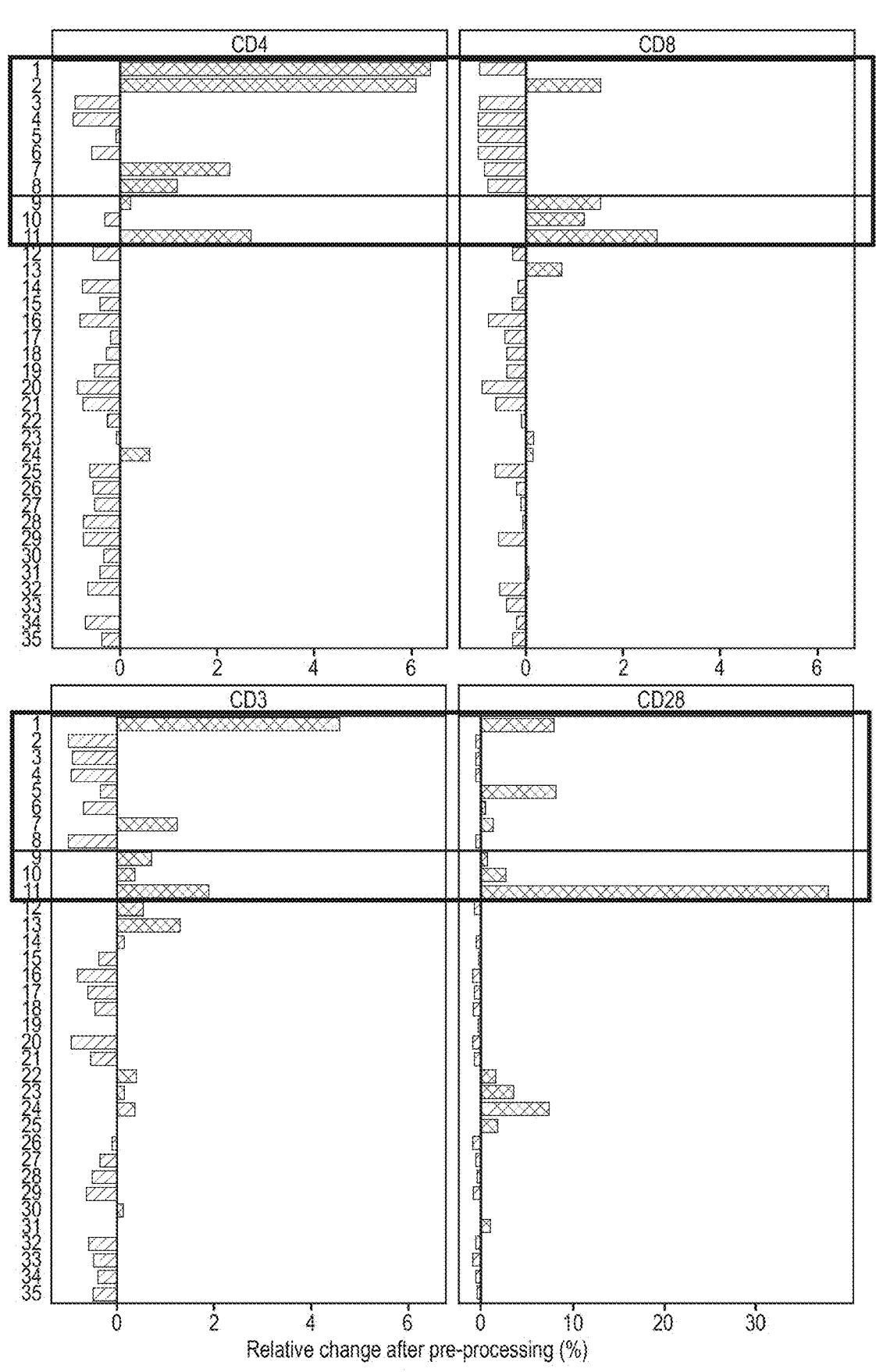
Figure 7A:
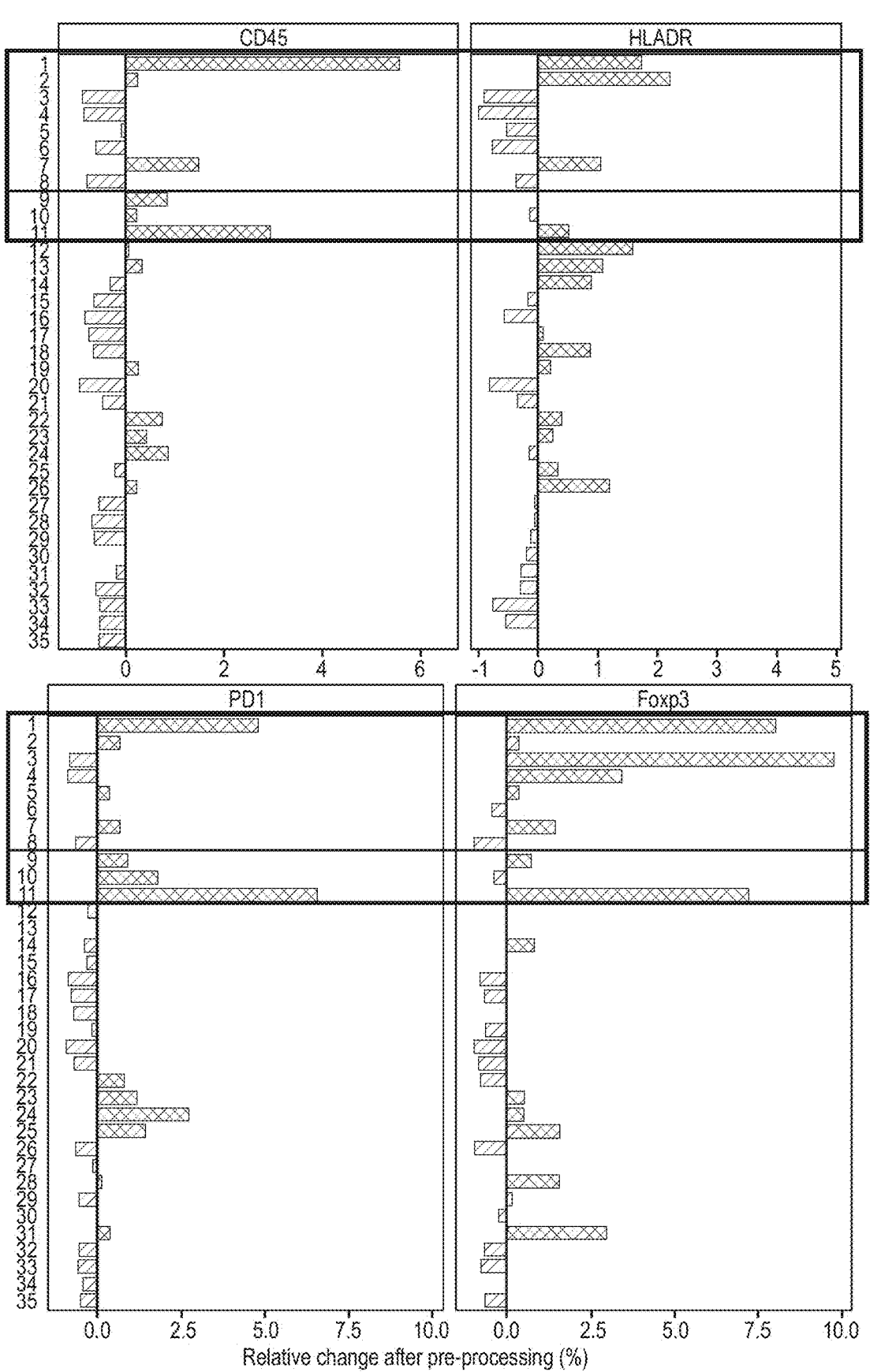
Figure 7A:
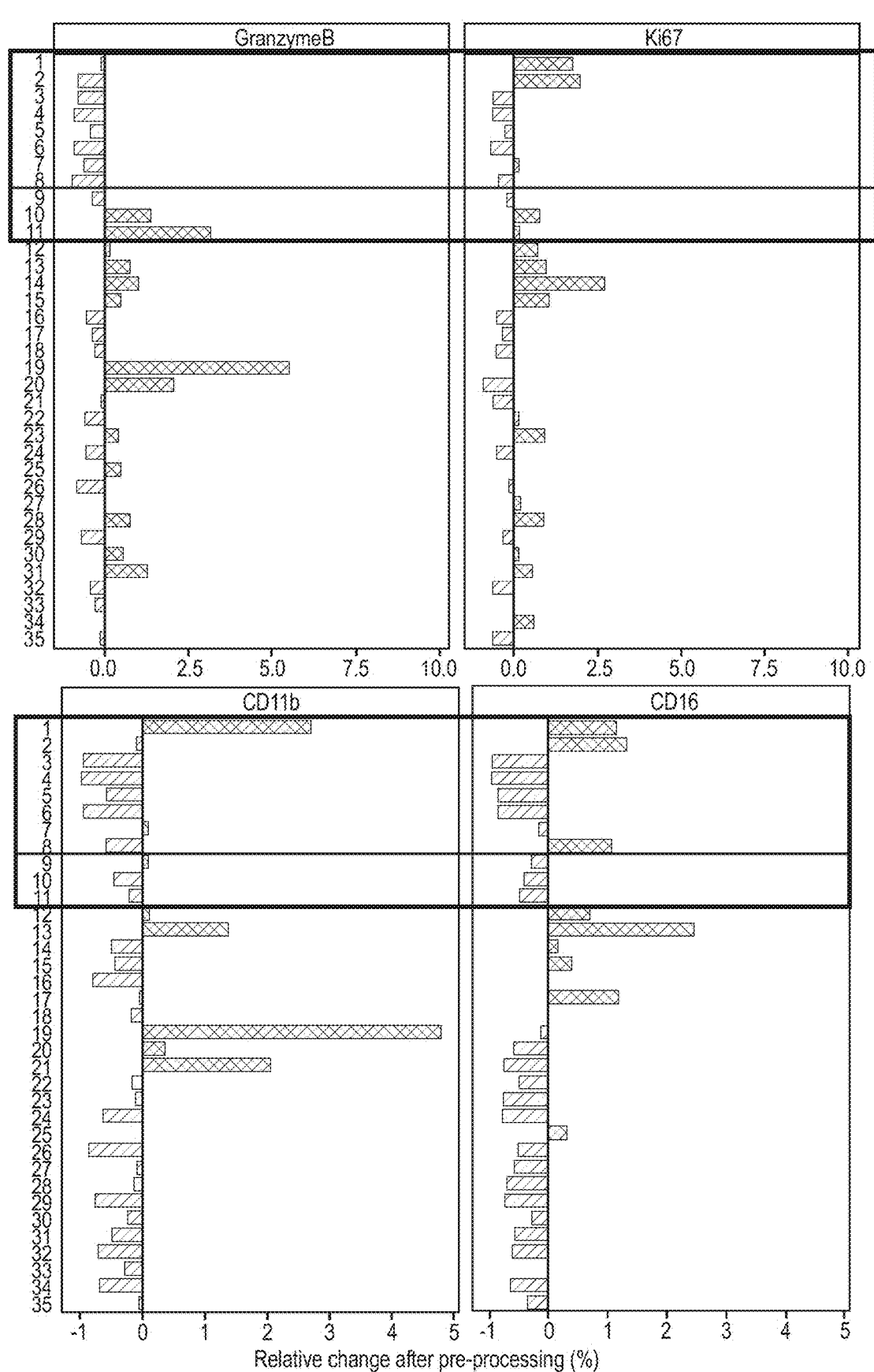
Figure 7E:
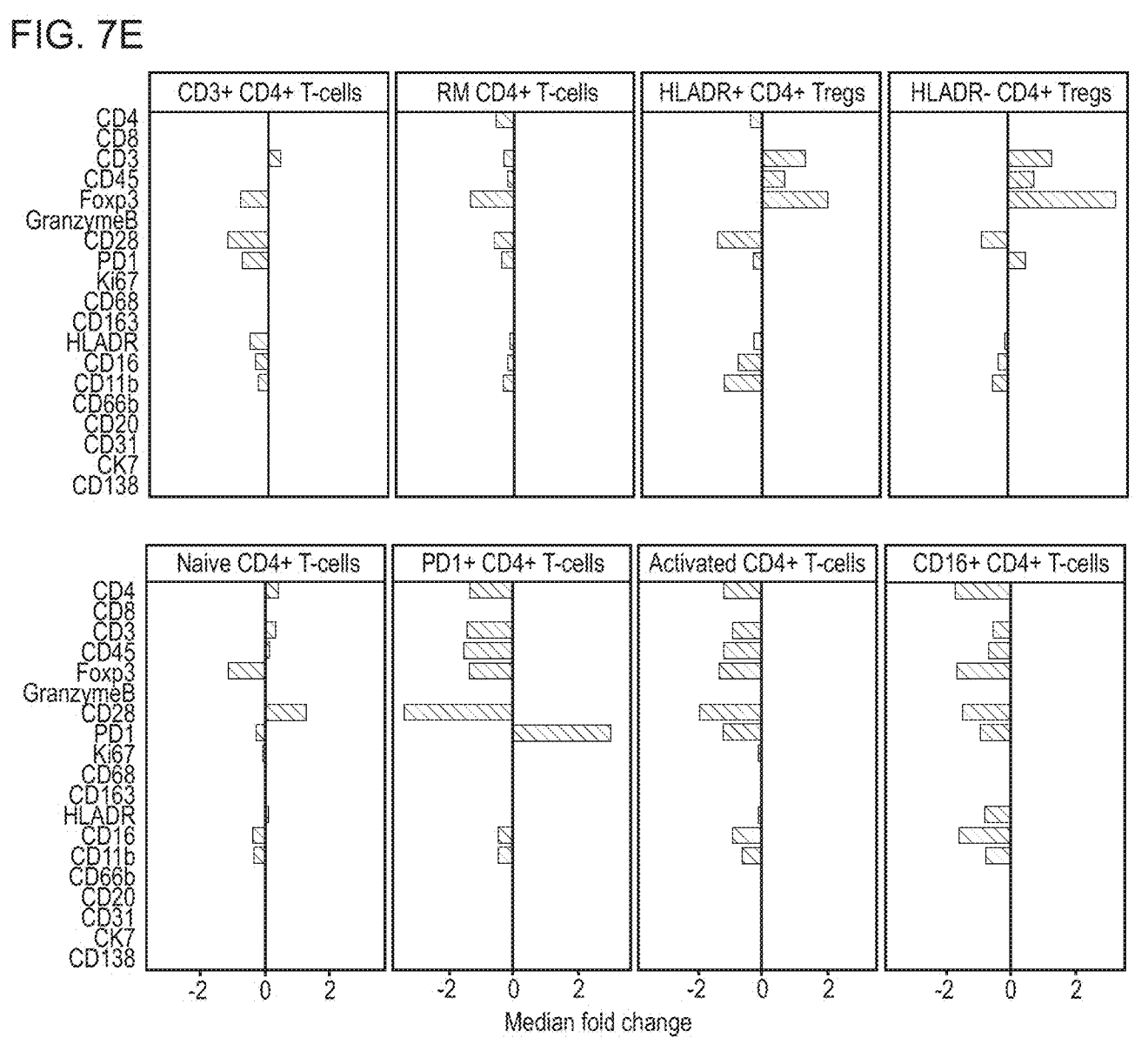
Figure 8A:
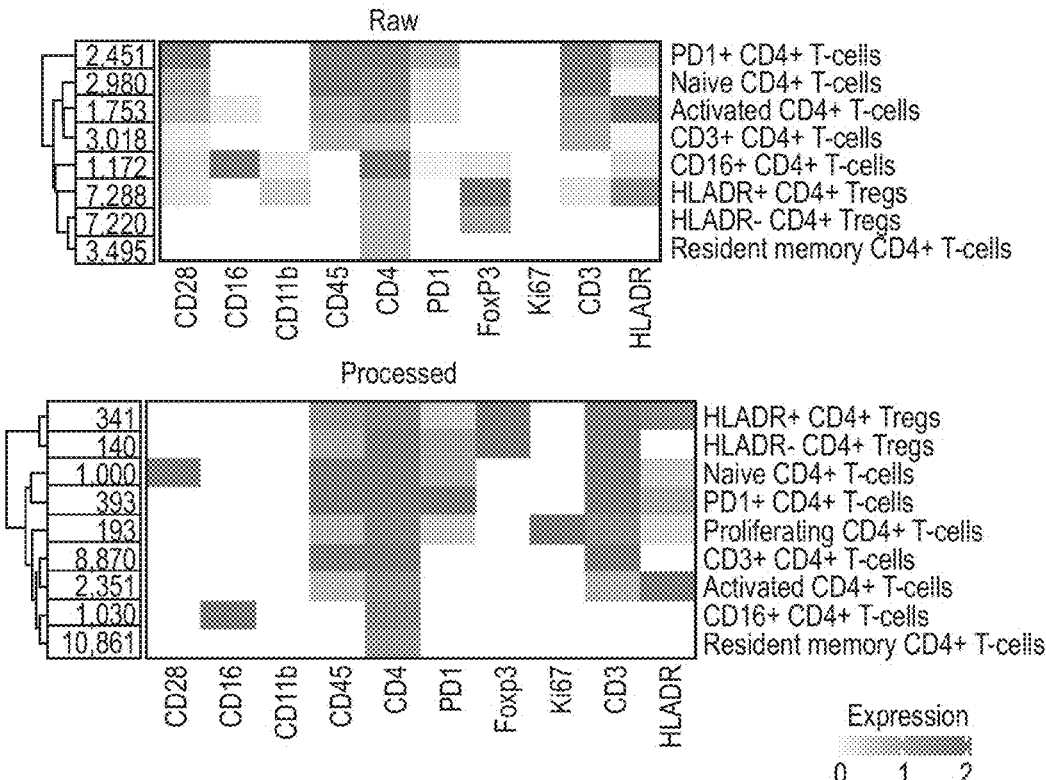
Figure 8B:
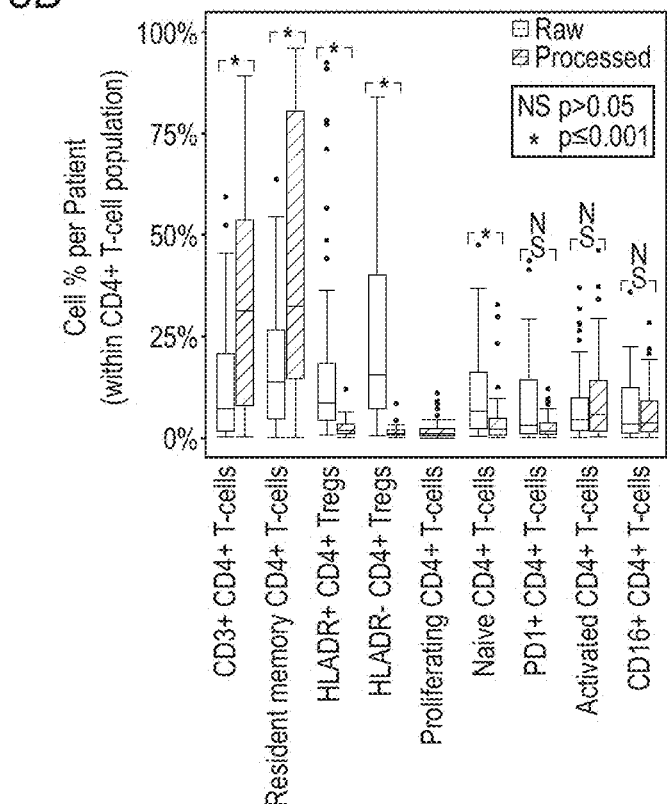

Example 3: IMmuneCite Facilitates the Identification of T Cell, B Cell and Monocyte-Macrophage Subclusters Offering Detailed Description of Cell States in Human Liver Rejection Samples Spatial proteomics, and in particular IMC, have been primarily applied to study the complexity of the tumor microenvironment. Thus, being able to dissect the multiplicity of all immune cell phenotypes remains the principal scope of this technology, especially when applied to inflammatory and immune-mediated diseases, where uncovering rare cell types might be crucial. To assess whether IMClean affects the identification of immune cell subpopulations, the IMmuneCite subclustering algorithm was applied to the CD4+ and CD8+ T-cell, B-cell, macrophage, and monocyte metaclusters, and compared the results between raw and pre-processed data (FIGS. 7A-7E and FIGS. 8A-8E). Eight different CD4+ T-cell subclusters in the raw data and nine subclusters in the pre-processed data were identified, with eight subclusters showing the same marker expression profile (FIG. 7A, FIG. 8A). The frequency of these CD4+ T-cell subpopulations in the pre-processed vs. the raw data was also calculated (FIG. 8B). Similarly, four CD8+ T-cell subclusters were identified within the raw dataset and five different CD8+ T-cell subtypes in the IMClean-processed data (FIG. 7A and FIGS. 8C and 8D). When assessing the expression of both lineage and functional markers, these were enriched in the specific cell phenotype while decreased in other non-specific phenotypes, suggesting an increase in phenotype specificity (FIG. 7A). For example, the ratio of CD4 and Foxp3-expressing cells increased the most in CD4+ T-cell subclusters such as CD3+ CD4+ T-cells and CD4+ Tregs, the proportion of CD8-expressing cells increased most in CD8+ T-cell subclusters, CD3 and CD45-expressing cells increased the most in T-cell subclusters, and the ratio of PD1 (programmed death 1)-expressing cells increased mostly in PD1+ subclusters. Conversely, the ratio of CD4, CD8, CD3, and CD45-expressing cells mostly decreased in non-T-cells. Additionally, the increased ratio of CD11b-expressing cells in CD3+CD4+ T-cells is in agreement with their recent recruitment and activation at the inflammatory site. Tissue sections showing the spatial distribution of these subclusters are presented in FIG. 7B and FIG. 7C. After IMClean pre-processing, an enrichment of specific markers in each subcluster was noticed, while the expression of markers not specific for the subclusters decreased (FIG. 7D). For example, activated CD4+ T-cells showed an increase in cells expressing HLADR, CD3, CD4, and CD45, while proliferating CD8+ T-cells observed an increase in cells expressing Ki67. The median fold change for all markers for each CD4+ T-cell (FIG. 7E) and CD8+ T-cell subcluster (FIG. 8E) was evaluated and showed a greater median expression of specific markers after IMClean pre-processing (FIG. 7E). For instance, after pre-processing, the median expression of PD1 and Foxp3 increased in PD1+ CD4+ T-cells and Tregs, respectively.

Figure 9A:
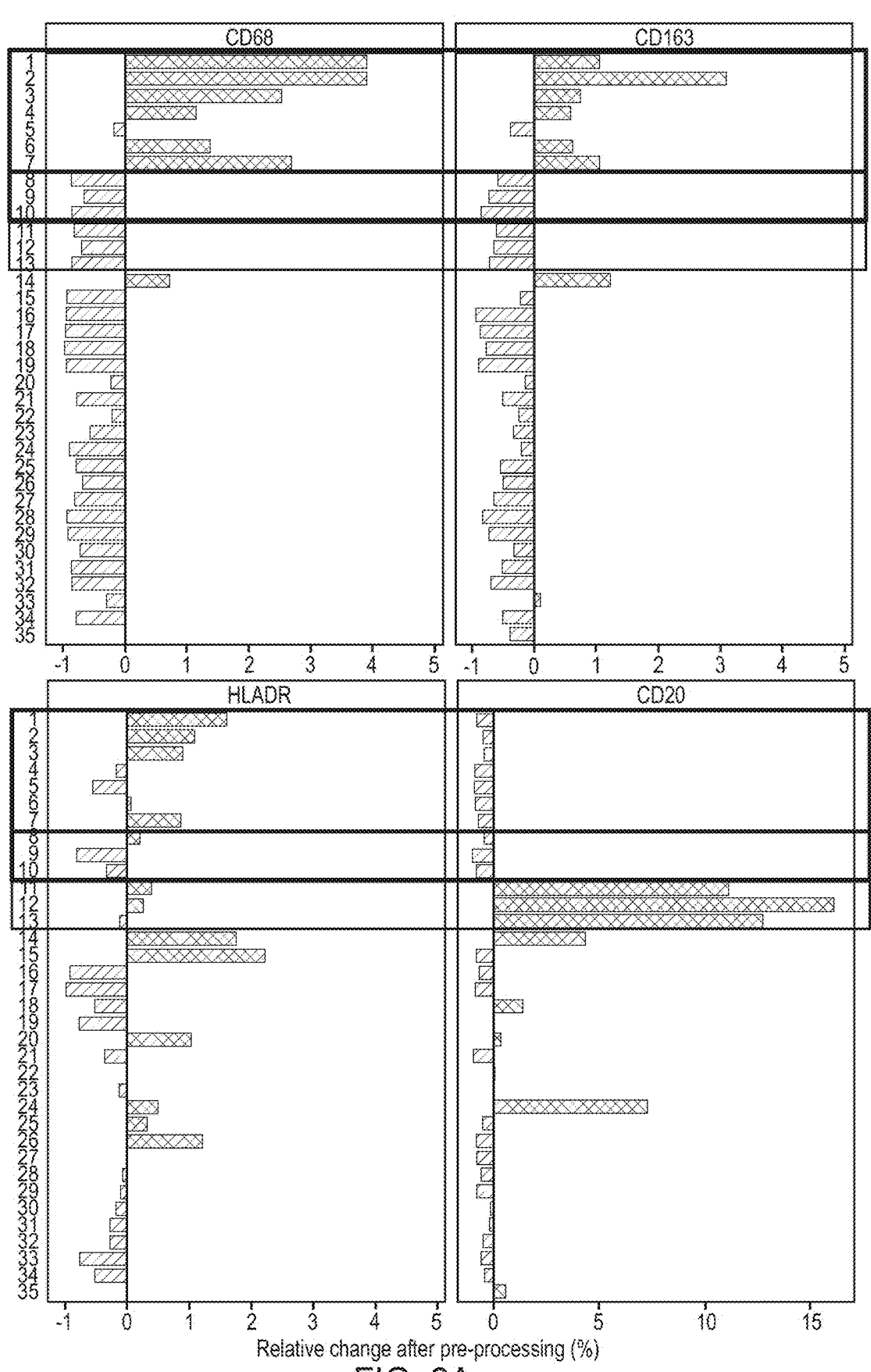
Figures 10A, 10B:
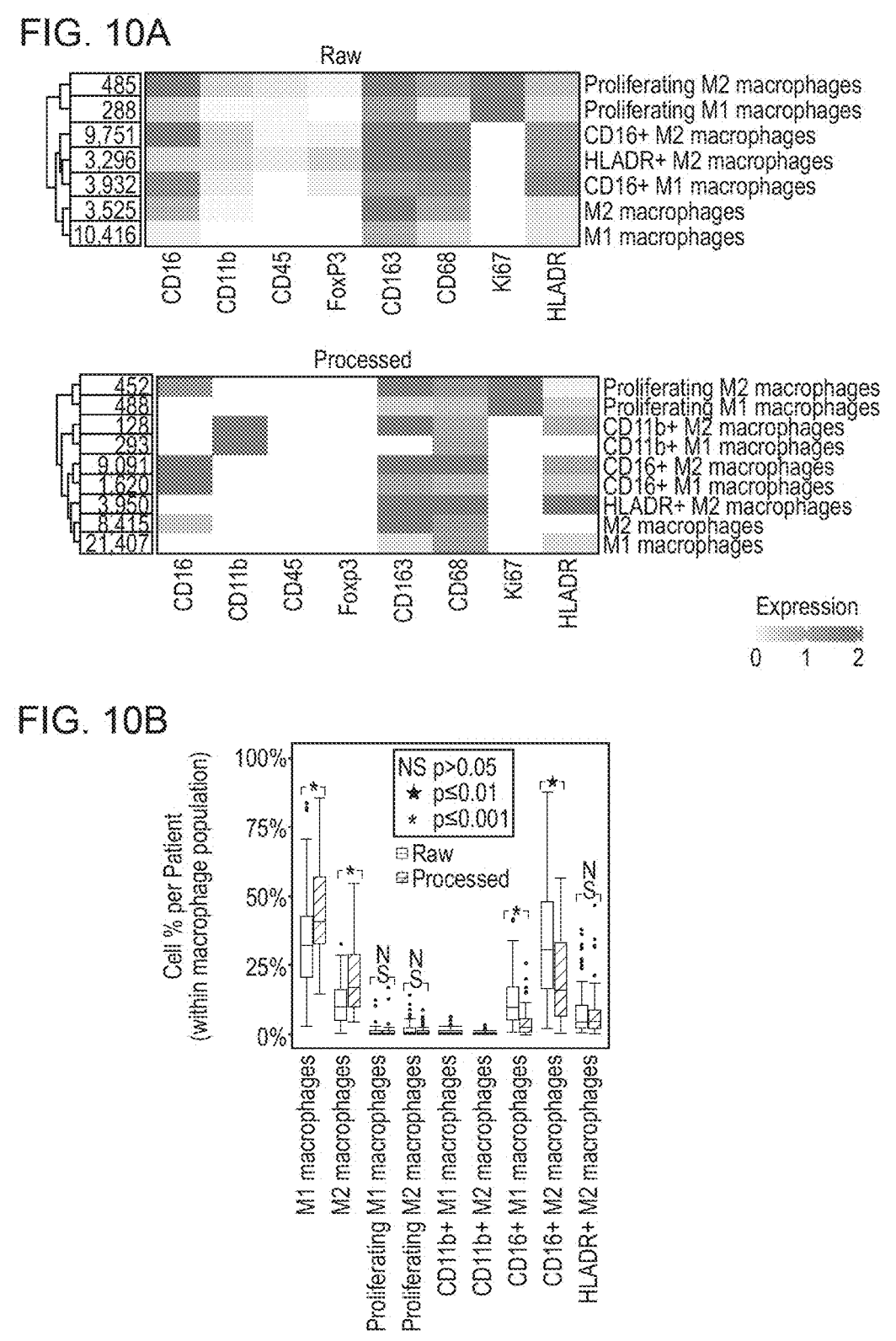

Differences in the expression patterns of all markers between the raw and IMClean-processed datasets after applying our IMmuneCite subclustering algorithm to cells within the macrophage, monocyte, and B-cell compartments (FIGS. 9A-9H and FIGS. 10A-10F). Seven different subtypes of macrophages in the raw dataset while nine macrophage subclusters were detected in the IMClean-processed dataset, with a different percentage distribution (FIGS. 10A and 10B). Four different monocyte subtypes were identified in both datasets, with a greater frequency of classical monocytes found in pre-processed data (FIGS. 10C and D). The same three B-cell subtypes were identified in both datasets (FIGS. 10E and 10F). Similar to what was observed in the T-cell compartments, an increase in phenotype specificity (FIG. 9A) was observed. The ratio of CD11b-expressing cells was mostly enriched in monocyte subclusters: +2.06% in activated monocytes, +4.80% in classical monocytes, and +0.35% in intermediate monocytes (FIG. 9A). The ratio of cells expressing PD1 increased in B cell subclusters while decreasing in all non-B and non-T-cell subclusters (FIG. 9A). The phenotypes commonly identified in raw and IMClean-processed datasets were mapped back onto their segmentation masks (FIG. 9B-9D). Furthermore, after the IMClean pre-processing, each subcluster had an increased expression rate of cells expressing biologically relevant markers, while the non-specific markers were reduced (FIG. 9E, color scale). For example, proliferating macrophages and proliferating B-cells showed an increase in cells expressing Ki67, while non-specific markers such as PD1 and CD11b were reduced. The median fold change of marker expression after pre-processing for macrophages, monocytes, and B-cells (FIG. 9F-H) was evaluated. Taken together, these results show the robustness of the IMmuneCite workflow to generate biologically accurate outputs when applied to human immunology experiments.

Figure 9A:
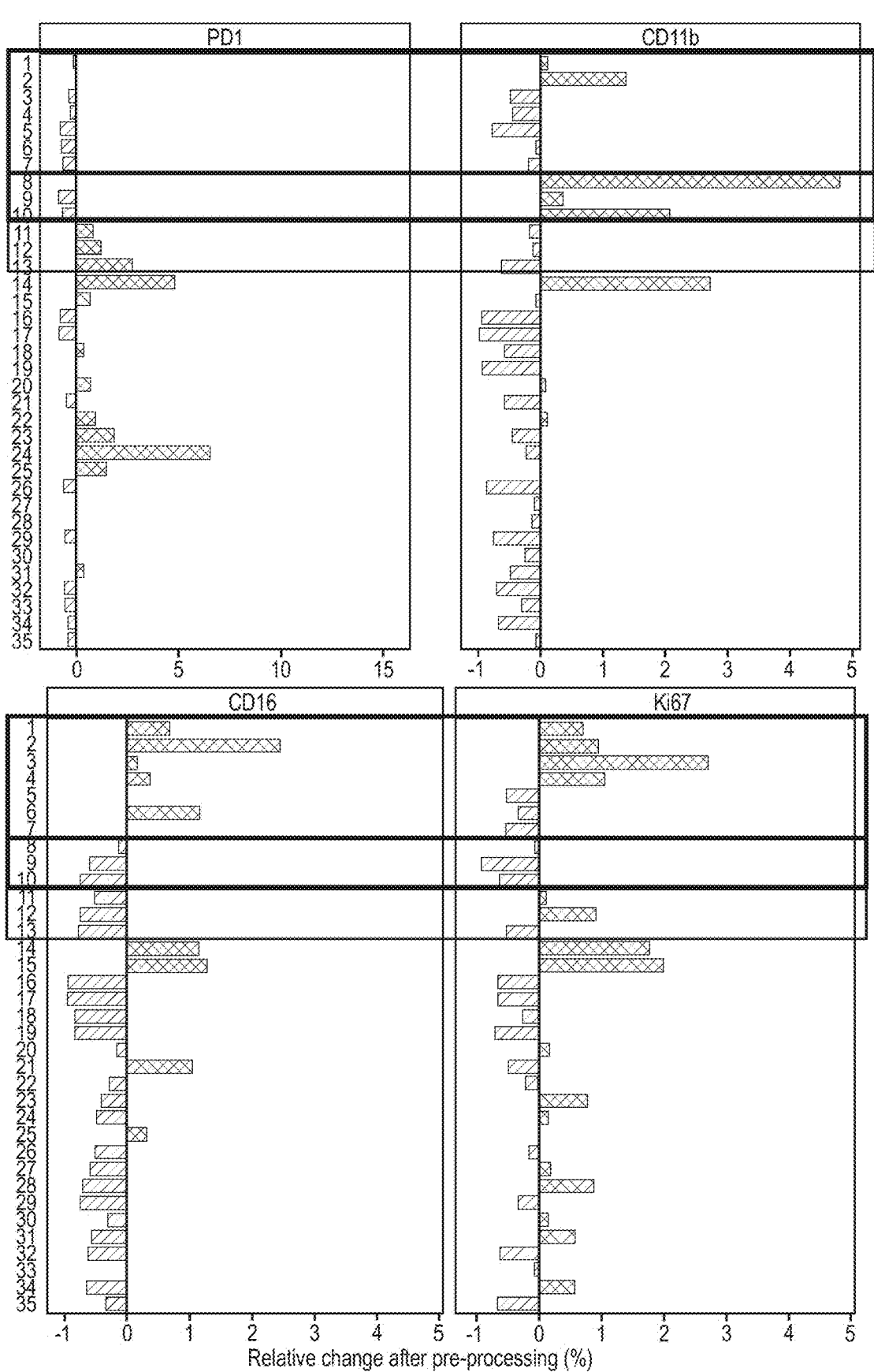

IMmuneCite allowed the discrimination of cells in different states of activation in the CD4+ and CD8+ T-cell and the B cell compartments which suggest a complex immune response and cell-to-cell interaction within the alloimmune microenvironment during active TCMR episodes (FIGS. 7, 8, 9, and 10). Additionally, we were able to reveal differences in macrophage polarization and their polymorphic activation states (FIGS. 9 and 10). Lastly, IMmuneCite allowed the detection of new molecular pathways important in mediating not only the alloimmune response, but also potentially new targets for immunotherapy to treat allograft rejection.

Example 4: External Validation of IMmuneCite Workflow

To assess its performance and versatility, the IMmuneCite workflow was applied to an external and publicly available IMC database containing 12 multiplexed images of liver tissues obtained from syngeneic mouse HCC models. The FFPE slides were stained with a 35-antibody panel. A raw dataset containing 125,222 cells along with a curated IMClean-processed dataset containing 125,790 cells was generated. Again, cell segmentation was performed using Mesmer. The IMmuneCite clustering algorithm was adopted to include the greater number of markers used in this study to possibly maximize cell phenotyping. Metaclusters were identified using the mouse IMmuneCite clustering algorithm tree shown in FIG. 11, which led to the identification of 10 metaclusters including 7 immune and 3 non-immune metaclusters (FIG. 12A). The thresholds for the lineage markers were optimized for each dataset separately to guarantee the most reliable cell phenotyping in each condition. Labelling accuracy was verified by visually inspecting the signal of multiple markers in raw and pre-processed images and the corresponding clusters on images masks. The differences in the expression profiles of these metaclusters are shown in the heatmaps (FIG. 12A), while difference in density and distribution between the two datasets are visualized in t-SNE plots (FIG. 12B). After applying IMClean pre-processing to the mouse data, a decrease was observed in the following metaclusters: CD8+ T-cells, B cells, polymorphonuclear cells (PMN) and endothelial cells. Conversely, macrophages, myofibroblasts, dendritic cell, epithelial cells, and other non-immune cells increased (FIG. 12C).

Figure 12E:
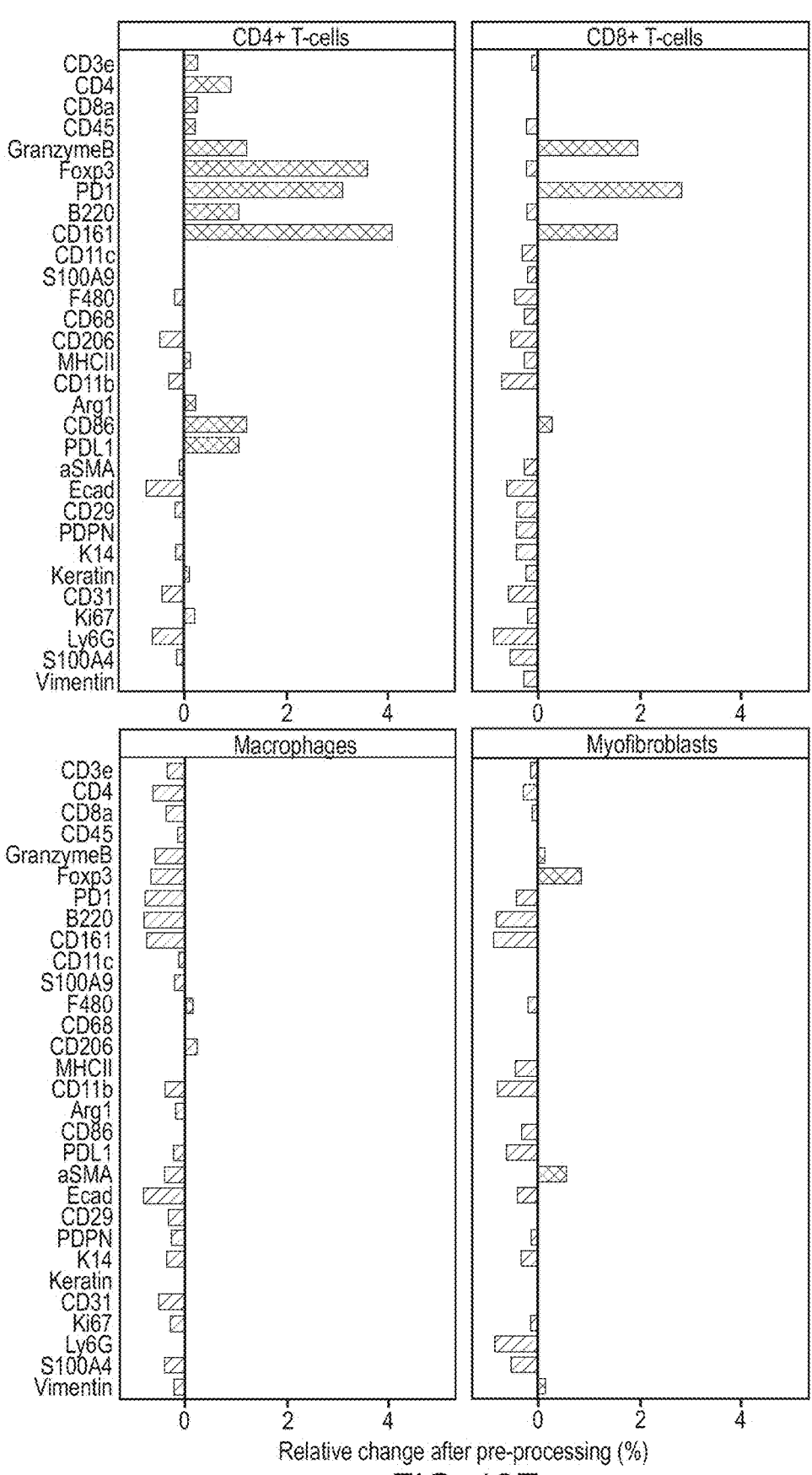
Figure 12E:
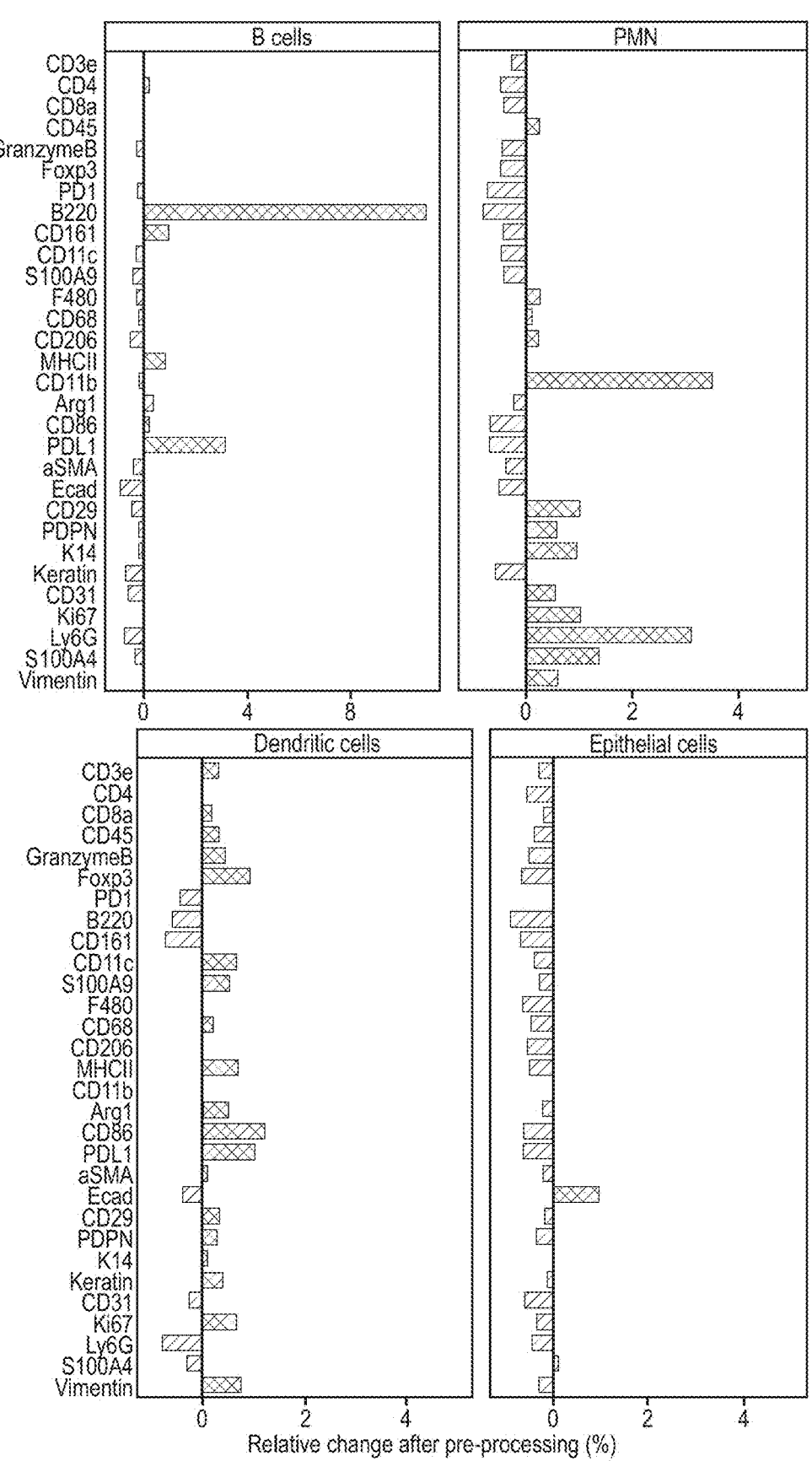
Figure 13D:
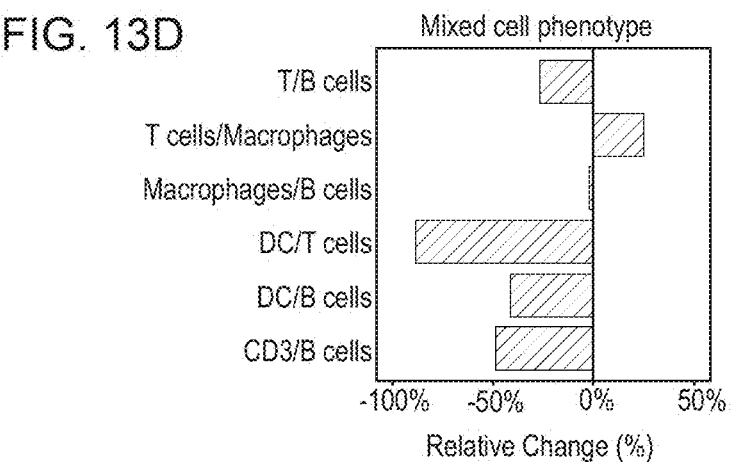
Figure 13E:
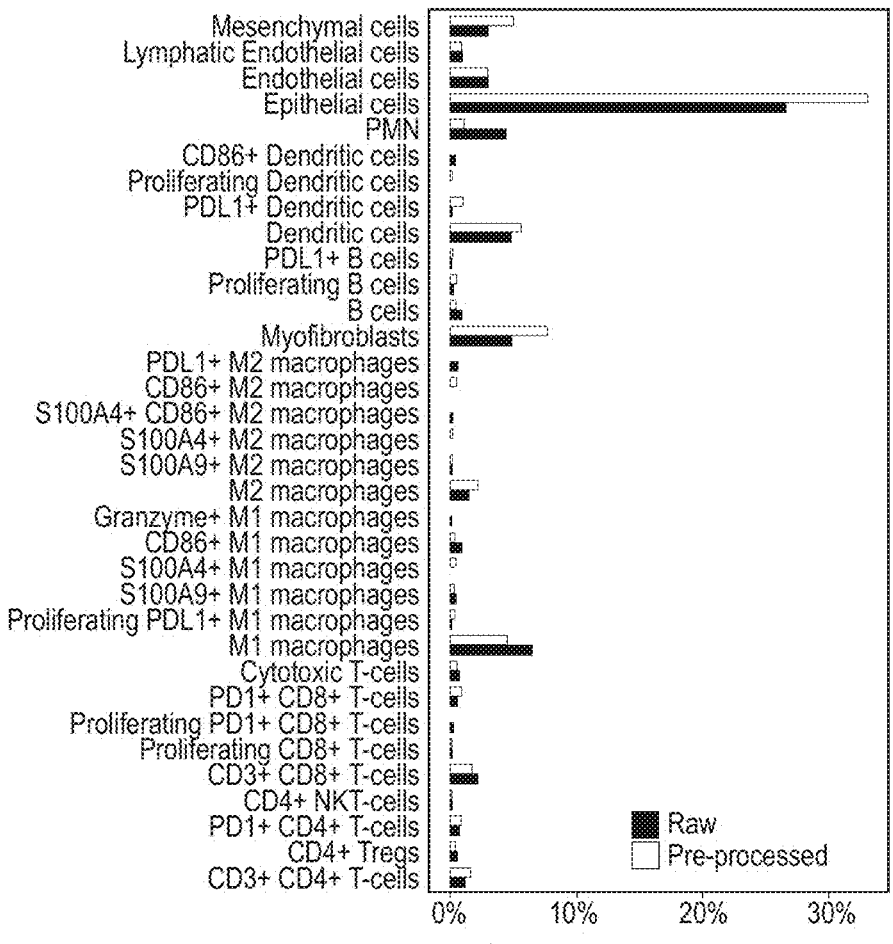

When the frequency of cells expressing markers biologically appropriate for the cell lineage in IMClean-processed data was analyzed, the cells in the CD4+ T-cell metacluster positively expressed both CD4 and CD3 and cells in the macrophage metacluster positively expressed CD68, F480, and CD206, while the proportion of cells expressing other non-specific markers in these metaclusters was minimal or null (FIG. 12D, circle size). Similarly, cells in the myofibroblast and dendritic cell metaclusters positively expressed αSMA and CD11c, respectively. Additionally, when the expression of these cells in raw vs. IMClean-processed datasets were compared, within each metacluster, expression of non-specific markers is reduced, while the expression of specific markers is enriched, especially in dendritic cells and other non-immune cells (FIG. 12D, color scale). Moreover, the expression of both lineage and functional markers were enriched in the specific cell phenotype, but decreased in other non-specific phenotypes, suggesting an increase in phenotype specificity (FIG. 12E). For example, post-IMClean, an increase in the ratio of PD1-expressing cells in T-cells and a decrease in all other metaclusters was observed. The ratio of cells expressing αSMA increased in myofibroblasts and epithelial cells, while decreasing in other metaclusters. The proportion of cells expressing B220 increased in B-cells, while decreasing in other metaclusters. The increased ratio of cells expressing B220 and cells expressing CD8a in the CD4+ T-cell compartment or the increased ratio of cells expressing CD8a and cells expressing CD3 in the dendritic cell metacluster could be due to cell segmentation and the close proximity among these APC and effector cells. Some discrepancies such as the increased presence of cells expressing epithelial markers in immune metaclusters might be due to their widespread staining and broader expression of those markers compared to immune specific markers, which cause overlap between them (FIG. 13A). Additionally, image artifacts related to the tissue were observed, which complicated the clustering step given that, in those areas, all markers had high expression patterns (FIG. 13A). However, a wrinkle in the tissue section was observed, leading to this artifact, and ultimately the cells from that specific area were excluded from further analysis given their non-biological expression pattern (FIGS. 13B and 13C). The frequency of cells with mixed phenotypes in mouse data with and without pre-processing was evaluated. Again, IMClean pre-processing reduced the frequency of non-biological mixed phenotypes in the case of co-expression of B and T cell markers (CD4 or CD8), co-expression of CD3 and B220, and co-expression of dendritic cells and T or B cell markers (FIG. 13D). A segmented mask showing the spatial location of the metaclusters obtained from the IMClean-processed dataset is shown in FIG. 12F and highlights the structural elements and the immune cell infiltration in a mouse HCC section.

Figures 15A, 15B, 15C, 15D:
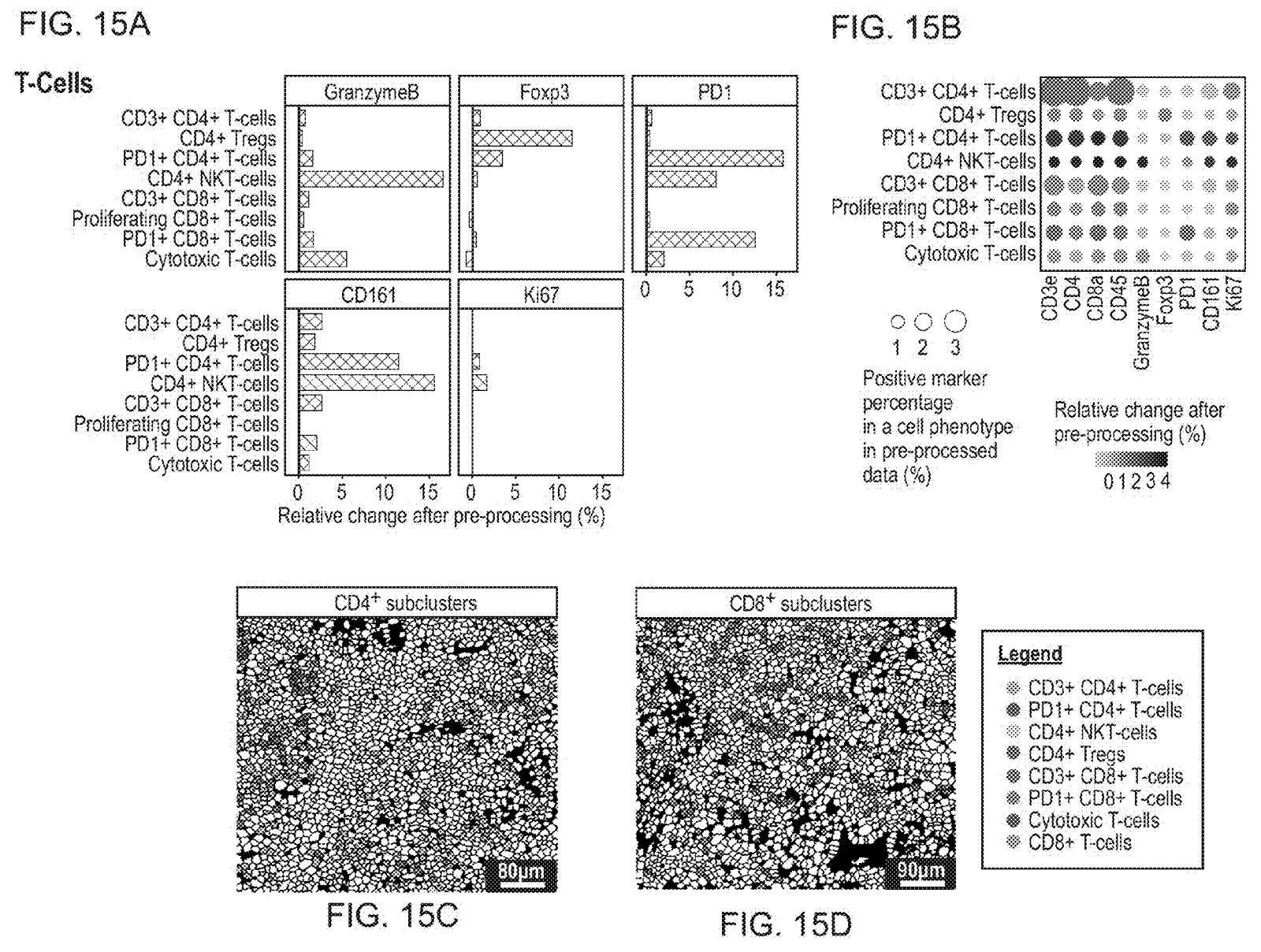
Figure 15E:
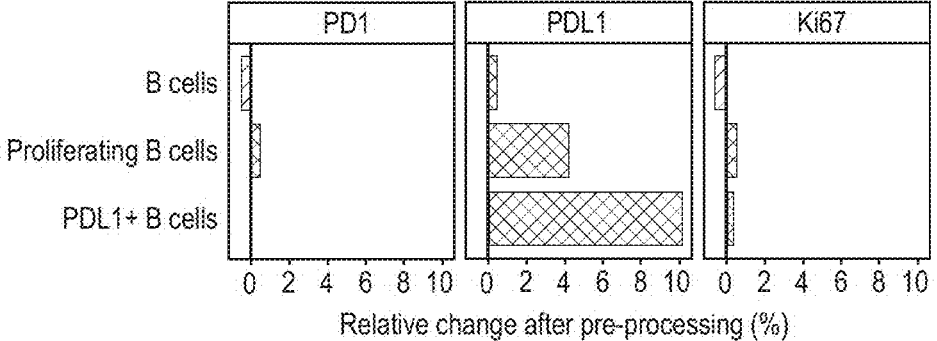
Figure 15F:
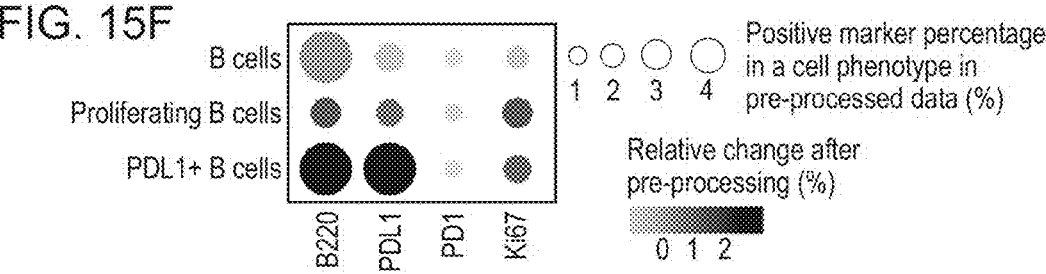
Figure 15G:
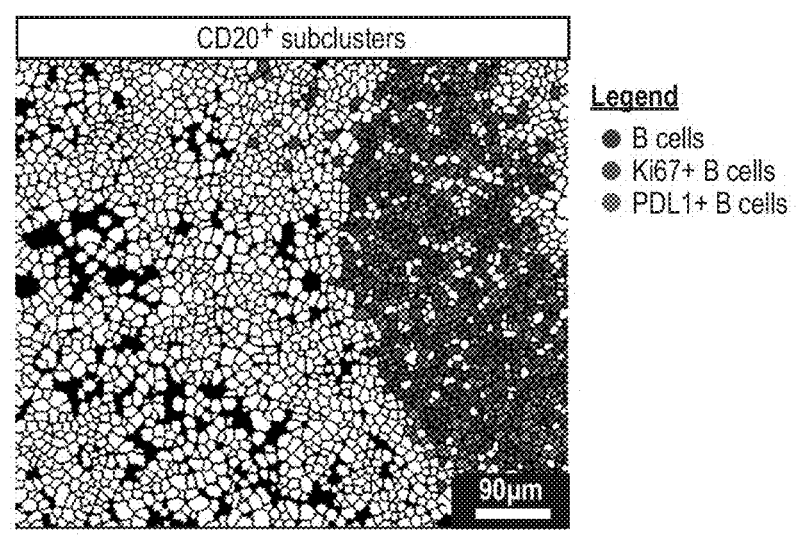

Following the same approach used for the human liver datasets, subcluster phenotyping was performed in both raw and pre-processed mouse datasets, obtaining 25 immune subclusters from raw data vs. 24 from pre-processed data (FIG. 13E-FIGS. 14A and 14B). After IMClean pre-processing, the expression of functional markers biologically specific to CD4+ and CD8+ T-cell subclusters was enriched in these subclusters, suggesting an increase in phenotype specificity (FIG. 15A). For example, the proportion of Foxp3-expressing cells was enriched in the CD4+ Tregs subcluster and reduced in the other non-CD4+ T-cell subclusters. The ratio of PD1-expressing cells was greater in both CD4+ and CD8+ T-cells identified as PD1+ CD4+ T-cells and PD1+ CD8+ T-cells, respectively, and the proportion of GranzymeB-expressing cells was increased in Cytotoxic T-cells and CD4+ natural killer T-cells (NKT-cells). Additionally, after IMClean pre-processing, we noticed an enrichment of specific markers for each subcluster, while the expression of markers not specific for the subclusters decreased (FIG. 15B). Tissue sections representing CD4+ and CD8+ T-cell subclusters are shown in FIG. 15C and FIG. 15D. While the same three B-cell subclusters were identified in both datasets, the expression of functional markers was enriched in these biologically specific subclusters (FIG. 15E). The frequency of cells expressing subcluster specific markers increased in the cell type resulting in increased relative change, while the non-specific markers decreased (FIG. 15F). The tissue localization of these subclusters is shown in FIG. 15G.

Figure 16A:
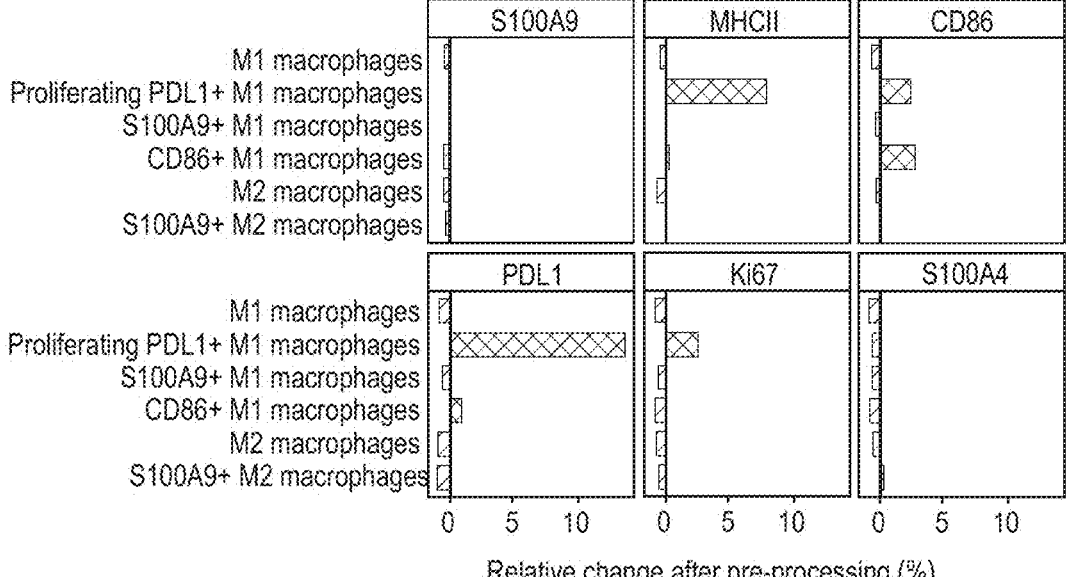
FIGS. 16A-16F show that the IMmuneCite workflow enables an accurate phenotyping of macrophages and dendritic cells in different mouse HCC tissue models.
Figure 16B:
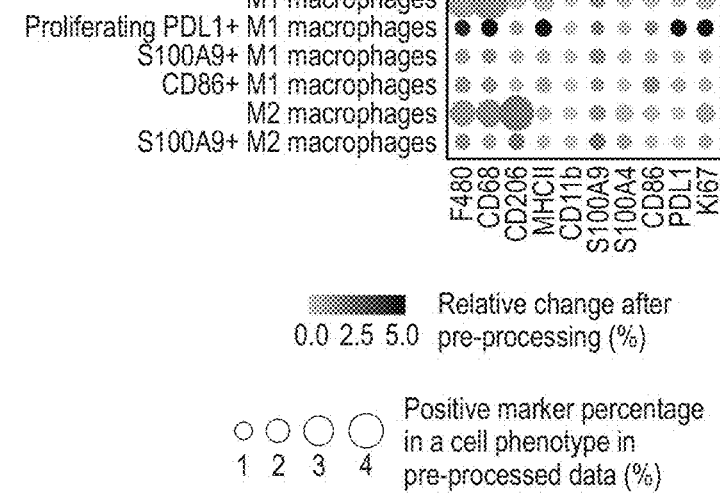

For macrophage subclusters, the ratio of cells expressing MHCII (Major Histocompatibility Complex class II), CD86, PDL1, and Ki67 was increased in the biologically specific macrophage subclusters (FIG. 16A). Accordingly, subcluster specific markers were increased while non-specific markers decreased after IMClean pre-processing (FIG. 16B).

Figures 16C, 16D, 16E, 16F:
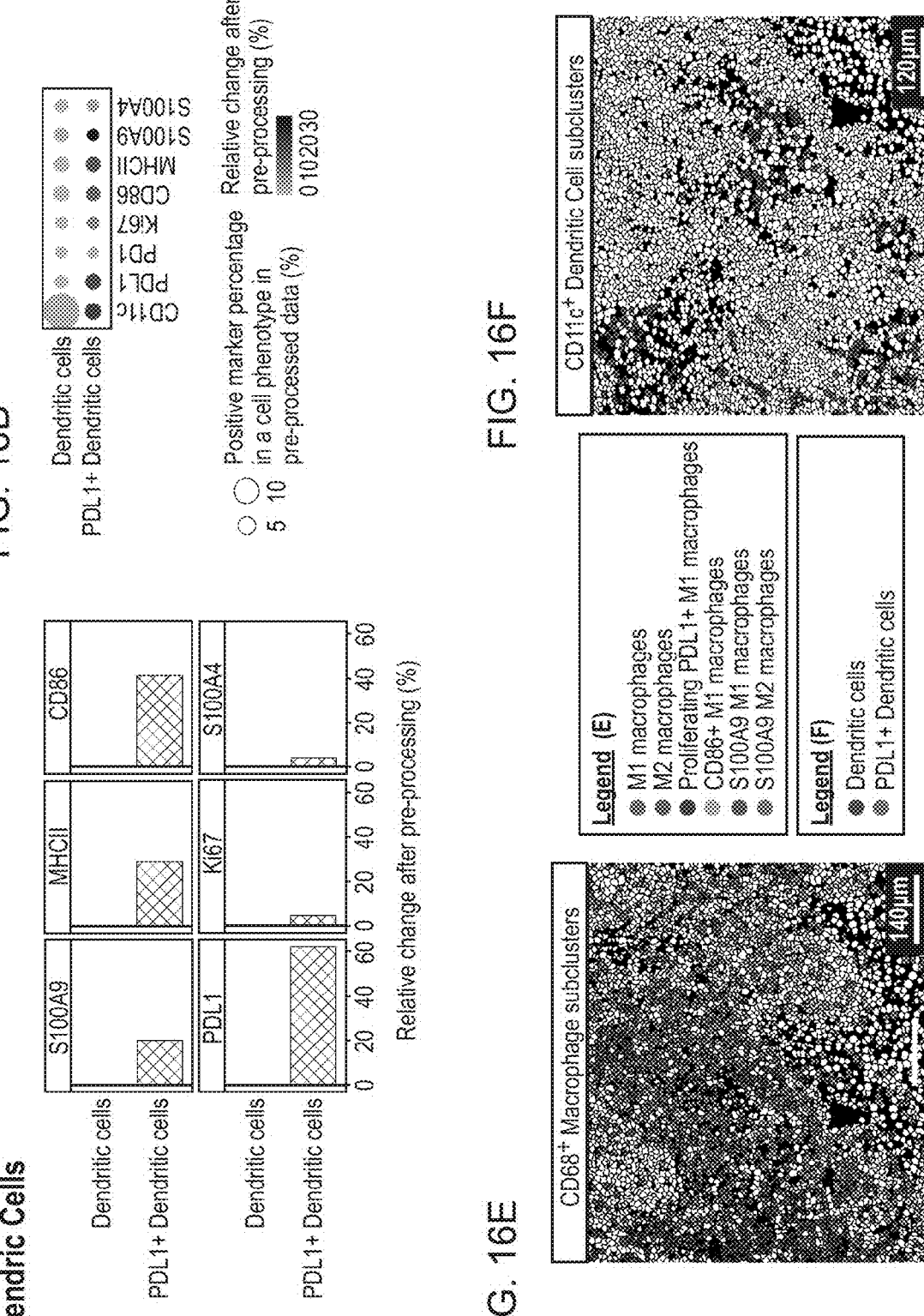

For dendritic cell subclusters, the ratio of cells expressing functional markers such as S100A9, MHCII, CD86, PDL1, S1004A, and Ki67 was increased in the specific PDL1+ dendritic cell subcluster, but not in the more generic 'dendritic cell' subcluster (FIG. 16C). Additionally, the 'dendritic cell' subcluster showed a high percentage of cells expressing CD11c after IMClean pre-processing (FIG. 16D, circle size) and we observed a positive change in the expression of subcluster specific markers when comparing raw vs. pre-processed data (FIG. 16D, color scale). Visualization specific macrophages and dendritic cells subclusters are shown in FIGS. 16E and 16F. This analysis confirms that IMmuneCite can identify different cell types as well as distinguish activation states of different cell types in tumor microenvironments, which usually exhibit a wide diversity. Thus, the identification of rare cell types associated with a certain stage of disease can lead to the identification of biomarkers of response to treatment or predictors of clinical outcomes.

Discussion

IMmuneCite is an open source and customizable framework developed for thorough immune focused analysis of spatial proteomic datasets. It enables pre-processing of raw images by using IMClean, which improves the quality of images used to generate a single-cell proteomic dataset by correcting for image artifacts caused by channel spillover, noise, and antibody aggregates (FIG. 3). Spatial proteomics data are commonly analyzed using unsupervised algorithms, which are affected by the presence of these artifacts. Thus, the production of optimized, high-quality images is imperative to generate a biologically relevant single-cell dataset to conduct downstream analysis and thus enable meaningful analyses of inflammatory pathologies. To address these challenges and limitations, techniques disclosed herein describe an image pre-processing method (i.e., IMClean) that enhances the specificity and sensitivity of immune markers in both metaclusters and subclusters in both murine and human tissue samples. The image pre-processing method removes clusters reflecting tissue artifacts and non-biological cellular phenotypes, confirming that the IMmuneCite workflow improves data accuracy. IMmuneCite offers a versatile, user-friendly, and reliable computational tool for spatial proteomics data that is adaptable to any antibody panel and capable of capturing multiple complex immune and non-immune cellular phenotypes associated with different diseases, as disclosed above. Additionally, the level of phenotype discrimination offered by IMmuneCite allows for the identification of cell populations which are key features of a certain disease or disease state. This was demonstrated by the few discrete PD1+ T-cells which predict TCMR in clinical LT and bolstered the concept that the PD1 pathway plays a major role in alloimmunity. The identification of this cell population suggests that using immunotherapies to increase exhaustion i.e. by using a PD1 agonist, may offer a new strategy to treat TCMR. Although the application is specifically discussed with respect to cancer it should be understood that the techniques described herein could be applied in other instances such as the study of acute liver failure and tumor immune microenvironments to enable the identification of cell types associated with therapy response, disease progression and, more generally, patient outcomes without departing from the spirit and scope of the present application. As many of the multiplexed technologies function well on FFPE clinical biopsy samples, incorporating spatial proteomics into clinical trials offers the opportunity to inform choice of therapeutic targets and treatment response as novel drug targets are investigated.

As disclosed above, IMmuneCite provided an in-depth representation of the intricacy of the alloimmune and tumor microenvironment in both liver allograft rejection and cancer. It was shown that IMClean, a Python-based image pre-processing tool, ameliorates the quality of multiplexed images by correcting for technical artifacts present in IMC images. Depending on antigen-antibody interactions, spatial proteomics has similar considerations to IHC in order to avoid image artifacts, which include antibody concentration optimization, clonality (monoclonal versus polyclonal), epitope affinity, as well as tissue preservation technique, length and type of fixation, dehydration of the tissue after fixation, and ischemia period (time between tissue collection and fixation). Although IMC is not affected by autofluorescence and background signal, which are typical of fluorophore-based technologies, a certain amount of signal spillover or channel crosstalk is still present and can affect experimental results and lead to false conclusions. Channel crosstalk is mainly due to metal isotopic impurity or oxide formation and is addressed by careful design of the antibody panel and selection of highly pure metal isotopes used for antibody conjugation. The first step of IMClean allows for channel crosstalk compensation post-acquisition by applying subtraction of the contaminating signal from any channel affected by signal spillover. Chevrier et al. developed CATA-LYST, an R package that creates a spillover matrix based on signals detected in adjacent channels from separated heavy-metal conjugated antibody placed on a glass agarose slide which is then used during the analysis to correct for spillover. While this might represent a faster and automated way to address the channel crosstalk issue, CATALYST has limitations. Specifically in that spillover compensation of high signal intensities requires the ablation of an antibody matrix every time the marker panel is modified, which comes with additional costs related to both total amount of antibodies required and ablation.

Compared to MAUI, which requires the use of a licensed platform and additional time-consuming steps to convert med into tiff files, IMClean combines all pre-processing steps in one single Python script, which streamlines the user workload and need for expertise in working with multiple platforms. Furthermore, compared to IMC-Denoise and SPEX, which focus on noise and aggregate removal and channel crosstalk and denoising respectively, IMClean accounts for all sources of image artifacts. This gives the user freedom to decide what correction step to apply. Additionally, while the application of the DIMR algorithm avoids a user-defined intensity threshold or range to identify hot pixels, it cannot remove hot pixels that appear in large clusters. While DeepSNiF remains less accurate compared to supervised denoising methods and requires high bioinformatic expertise, IMClean has been shown to be effective at removing any type of image artifacts with minimal bioinformatics knowledge expertise. By allowing the user to work through each step with minimal code interaction, the focus remains on pre-processing accuracy. IMClean enhances downstream analysis for cell identification and increases the specificity of each marker for the biologically appropriate cell type in data obtained from two different species (FIGS. 6A-6F and FIGS. 12A-12F). Additionally, image pre-processing effectively reduces the co-expression of markers from different cell lineages on the same cell, resulting in biologically misleading marker expression patterns and false annotation (FIG. 6F, FIG. 10D, and FIGS. 13A-13E). Although the examples described above only applied IMClean to two IMC datasets, one of ordinary skill in the art can appreciate that IMClean can be applied to other spatial proteomics technologies that are affected by similar image artifacts (e.g., MIBI and PhenoCycler).

Figure 11:
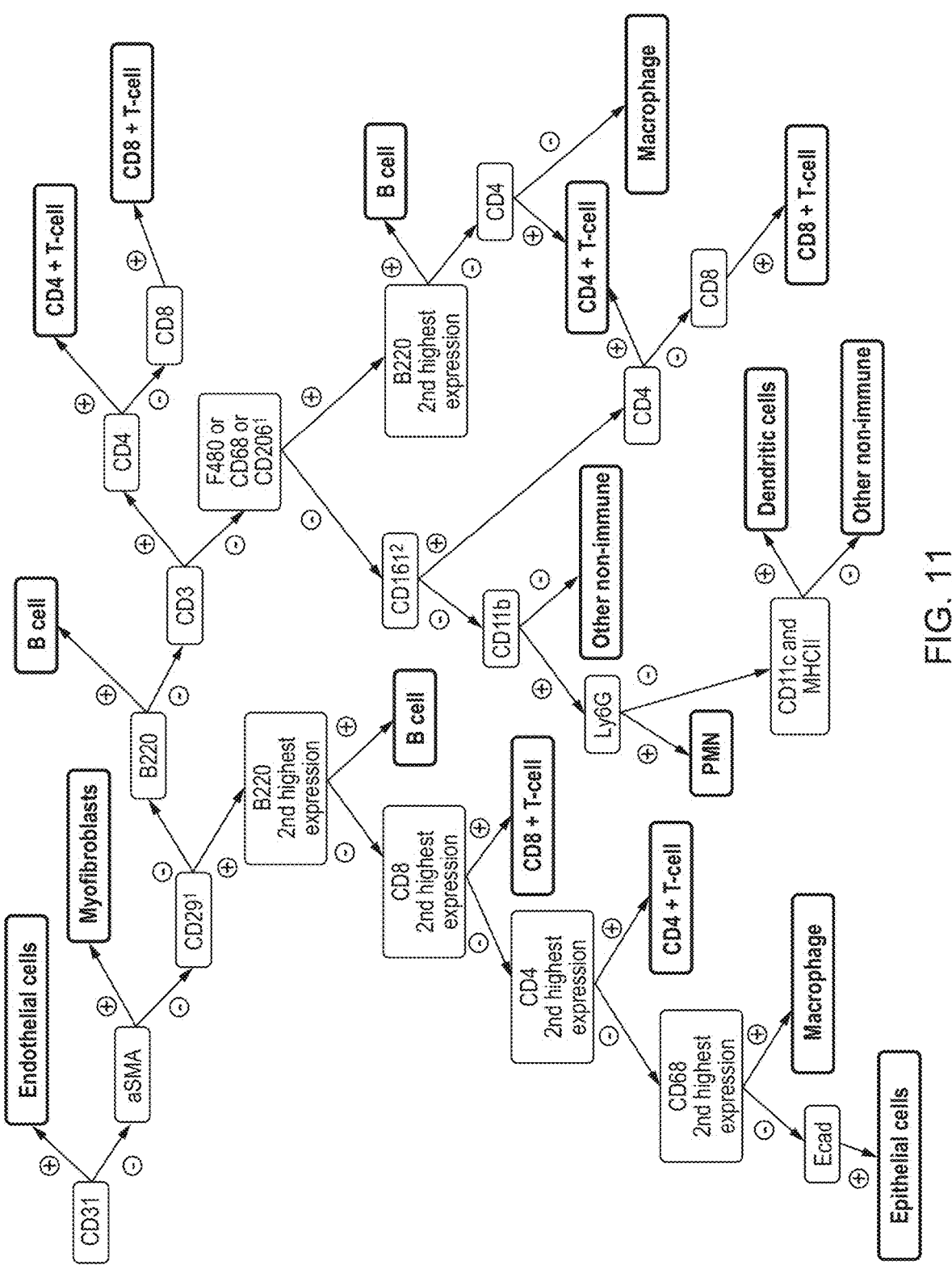
FIG. 11 shows the IMmuneCite clustering algorithm used to analyze imaging mass cytometry data obtained from HCC mouse models. The IMmuneCite clustering pipeline is robust across multiple disease' immune microenvironments and species. The IMmuneCite clustering algorithm was adapted to analyze IMC data obtained from four different HCC mouse models. After IMClean pre-processing and segmentation of images, marker expression measurements contained in the single-cell expression matrix are read into R and used for cell phenotype assignment using the IMmuneCite clustering algorithm adapted for mouse samples. Information on the top three highest expressed markers was extracted and used for cell categorization and phenotype assignment based on the algorithmic tree schematized above. The top five highest expressed markers were used for macrophages identification. To account for broad and unspecific expression of CD29 and spillover of signal from macrophages (due to their shape) into adjacent cell masks (cells co-expressing CD11c or CD68/CD4 and CD68/B220).

Cell phenotyping in proteomics data is usually performed using manual gating strategies combined with a priori knowledge of cell markers or unsupervised algorithms. These strategies are particularly cumbersome when antibody panels with several immune markers with overlapping distribution on multiple cell types are used. Low levels of non-biologic marker expression in clusters annotated based on unsupervised clustering can be visualized; however, it may not be evident to readers or reviewers who are not familiar with the technical details of cluster annotation and who solely rely on analysis of assigned cellular identities, which may not be optimized for accuracy. In this regard, the IMmuneCite clustering algorithm helps in the phenotyping process by performing cell identification in two steps. First, by using a supervised algorithm based on lineage marker expression, the overarching lineage or "compartment" of immune and non-immune cells is identified (FIG. 3 and FIG. 11). Secondly, each cell compartment can be further investigated and dissected to provide details on cell status and function. The second step relies on an unsupervised algorithm in combination with functional markers, thus allowing the user to further explore the cell microenvironment and obtain meticulous information about rare cell populations and the overall pathological immune landscape. Detection of rare cell populations, for example PD1+ cells, is particularly relevant to guide immune checkpoint treatment in patients with cancer or in the discovery of new biomarkers. As noted, the clustering approach can be easily modified to accommodate any antibody panel used to stain a wide variety of tissues in different pathological conditions, thus accounting for all the various cell populations identifiable.

A previously implemented clustering tool for IMC data was included in Cytomapper, an R/Bioconductor package that allows, among other features, cell labeling based on a hierarchical gating strategy on marker expression values. As such, it is subjective to inter-operator variability. More recently, ASTIR (ASsignmenT of sIngle-cell pRoteomics) has been developed imprimis for IMC data and relies on a scalable marker-based probabilistic model to assign cell phenotype to proteomics data. ASTIR uses both, measures of protein expression and a prespecified set of markers, to assign cell phenotype employing a machine learning model. However, ASTIR has a limited capability in identifying novel cell subsets as it relies on user inputs. Lastly, SIMPLI (Single-cell Identification from MultiPlexed Images) is a tool that allows users to classify cells by choosing between an unsupervised clustering algorithm and a user-defined thresholding method of markers of interest for cell phenotype assignment. Although SIMPLI represents a comprehensive tool for analysis of spatial proteomics data, it does not provide a framework to perform image pre-processing, thus requiring the investigator to have advanced bioinformatics support to work with raw data across various analysis platforms.

The image pre-processing pipeline and the clustering algorithm included in IMmuneCite have been implemented in two different platforms, Python and R, as standalone tools. While this might represent a limitation given that using the entire IMmuneCite framework requires the user to move from one platform to another, it also gives the freedom to perform either image correction or the clustering step and then move into downstream analysis. Another major strength is that both tools are available on free platforms and no license is required. A step-by-step manual that guides users through the IMClean pipeline is provided. Additionally, the cell identification algorithm for tailored phenotyping can be easily adapted to a specific tissue or immune cell type of interest, particularly when subclustering for unique phenotypic or functional properties. Finally, IMmuneCite can easily be modified to uncover characteristics associated with specific populations by refining the antibody panel used to interrogate these populations. This aspect can be generalized to any study and condition.

In conclusion, the IMmuneCite workflow simplifies an intense data workflow to enable an appropriate quantitative analysis of IMC data, particularly within immune rich disease states. It improves the useability of spatial proteomic data and facilitates cell phenotype identification while reducing incorrect cell phenotype assignment thus ensuring a proper analysis of complex and poorly characterized tissue immune microenvironment.

EMBODIMENTS

A1. A computer-implemented method comprising:
accessing an image file of a specimen stained with a panel of antibodies, wherein:
   the image file comprises regions of interest files of the specimen,
   the regions of interest files comprise individual signal files corresponding to each antibody in the panel of antibodies used to stain the specimen, and
   the individual signal files comprise artifact signals corresponding to background noise;
performing an image pre-processing method to remove the artifact signals from the individual signal files, wherein the image pre-processing method comprises:
   performing an iterative process comprising:
      (a) applying, to a first individual signal file of the individual signal files from a first region on interest file of the regions of interest files using a denoising filter, a first denoising threshold value to generate a first noise signal and a second denoising threshold value to generate a second noise signal, (b) removing, from the first individual signal file, the first noise signal and the second noise signal to generate a denoised image, (c) comparing the first individual signal file to the denoised image to determine the performance quality of the denoising filter, and (d) choosing, based on the comparing, to: (i) repeat steps (a)-(c) on the first individual file from the first region of interest file by modifying the first denoising threshold value and the second denoising threshold value, (ii) repeat steps (a)-(c) on the first individual signal file from a second or subsequent region of interest file of the regions of interest files, or (iii) ending the iterative process for the first individual signal file, and repeating the iterative process on a second or subsequent individual signal file of the individual signal files from the first region of interest to generate a set of denoised images for the specimen; and outputting the set of denoised images.

B1. A computer-implemented method comprising:

accessing an image file of a specimen stained with a panel of antibodies, wherein:

the image file comprises regions of interest files of the specimen, the regions of interest files comprise individual signal files corresponding to each antibody in the panel of antibodies used to stain the specimen, and the individual signal files comprise artifact signals corresponding to background noise;

performing an image pre-processing method to remove the artifact signals from the individual signal files, wherein the image pre-processing method comprises:

performing an iterative process comprising:

(a) applying, to a first individual signal file of the individual signal files from a first region on interest file of the regions of interest files using a denoising filter, a first denoising threshold value to generate a first noise signal and a second denoising threshold value to generate a second noise signal, (b) removing, from the first individual signal file, the first noise signal and the second noise signal to generate a denoised image, (c) comparing the first individual signal file to the denoised image to determine the performance quality of the denoising filter, and (d) choosing, based on the comparing, to: (i) repeat steps (a)-(c) on the first individual file from the first region of interest file by modifying the first denoising threshold value and the second denoising threshold value, (ii) repeat steps (a)-(c) on the first individual signal file from a second or subsequent region of interest file of the regions of interest files, or (iii) ending the iterative process for the first individual signal file, and repeating the iterative process on a second or subsequent individual signal file of the individual signal files from the first region of interest to generate a set of denoised images for the specimen; and outputting the set of denoised images.

B2. The computer-implemented method of embodiment B2, wherein the image file is obtained from imaging mass cytometry.

B3. The computer-implemented method of embodiment B2, wherein the specimen is a biological sample obtained from a subject.

B4. The computer-implemented method of embodiment B3, wherein the biological sample is a cell-containing liquid or a tissue.

B5. The computer-implemented method of embodiment B4, wherein the biological sample is a tissue and the tissue is liver, heart, lungs, kidney, stomach, intestine, trachea, cornea, bone, tendon, skin, pancreas, heart valves, nerves, or vascular tissue.

B6. The computer-implemented method of embodiment B5, wherein the biological sample is a liver tissue sample.

B7. The computer-implemented method of embodiment B3, wherein the subject is healthy, has a disease, or is an organ transplant recipient.

B8. The computer-implemented method of embodiment B7, wherein the subject has a disease.

B9. The computer-implemented method of embodiment B8, wherein the disease is cancer.

B10. The computer-implemented method of embodiment B7, wherein the subject is an organ transplant recipient.

B10. The computer-implemented method of embodiment B7, wherein the subject is a liver transplant recipient.

B11. The computer-implemented method of embodiment B1, wherein the panel of antibodies recognize unique cell surface markers.

B12. The computer-implemented method of embodiment B11, wherein the panel of antibodies comprise two or more antibodies that recognize CD66b, CD20, CD28, CD16, CD163, CD11b, CD45, CD4, CD31, CD279, CD68, Foxp3, CK7, Ki-67, CD8a, Collagen Type I, CD3e, CD138, HLA-DR, Granzyme B, DNA1, DNA2, or any combination thereof.

B12. The computer-implemented method of embodiment B11, wherein the panel of antibodies are labeled with metal tags.

B13. The computer-implemented method of embodiment B12, wherein the metal tags comprise 139La, 142Nd, 144Nd, 146Nd, 147Sm, 149Sm, 152Sm, 153Eu, 154Sm, 156Gd, 159Tb, 160Gd, 164Dy, 167Er, 168Er, 169Tm, 170Er, 172Yb, 174Yb, 175Lu, 191Ir, 193Ir, or any combination thereof.

B14. The computer-implemented method of embodiment B1, wherein:

the minimum filter value depends upon the antibody panel and corresponding to a signal level below a designated minimum threshold, and the uniform filter value used to average pixel intensities, and (i) the minimum filter value is set to a desired integer and the uniform threshold value is set to null, (ii) the minimum filter value is set to a null value and the uniform threshold value is set to a desired integer value, (iii) the minimum filter value is set to a desired integer and the uniform threshold value is set to a desired integer value, or (iv) the minimum filter value is set to a null value and the uniform threshold value is set to a null value.

B15. The computer-implemented method of embodiment B1, wherein repeating steps (a)-(c) on the first individual file from the second or subsequent regions of interest files comprises:

(i) applying the minimum threshold value and the uniform threshold value to all the first individual files in the second or subsequent regions of interest files, (ii) applying new minimum threshold values and uniform threshold values to each of the first individual signal files in the second or subsequent regions of interest files, or (iii) a combination of (i) and (ii).

B16. The computer-implemented method of embodiment B1, further comprises performing downstream analysis on the set of stacked images, wherein the downstream analysis comprises:

generating, by a cell segmentation tool using the set of stacked images, single-cell masks and a marker-expression matrix;

generating, by a cell-phenotype identification pipeline using the single-cell masks and the marker-expression matrix, subclusters of cells based on their expression of lineage markers;

generating, by an extraction algorithm using the expression of lineage markers associated with each subcluster of cells, a labeled dataset comprising a list the subclusters of cells and their corresponding expression patterns of the lineage markers;

determining, by inputting the labeled dataset into a machine learning model, a clinical outcome based on the subclusters of cells.

C1. A computer-implemented method for processing imaging data comprising:

accessing an image file of a specimen stained with a panel of antibodies, wherein:

the image file comprises regions of interest files of the specimen, the regions of interest files comprise individual signal files corresponding to each antibody in the panel of antibodies used to stain the specimen, and the individual signal files comprise artifact signals corresponding to background noise;

performing an image pre-processing method to remove the artifact signals from the individual signal files, wherein the image pre-processing method comprises:

performing an iterative process comprising:

(a) processing the first individual signal file using a first artifact filter, wherein the output of the first artifact filter corresponds to a spillover corrected image, (b) processing the spillover corrected image using a second artifact filter, wherein the output of the second artifact filter corresponds to a denoised image, (c) processing the denoised image using a third artifact filter, wherein the output of the third artifact filter corresponds to an aggregate removal image, and (d) repeating steps (a)-(c) for the first individual signal file from a second or subsequent region of interest file;

repeating the iterative process on a second or subsequent individual signal file from the first region of interest file of the image file to generate a set of stacked images comprising the aggregate removal images from each of the regions of interest files;

generating, by a cell segmentation tool using the set of stacked images, single-cell masks and a marker-expression matrix;

generating, by a cell-phenotype identification pipeline using the single-cell masks and the marker-expression matrix, subclusters of cells based on their expression of lineage markers;

generating, by an extraction algorithm using the expression of lineage markers associated with each subcluster of cells, a labeled dataset comprising a list the subclusters of cells and their corresponding expression patterns of the lineage markers; and determining, by inputting the labeled dataset into a machine learning model, a clinical outcome based on the subclusters of cells.

C2. The computer-implemented method of embodiment C1, wherein the image file is obtained from imaging mass cytometry.

C3. The computer-implemented method of embodiment C1, wherein the specimen is a biological sample obtained from a subject.

C4. The computer-implemented method of embodiment C3, wherein the biological sample is a cell-containing liquid or a tissue.

C5. The computer-implemented method of embodiment C4, wherein the biological sample is a tissue and the tissue is liver, heart, lungs, kidney, stomach, intestine, trachea, cornea, bone, tendon, skin, pancreas, heart valves, nerves, or vascular tissue.

C6. The computer-implemented method of embodiment C5, wherein the biological sample is a liver tissue sample.

C7. The computer-implemented method of embodiment C3, wherein the subject is healthy, has a disease, or is an organ transplant recipient.

C8. The computer-implemented method of embodiment C7, wherein the subject has a disease.

C9. The computer-implemented method of embodiment C8, wherein the disease is cancer.

C10. The computer-implemented method of embodiment C7, wherein the subject is an organ transplant recipient.

C11. The computer-implemented method of embodiment C10, wherein the subject is a liver transplant recipient.

C12. The computer-implemented method of embodiment C1, wherein the panel of antibodies recognize unique cell surface markers.

C13. The computer-implemented method of embodiment C12, wherein the panel of antibodies comprise two or more antibodies that recognize CD66b, CD20, CD28, CD16, CD163, CD11b, CD45, CD4, CD31, CD279, CD68, Foxp3, CK7, Ki-67, CD8a, Collagen Type I, CD3e, CD138, HLA-DR, Granzyme B, DNA1, DNA2, or any combination thereof.

C14. The computer-implemented method of embodiment C13, wherein the panel of antibodies are labeled with metal tags.

C15. The computer-implemented method of embodiment C14, wherein the metal tags comprise 139La, 142Nd, 144Nd, 146Nd, 147Sm, 149Sm, 152Sm, 153Eu, 154Sm, 156Gd, 159Tb, 160Gd, 164Dy, 167Er, 168Er, 169Tm, 170Er, 172Yb, 174Yb, 175Lu, 191Ir, 193Ir, or any combination thereof.

C16. The computer-implemented method of embodiment C1, wherein the first artifact filter is a spillover correction filter that removes artifact signals by:

(a) extracting, from the first region of interest file, a source channel and a target channel, wherein the target channel is the first individual signal file from the first region of interest file, (b) inputting, into the spillover correction filter, the source channel, the target channel, a cap threshold value, a Gaussian radius value, a binarizing threshold value, and a removal value, (c) applying, to the source channel, the cap threshold value, wherein the cap threshold value is the maximum signal value for the source channel, (d) applying, to the source channel, a Gaussian radius filter, wherein the Gaussian radius filter smooths and blurs the source channel based on the Gaussian radius value, (e) applying, to the source channel, the binarizing threshold value to set any signal value above the binarizing threshold value to a predetermined value and any signal value below the binarizing threshold value to a null value to generate a binarized mask corresponding to the areas in the source channel that are either positive for signal spillover or negative for signal spillover, (f) applying, to the target channel, the removal value, wherein the removal value is subtracted from all the pixels in the target channel that correspond to the areas in the binarized mask with the predetermined value to generate a spillover corrected image, (g) comparing the target channel to the spillover corrected image, (h) choosing to either (i) repeat steps (a)-(g) on first individual signal file by updating the cap threshold value, the Gaussian radius value, the binarizing threshold value, the removal value, or any combination thereof, (ii) perform a second spillover correction by repeating steps (a)-(g) with a new source channel selected from the individual signal files from the first region of interest, or (iii) finalize the spillover correction step and output the spillover corrected image.

C17. The computer-implemented method of embodiment C16, wherein the source channel is the individual signal file contaminating the other individual signal files in the first region of interest file.

C18. The computer-implemented method of embodiment C1, wherein the second artifact filter is a denoising filter that removes artifact signals by:

(a) inputting, into the denoising filer, the spillover corrected image, a minimum threshold value, and a uniform threshold value, (b) applying, to the spillover corrected image, the minimum filter value and setting any signal below the minimum filter value to a predetermined value to generate a first noise signal, (c) applying, to the spillover corrected image, a uniform filter based on the uniform filter value, wherein the uniform filter distinguishes true signal pixels from false signal pixels and sets the false signal pixels to the predetermined value to generate a second noise signal, (d) removing, from the spillover corrected image, the first noise signal and the second noise signal to generate a denoised image, (e) comparing the spillover corrected image to the denoised image, and (f) choosing to either (i) repeat steps (a)-(e) on the spillover corrected image by updating the minimum threshold value and the uniform threshold value, (ii) repeat steps (a)-(e) with a second or subsequent spillover corrected image from the first region of interest file, or (iii) finalizing the denoising step and output a denoised image.

C19. The computer-implemented method of embodiment C18, wherein:

the minimum filter value dependent upon the antibody panel and corresponding to a signal level below a designated minimum threshold, and the uniform filter value used to average pixel intensities, and (i) the minimum filter value is set to a desired integer and the uniform threshold value is set to a null value, (ii) the minimum filter value is set to a null value and the uniform threshold value is set to a desired integer value, (iii) the minimum filter value is set to a desired integer and the uniform threshold value is set to a desired integer value, or (iv) the minimum filter value is set to a null value and the uniform threshold value is set to a null value.

C20. The computer-implemented method of embodiment C18, wherein repeating steps (a)-(e) with the second or subsequent individual files from the first region of interest file comprises:

(i) applying the minimum threshold value and the uniform threshold value to all the individual files in the region of interest, (ii) applying new minimum threshold values and uniform threshold values to each individual signal file in the region of interest, or (iii) a combination of (i) and (ii).

C21. The computer-implemented method of embodiment C1, wherein the third artifact filter is an aggregate removal filter that removes artifact signals by:

(a) inputting, into the aggregate removal filter, the denoised image, a Gaussian radius value, and a size threshold value, (b) applying, to the denoised image, a Gaussian radius filter, wherein the Gaussian radius filter smooths and blurs the denoised image based on the Gaussian radius value to distinguish cellular structures having larger size and radiuses from aggregates having smaller size and radiuses to generate a blurred image, (c) applying, to the blurred image, the size threshold value to set any structure above the size threshold value to a predetermined value and any structure below the size threshold value to a null value to generate a binarized mask corresponding to the areas in the source channel that are either true positive signal or aggregate signal, (d) removing, from the blurred image, the structures having smaller size and radiuses that correspond to the structures in the binarized mask given a null value to generate an aggregate removal image, (e) comparing the denoised image to the aggregate removal image;

(f) choosing to either (i) repeat steps (a)-(e) on the denoised image by updating the Gaussian radius value and the binarizing threshold value, or (ii) finalizing the aggregate removal step and output an aggregate removal image.

C22. The computer-implemented method of embodiment C1, wherein repeating steps (a)-(c) further comprises:

(i) applying the same values selected for the first artifact filter, the second artifact filter, and the third artifact filter used for the first individual signal file from the first region of interest file to each of the other first individual signal files in the other regions of interest files, (ii) selecting new values for the first artifact filter, the second artifact filter, and the third artifact filter to be applied to each of the other first individual signal files in the other regions of interest files, or (iii) a combination of (i) and (ii).

C23. The computer-implemented method of embodiment C1, wherein the cell-phenotype identification pipeline comprises a clustering algorithm and an unsupervised clustering algorithm.

C24. The computer-implemented method of embodiment C23, wherein the clustering algorithm, based on expression of lineage markers in the marker-expression matrix, generates clusters of general cell phenotypes.

C25. The computer-implemented method of embodiment C24, wherein the lineage markers comprise CD66b, CD20, CD28, CD16, CD163, CD11b, CD45, CD4, CD31, CD279, CD68, Foxp3, CK7, Ki-67, CD8a, Collagen Type I, CD3e, CD138, HLA-DR, Granzyme B, DNA1, DNA2, or any combination thereof.

C26. The computer-implemented method of embodiment C24, wherein the clusters of general cell phenotypes comprise CD4+ T-cells, CD8+ T-cells, B cells, macrophages, monocytes, plasma cells, neutrophils, endothelial cells, cholangiocytes, hepatocytes, or any combination thereof.

C27. The computer-implemented method of embodiment C23, wherein the unsupervised subclustering algorithm recognizes the expression of lineage markers associated with the cluster of general cell phenotypes, to generate subclusters of cells.

C28. The computer-implemented method of embodiment C27, wherein the subclusters of cells comprise cholangiocytes, endothelial cells, hepatocytes, B cells, proliferating B cells, PD1+ B cells, CD3+ CD4+ T cells, resident memory CD4+ T cells, naïve CD4+ T cells, HLADR+ CD4+ T regulatory cells, HLADR-CD4+ T regulatory cells, PD1+ CD4+ T cells, proliferating CD4+ T cells, activated CD4+ T cells, CD16+CD4+ T cells, CD3+ CD8+ T cells, cytotoxic T cells, proliferating CD8+ T cells, PD1+ CD8+ T cells, PD1+ CD28+ CD8+ T cells, M1 macrophages, proliferating M1 macrophages, CD11b+ M1 macrophages, CD16+ M1 macrophages, M2 macrophages, CD11b+ M2 macrophages, CD16+ M2 macrophages, HLADR+ M2 macrophages, classical monocytes, non-classical monocytes, intermediate monocytes, activated monocytes, neutrophils, plasma cells, or any combination thereof.

C29. The computer-implemented method of embodiment C27, further comprising extracting the expression of lineage markers, using an extraction algorithm, associated with each subcluster of cells and generating a labeled dataset, wherein the labeled dataset comprises a list the subclusters of cells and their corresponding expression patterns of the lineage markers.

C30. The computer-implemented method of embodiment C29, wherein the labeled dataset is input in a machine learning model that predicts a clinical outcome based on the subclusters of cells and their corresponding expression patterns of the lineage markers.

C31. The computer-implemented method of embodiment C30, wherein the clinical outcome is organ rejection.

ADDITIONAL CONSIDERATIONS

Implementation of the techniques, blocks, steps, and means described above can be done in various ways. For example, these techniques, blocks, steps, and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine-readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium", "storage" or "memory" can represent one or more memories for storing data, including read only memory (ROM), random access memory (RAM), magnetic RAM, core memory, magnetic disk storage mediums, optical storage mediums, flash memory devices and/or other machine-readable mediums for storing information. The term "machine-readable medium" includes but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure. The ensuing description provides preferred exemplary embodiments only, and is not intended to limit the scope, applicability, or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

What is claimed:

1. A computer-implemented method comprising:

accessing an image file of a specimen stained with a panel of antibodies, wherein: the image file comprises regions of interest files of the specimen, the regions of interest files comprise individual signal files corresponding to each antibody in the panel of antibodies used to stain the specimen, and the individual signal files comprise artifact signals corresponding to background noise;

performing an image pre-processing method to remove the artifact signals from the individual signal files, wherein the image pre-processing method comprises:

performing an iterative process comprising:

(a) applying, to a first individual signal file of the individual signal files from a first region on interest file of the regions of interest files using a denoising filter, a first denoising threshold value to generate a first noise signal and a second denoising threshold value to generate a second noise signal, (b) removing, from the first individual signal file, the first noise signal and the second noise signal to generate a denoised image, (c) comparing the first individual signal file to the denoised image to determine the performance quality of the denoising filter, and (d) choosing, based on the comparing, to: (i) repeat steps (a)-(c) on the first individual file from the first region of interest file by modifying the first denoising threshold value and the second denoising threshold value, (ii) repeat steps (a)-(c) on the first individual signal file from a second or subsequent region of interest file of the regions of interest files, or (iii) ending the iterative process for the first individual signal file, and repeating the iterative process on a second or subsequent individual signal file of the individual signal files from the first region of interest to generate a set of denoised images for the specimen; and outputting the set of denoised images.

2. The computer-implemented method of claim 1, wherein the image file is obtained from imaging mass cytometry.

3. The computer-implemented method of claim 1, wherein:

(i) the panel of antibodies comprise two or more antibodies that recognize CD66b, CD20, CD28, CD16, CD163, CD11b, CD45, CD4, CD31, CD279, CD68, Foxp3, CK7, Ki-67, CD8a, Collagen Type I, CD3e, CD138, HLA-DR, Granzyme B, DNA1, DNA2, or any combination thereof, and (ii) the panel of antibodies are labeled with metal tags and wherein the metal tags comprise 139La, 142Nd, 144Nd, 146Nd, 147Sm, 149Sm, 152Sm, 153Eu, 154Sm, 156Gd, 159Tb, 160Gd, 164Dy, 167Er, 168Er, 169Tm, 170Er, 172Yb, 174Yb, 175Lu, 191Ir, 193Ir, or any combination thereof.

4. The computer-implemented method of claim 1, wherein:

the first denoising threshold value is a minimum filter value dependent upon the antibody panel and corresponding to a signal level below a designated minimum threshold, and the second denoising threshold value is a uniform filter value used to average pixel intensities, and (i) the minimum filter value is set to a desired integer and the uniform threshold value is set to null, (ii) the minimum filter value is set to a null value and the uniform threshold value is set to a desired integer value, (iii) the minimum filter value is set to a desired integer and the uniform threshold value is set to a desired integer value, or (iv) the minimum filter value is set to a null value and the uniform threshold value is set to a null value.

5. The computer-implemented method of claim 1, wherein repeating steps (a)-(c) on the first individual file from the second or subsequent regions of interest files comprises:

(i) applying the first denoising threshold value and the second denoising threshold value to all the first individual files in the second or subsequent regions of interest files, (ii) applying new minimum threshold values and uniform threshold values to each of the first individual signal files in the second or subsequent regions of interest files, or (iii) a combination of (i) and (ii).

6. The computer-implemented method of claim 1, wherein the image pre-processing further comprises:

performing another iterative process starting with a first denoised image from the set of denoised images, wherein the other iterative process comprises:

(e) processing the first denoised image using a spillover correction filter to generate a spillover corrected image, (f) processing the spillover corrected image using an aggregate removal filter to generate an aggregate removal image, and (g) repeating steps (e) and (f) for a second or subsequent denoised image from the set of denoised images to generate a set of stacked images comprising the aggregate removal images.

7. The computer-implemented method of claim 6, further comprises performing downstream analysis on the set of stacked images, wherein the downstream analysis comprises:

generating, by a cell segmentation tool using the set of stacked images, single-cell masks and a marker-expression matrix;

generating, by a cell-phenotype identification pipeline using the single-cell masks and the marker-expression matrix, subclusters of cells based on their expression of lineage markers;

generating, by an extraction algorithm using the expression of lineage markers associated with each subcluster of cells, a labeled dataset comprising a list the subclusters of cells and their corresponding expression patterns of the lineage markers;

determining, by inputting the labeled dataset into a machine learning model, a clinical outcome based on the subclusters of cells.

8. A system comprising:

one or more processors; and one or more computer-readable media storing instructions which, when executed by the one or more processors, cause the system to perform operations comprising:

accessing an image file of a specimen stained with a panel of antibodies, wherein:

the image file comprises regions of interest files of the specimen, the regions of interest files comprise individual signal files corresponding to each antibody in the panel of antibodies used to stain the specimen, and the individual signal files comprise artifact signals corresponding to background noise;

performing an image pre-processing method to remove the artifact signals from the individual signal files, wherein the image pre-processing method comprises:

performing an iterative process comprising:

(a) applying, to a first individual signal file of the individual signal files from a first region on interest file of the regions of interest files using a denoising filter, a first denoising threshold value to generate a first noise signal and a second denoising threshold value to generate a second noise signal, (b) removing, from the first individual signal file, the first noise signal and the second noise signal to generate a denoised image, (c) comparing the first individual signal file to the denoised image to determine the performance quality of the denoising filter, and (d) choosing, based on the comparing, to: (i) repeat steps (a)-(c) on the first individual file from the first region of interest file by modifying the first denoising threshold value and the second denoising threshold value, (ii) repeat steps (a)-(c) on the first individual signal file from a second or subsequent region of interest file of the regions of interest files, or (iii) ending the iterative process for the first individual signal file, and repeating the iterative process on a second or subsequent individual signal file of the individual signal files from the first region of interest to generate a set of denoised images for the specimen; and outputting the set of denoised images.

9. The computer-implemented method of claim 8, wherein the image file is obtained from imaging mass cytometry.

10. The system of claim 8, wherein:

(i) the panel of antibodies comprise two or more antibodies that recognize CD66b, CD20, CD28, CD16, CD163, CD11b, CD45, CD4, CD31, CD279, CD68, Foxp3, CK7, Ki-67, CD8a, Collagen Type I, CD3e, CD138, HLA-DR, Granzyme B, DNA1, DNA2, or any combination thereof, and (ii) the panel of antibodies are labeled with metal tags and wherein the metal tags comprise 139La, 142Nd, 144Nd, 146Nd, 147Sm, 149Sm, 152Sm, 153Eu, 154Sm, 156Gd, 159Tb, 160Gd, 164Dy, 167Er, 168Er, 169Tm, 170Er, 172Yb, 174Yb, 175Lu, 191Ir, 193Ir, or any combination thereof.

11. The system of claim 8, wherein:

the first denoising threshold value is a minimum filter value dependent upon the antibody panel and corresponding to a signal level below a designated minimum threshold, and the second denoising threshold value is a uniform filter value used to average pixel intensities, and (i) the minimum filter value is set to a desired integer and the uniform threshold value is set to null, (ii) the minimum filter value is set to a null value and the uniform threshold value is set to a desired integer value, (iii) the minimum filter value is set to a desired integer and the uniform threshold value is set to a desired integer value, or (iv) the minimum filter value is set to a null value and the uniform threshold value is set to a null value.

12. The system of claim 8, wherein repeating steps (a)-(c) on the first individual file from the second or subsequent regions of interest files comprises:

(i) applying the first denoising threshold value and the second denoising threshold value to all the first individual files in the second or subsequent regions of interest files, (ii) applying new minimum threshold values and uniform threshold values to each of the first individual signal files in the second or subsequent regions of interest files, or (iii) a combination of (i) and (ii).

13. The system of claim 8, wherein the image pre-processing further comprises:

performing another iterative process starting with a first denoised image from the set of denoised images, wherein the other iterative process comprises:

(e) processing the first denoised image using a spillover correction filter to generate a spillover corrected image, (f) processing the spillover corrected image using an aggregate removal filter to generate an aggregate removal image, and (g) repeating steps (e) and (f) for a second or subsequent denoised image from the set of denoised images to generate a set of stacked images comprising the aggregate removal images.

14. The system of claim 13, further comprises performing downstream analysis on the set of stacked images, wherein the downstream analysis comprises:

generating, by a cell segmentation tool using the set of stacked images, single-cell masks and a marker-expression matrix;

generating, by a cell-phenotype identification pipeline using the single-cell masks and the marker-expression matrix, subclusters of cells based on their expression of lineage markers;

generating, by an extraction algorithm using the expression of lineage markers associated with each subcluster of cells, a labeled dataset comprising a list the subclusters of cells and their corresponding expression patterns of the lineage markers;

determining, by inputting the labeled dataset into a machine learning model, a clinical outcome based on the subclusters of cells.

15. One or more non-transitory computer-readable media storing instructions which, when executed by one or more processors, cause a system to perform operations comprising:

accessing an image file of a specimen stained with a panel of antibodies, wherein:

the image file comprises regions of interest files of the specimen, the regions of interest files comprise individual signal files corresponding to each antibody in the panel of antibodies used to stain the specimen, and the individual signal files comprise artifact signals corresponding to background noise;

performing an image pre-processing method to remove the artifact signals from the individual signal files, wherein the image pre-processing method comprises:

US 12,620,069 B2

63 performing an iterative process comprising:

(a) applying, to a first individual signal file of the individual signal files from a first region on interest file of the regions of interest files using a denoising filter, a first denoising threshold value to generate a first noise signal and a second denoising threshold value to generate a second noise signal, (b) removing, from the first individual signal file, the first noise signal and the second noise signal to generate a denoised image, (c) comparing the first individual signal file to the denoised image to determine the performance quality of the denoising filter, and (d) choosing, based on the comparing, to: (i) repeat steps (a)-(c) on the first individual file from the first region of interest file by modifying the first denoising threshold value and the second denoising threshold value, (ii) repeat steps (a)-(c) on the first individual signal file from a second or subsequent region of interest file of the regions of interest files, or (iii) ending the iterative process for the first individual signal file, and repeating the iterative process on a second or subsequent individual signal file of the individual signal files from the first region of interest to generate a set of denoised images for the specimen; and outputting the set of denoised images.

16. The one or more non-transitory computer-readable media of claim 15, wherein:

(i) the panel of antibodies comprise two or more antibodies that recognize CD66b, CD20, CD28, CD16, CD163, CD11b, CD45, CD4, CD31, CD279, CD68, Foxp3, CK7, Ki-67, CD8a, Collagen Type I, CD3e, CD138, HLA-DR, Granzyme B, DNA1, DNA2, or any combination thereof, and (ii) the panel of antibodies are labeled with metal tags and wherein the metal tags comprise 139La, 142Nd, 144Nd, 146Nd, 147Sm, 149Sm, 152Sm, 153Eu, 154Sm, 156Gd, 159Tb, 160Gd, 164Dy, 167Er, 168Er, 169Tm, 170Er, 172Yb, 174Yb, 175Lu, 191Ir, 193Ir, or any combination thereof.

17. The one or more non-transitory computer-readable media of claim 15, wherein:

the first denoising threshold value is a minimum filter value dependent upon the antibody panel and corresponding to a signal level below a designated minimum threshold, and the second denoising threshold value is a uniform filter value used to average pixel intensities, and (i) the minimum filter value is set to a desired integer and the uniform threshold value is set to null, (ii) the minimum filter value is set to a null value and the uniform threshold value is set to a desired integer value,

64

(iii) the minimum filter value is set to a desired integer and the uniform threshold value is set to a desired integer value, or (iv) the minimum filter value is set to a null value and the uniform threshold value is set to a null value.

18. The one or more non-transitory computer-readable media of claim 15, wherein repeating steps (a)-(c) on the first individual file from the second or subsequent regions of interest files comprises:

(i) applying the first denoising threshold value and the second denoising threshold value to all the first individual files in the second or subsequent regions of interest files, (ii) applying new minimum threshold values and uniform threshold values to each of the first individual signal files in the second or subsequent regions of interest files, or (iii) a combination of (i) and (ii).

19. The one or more non-transitory computer-readable media of claim 15, wherein the image pre-processing further comprises:

performing another iterative process starting with a first denoised image from the set of denoised images, wherein the other iterative process comprises:

(e) processing the first denoised image using a spillover correction filter to generate a spillover corrected image, (f) processing the spillover corrected image using an aggregate removal filter to generate an aggregate removal image, and (g) repeating steps (e) and (f) for a second or subsequent denoised image from the set of denoised images to generate a set of stacked images comprising the aggregate removal images.

20. The one or more non-transitory computer-readable media of claim 19, further comprises performing downstream analysis on the set of stacked images, wherein the downstream analysis comprises:

generating, by a cell segmentation tool using the set of stacked images, single-cell masks and a marker-expression matrix;

generating, by a cell-phenotype identification pipeline using the single-cell masks and the marker-expression matrix, subclusters of cells based on their expression of lineage markers;

generating, by an extraction algorithm using the expression of lineage markers associated with each subcluster of cells, a labeled dataset comprising a list the subclusters of cells and their corresponding expression patterns of the lineage markers;

determining, by inputting the labeled dataset into a machine learning model, a clinical outcome based on the subclusters of cells.

* * * * *